US012325707B2

(12) United States Patent
Lewis et al.

(10) Patent No.: US 12,325,707 B2
(45) Date of Patent: Jun. 10, 2025

(54) PROCESS FOR PREPARING ENANTIOMERICALLY ENRICHED JAK INHIBITORS

(71) Applicant: Sun Pharmaceutical Industries, Inc., Princeton, NJ (US)

(72) Inventors: Robert S. Lewis, Lexington, MA (US); Mahender Reddy Karla, Lexington, MA (US); Kathryn E. Kavouris, Cambridge, MA (US); Yong Dong, Chestnut Hill, MA (US); Adam J. Morgan, Ashland, MA (US); Cameron J. Cowden, Lexington, MA (US)

(73) Assignee: SUN PHARMACEUTICAL INDUSTRIES, INC., Princeton, NJ (US)

( * ) Notice: Subject to any disclaimer, the term of this patent is extended or adjusted under 35 U.S.C. 154(b) by 762 days.

(21) Appl. No.: 17/428,850

(22) PCT Filed: Feb. 6, 2020

(86) PCT No.: PCT/US2020/017093
§ 371 (c)(1),
(2) Date: Aug. 5, 2021

(87) PCT Pub. No.: WO2020/163653
PCT Pub. Date: Aug. 13, 2020

(65) Prior Publication Data
US 2022/0306636 A1    Sep. 29, 2022

Related U.S. Application Data

(60) Provisional application No. 62/850,981, filed on May 21, 2019, provisional application No. 62/802,129, filed on Feb. 6, 2019.

(51) Int. Cl.
| | | |
|---|---|---|
| *C07D 487/04* | (2006.01) | |
| *C07B 59/00* | (2006.01) | |
| *C07C 309/65* | (2006.01) | |
| *C07D 403/04* | (2006.01) | |

(52) U.S. Cl.
CPC .......... *C07D 487/04* (2013.01); *C07B 59/002* (2013.01); *C07C 309/65* (2013.01); *C07D 403/04* (2013.01)

(58) Field of Classification Search
CPC .. C07D 487/04; C07D 403/04; C07B 59/002; C07C 309/65
See application file for complete search history.

(56) References Cited

U.S. PATENT DOCUMENTS 8,410,265 B2 *   4/2013   Zhou .................... C07D 487/04
                                                                544/280
9,249,149 B2    2/2016   Silverman et al.

FOREIGN PATENT DOCUMENTS

| CN | 105669675 A | 6/2016 |
| CN | 107759623 A | 3/2018 |
| CN | 107915738 A * | 4/2018 |
| WO | 2013/188783 A1 | 12/2013 |

OTHER PUBLICATIONS

Google Patent—English Machine Translation—CN107915738A (published Nov. 14, 2017) (Year: 2017).*
PubChem CID 7270461_ Deuruxolitinib, D8-ruxolitinib and CTP-543. (Year: 2014).*
Gannes et al., "Natural abundance variations in stable isotopes and their potential uses in animal physiological ecology," Comparative Biochemistry and Physiology Part A: Molecular & Integrative Physiology 119(3):725-737 (1998).
Shiner et al., "Deuterium Isotope Effects for Migrating and Nonmigrating Groups in the Solvolysis of Neopentyl-Type Esters," Journal of the American Chemical Society 103(2):436-442 (1981).
Wada and Hanba, "Natural abundance of carbon, nitrogen, and hydrogen isotope ratios in biogenic substances: present and future," Seikagaku. The Journal of Japanese Biochemical Society 66(1):15-29 (1994). Machine Translation of Abstract.
Zhang et al., "An improved synthesis of 4-chloro-7H-pyrrolo[2,3-d]pyrimidine," 54(6):638-642 (2018).
International Search Report and Written Opinion mailed in International Application No. PCT/US2020/017093 on Apr. 30, 2020.
Unpublished Copending U.S. Appl. No. 18/666,084, Titled: "Process for Preparing Enantiomerically Enriched JAK Inhibitors" by Inventor Robert S. Lewis et al., Filed on May 16, 2024.

* cited by examiner

*Primary Examiner* — Clinton A Brooks
*Assistant Examiner* — Josmalen M. Ramos-Lewis
(74) *Attorney, Agent, or Firm* — MEDLER FERRO WOODHOUSE & MILLS PLLC

(57) ABSTRACT

Improved processes and intermediates for preparing ruxolitinib and deuterated analogs of ruxolitinib are disclosed.

19 Claims, No Drawings

PROCESS FOR PREPARING ENANTIOMERICALLY ENRICHED JAK INHIBITORS

CROSS-REFERENCE TO RELATED APPLICATIONS

This application is the U.S. National Stage of International Application No. PCT/US2020/017093, filed Feb. 6, 2020, which designates the U.S., published in English, and claims the benefit of U.S. Provisional Application No. 62/802,129, filed on Feb. 6, 2019 and U.S. Provisional Application No. 62/850,981, filed on May 21, 2019. The entire teachings of the above applications are incorporated herein by reference.

BACKGROUND OF THE INVENTION

Ruxolitinib phosphate is a heteroaryl-substituted pyrrolo[2,3-d]pyrimidine, also known as 3(R)-cyclopentyl-3-[4-(7H-pyrrolo[2,3-d]pyrimidin-4-yl)-1H-pyrazol-1-yl]propanenitrile phosphate, and as (R)-3-(4-(7H-pyrrolo[2,3-d]pyrimidin-4-yl)-1H-pyrazol-1-yl)-3-cyclopentylpropanenitrile phosphate, which inhibits Janus Associated Kinases (JAKs) JAK1 and JAK2. These kinases mediate the signaling of a number of cytokines and growth factors important for hematopoiesis and immune function. JAK signaling involves recruitment of STATs (signal transducers and activators of transcription) to cytokine receptors, activation and subsequent localization of STATs to the nucleus leading to modulation of gene expression.

Ruxolitinib phosphate has been approved in the US and Europe for the treatment of myelofibrosis and for the treatment of polycythemia vera. Ruxolitinib is currently in clinical trials for the treatment of graft-versus-host disease and other conditions.

A deuterated analog of ruxolitinib phosphate (referred to herein as CTP-543 or Compound (I)) is currently in clinical trials for the treatment of alopecia areata.

Because of the beneficial activities of ruxolitinib and deuterated ruxolitinib analogs, there is a continuing need for improved methods for synthesizing ruxolitinib and deuterated forms thereof.

SUMMARY OF THE INVENTION

The present invention provides improved methods for synthesizing ruxolitinib and deuterated forms thereof. The present invention further provides intermediates useful for synthesizing ruxolitinib and deuterated forms thereof.

In one aspect, the invention provides a process for preparing a compound of Formula I:

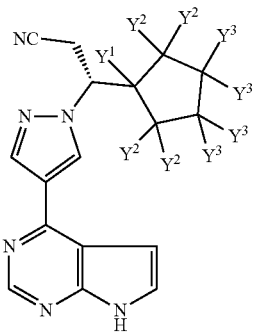

Formula I or a salt thereof, the process comprising reacting a compound of Formula II:

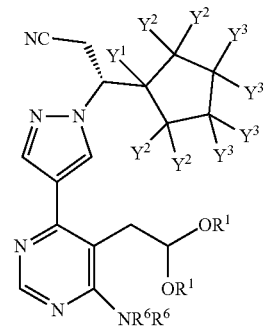

Formula II or a salt thereof, in the presence of an acid such that a compound of Formula I is formed; wherein in Formula I and Formula II, $Y^1$ is hydrogen or deuterium; each $Y^2$ is the same and is hydrogen or deuterium; each $Y^3$ is the same and is hydrogen or deuterium; and in Formula II each $R^1$ is $C_1$-$C_6$ alkyl, or taken together the two $R^1$s form a $C_2$ or $C_3$ alkylene moiety (i.e., the two $R^1$s, taken together with the oxygen atoms to which they are attached, form a 5- or 6-membered heterocyclic ring); and each $R^6$ is independently selected from H and a protecting group. In certain embodiments, the acid is selected from trifluoroacetic acid (TFA), phosphoric acid, trifluoroacetic anhydride (TFAA), or a combination thereof. In certain embodiments, the acid is selected from trifluoroacetic acid (TFA), phosphoric acid, hydrochloric acid, or a combination thereof. In certain embodiments, the acid is hydrochloric acid.

In one aspect, the invention provides a process for preparing a compound of Formula I:

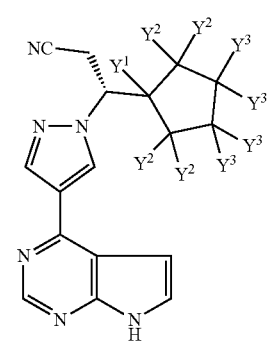

Formula I or a salt thereof, the process comprising reacting a compound of Formula II':

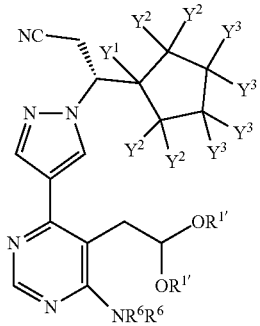

Formula II' or a salt thereof, in the presence of an acid such that a compound of Formula I is formed; wherein in Formula I and Formula II', $Y^1$ is hydrogen or deuterium; each $Y^2$ is the same and is hydrogen or deuterium; each $Y^3$ is the same and is hydrogen or deuterium; and in Formula II', each $R^{1'}$ is $C_1$-$C_{10}$ alkyl (e.g., methyl or ethyl), or $C_2$-$C_{10}$ alkenyl (e.g., allyl), or the two $R^{1'}$s, taken together with the oxygen atoms to which they are attached, form a 5-7-membered heterocyclic ring which may optionally be substituted (e.g., a 1,3-dioxolan-2-yl ring, or a 1,3-dioxan-2-yl ring, or a 1,3-benzodioxolan-2-yl ring, each optionally substituted with one or more methyl groups); and each $R^6$ is independently selected from H and a protecting group. In certain embodiments, the acid is selected from hydrochloric acid, trifluoroacetic acid (TFA), phosphoric acid, or a combination thereof. In certain embodiments, $Y^1$ is hydrogen; each $Y^2$ is the same and is hydrogen; and each $Y^3$ is the same and is hydrogen. In other embodiments, $Y^1$ is deuterium; each $Y^2$ is the same and is deuterium; and each $Y^3$ is the same and is deuterium. In certain embodiments, each $R^{1'}$ is $C_1$-$C_{10}$ alkyl; in further embodiments, each $R^{1'}$ is methyl or ethyl. In certain embodiments, each $R^6$ is H. In certain embodiments, one $R^6$ is H and one $R^6$ is a protecting group. In certain embodiments, each $R^6$ is a protecting group. In certain embodiments, the protecting group is a t-butoxycarbonyl group.

In another aspect, the invention provides a process for preparing a compound of Formula II (or a salt thereof):

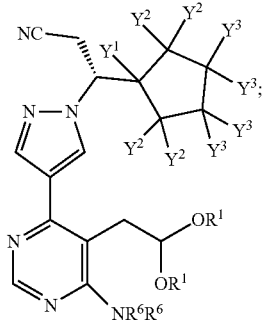

Formula II the process comprising reacting a compound of Formula III (or a salt thereof):

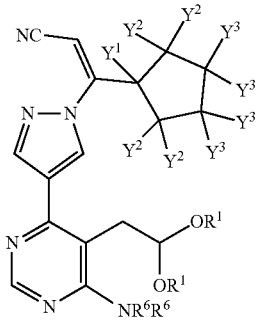

Formula III with a hydrogen source (e.g., hydrogen gas) in the presence of a hydrogenation catalyst; wherein $Y^1$ is hydrogen or deuterium; each $Y^2$ is the same and is hydrogen or deuterium; each $Y^3$ is the same and is hydrogen or deuterium; each $R^1$ is $C_1$-$C_6$ alkyl, or taken together the two $R^1$s form a $C_2$ or $C_3$ alkylene moiety; and each $R^6$ is independently selected from H and a protecting group.

In another aspect, the invention provides a process for preparing a compound of Formula II' (or a salt thereof):

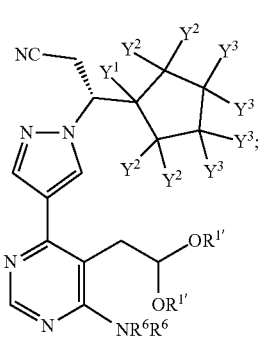

Formula II' the process comprising reacting a compound of Formula III' (or a salt thereof):

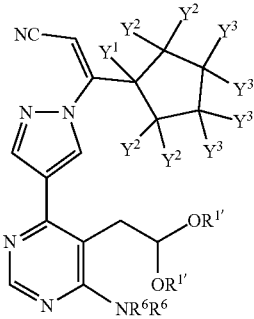

Formula III' with a hydrogen source (e.g., hydrogen gas) in the presence of a hydrogenation catalyst; wherein in Formula II' and III', $Y^1$ is hydrogen or deuterium; each $Y^2$ is the same and is hydrogen or deuterium; each $Y^3$ is the same and is hydrogen or deuterium; each $R^{1'}$ is $C_1$-$C_{10}$ alkyl (e.g., methyl or ethyl), or $C_2$-$C_{10}$ alkenyl (e.g., allyl), or the two $R^{1'}$s, taken together with the oxygen atoms to which they are attached, form a 5-7-membered heterocyclic ring which may optionally be substituted (e.g., a 1,3-dioxolan-2-yl ring, or a 1,3-dioxan-2-yl ring, or a 1,3-benzodioxolan-2-yl ring); and each $R^6$ is independently selected from H and a protecting group. In certain embodiments, $Y^1$ is hydrogen; each $Y^2$ is the same and is hydrogen; and each $Y^3$ is the same and is hydrogen. In other embodiments, $Y^1$ is deuterium; each $Y^2$ is the same and is deuterium; and each $Y^3$ is the same and is deuterium. In certain embodiments, each $R^{1'}$ is $C_1$-$C_{10}$ alkyl; in further embodiments, each $R^{1'}$ is methyl or ethyl. In certain embodiments, each $R^6$ is H. In certain embodiments, one $R^6$ is H and one $R^6$ is a protecting group. In certain embodiments, each $R^6$ is a protecting group. In certain embodiments, the protecting group is a t-butoxycarbonyl group.

In certain embodiments of the above processes for producing a compound of Formula II or II', the hydrogenation catalyst comprises a transition metal including, but not limited to, rhodium, ruthenium, and iridium. In certain embodiments, the hydrogenation catalyst comprises a transition metal selected from rhodium, ruthenium, and iridium, and a chiral phosphine ligand (L) according to Formula IV below. In certain embodiments, the hydrogenation catalyst comprises rhodium. In certain embodiments, the hydrogenation catalyst comprises rhodium and a chiral phosphine ligand (L) according to Formula IV:

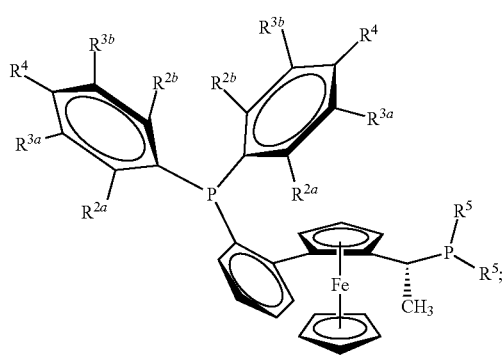

Formula IV wherein each of $R^{2a}$, $R^{2b}$, $R^{3a}$, $R^{3b}$, and $R^4$ is independently selected from hydrogen, methyl, methoxy, and trifluoromethyl; and $R^5$ is secondary alkyl, tertiary alkyl, or cycloalkyl.

In certain embodiments, each of $R^{2a}$, $R^{2b}$, $R^{3a}$, $R^{3b}$, and $R^4$ is hydrogen, and $R^5$ is norbornyl. In certain embodiments, each of $R^{2a}$, $R^{2b}$, $R^{3a}$, $R^{3b}$, and $R^4$ is hydrogen, and $R^5$ is cyclohexyl. In certain embodiments, the hydrogenation catalyst is present in an amount of 2.5 mol % or less. In certain embodiments, the hydrogenation catalyst is present in an amount of 1 mol % or less.

In certain embodiments, the hydrogen gas is present at a pressure of 15 bar or less. In certain embodiments, the hydrogen gas is present at a pressure of 10 bar or less. In certain embodiments, the step of reacting the compound of Formula III or III' with hydrogen gas in the presence of a hydrogenation catalyst is performed in a solvent, and the solvent is selected from dichloromethane (DCM), trifluorotoluene (TFT), tetrahydrofuran (THF), 2-methyltetrahydrofuran (2-methyl-THF), methanol (MeOH), ethanol (EtOH), trifluoroethanol (TFE), isopropanol (iPrOH), hexafluoroisopropanol (HFIP), ethyl acetate (EtOAc), isopropyl acetate (iPrOAc), acetic acid (AcOH), and mixtures thereof. In certain embodiments, the solvent is trifluoroethanol (TFE). In certain embodiments, the compound of Formula II or II' has an enantiomeric excess of the (R)-enantiomer of at least 95%. In certain embodiments, the compound of Formula II or II' has an enantiomeric excess of the (R)-enantiomer of at least 98%.

In another aspect, the invention provides a process for preparing a compound of Formula III (or a salt thereof):

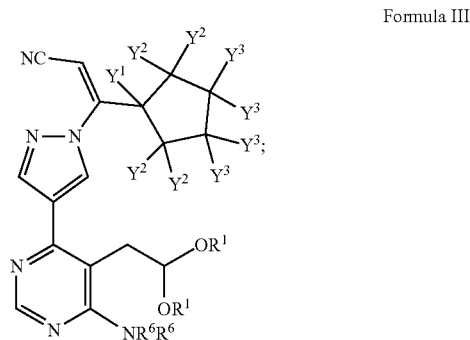

Formula III the process comprising reacting a compound of Formula VIII (or a salt thereof):

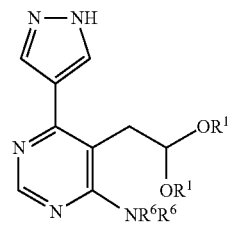

Formula VIII with a compound of Formula VII:

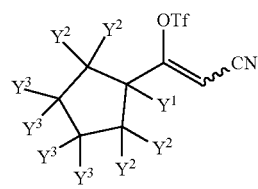

Formula VII in the presence of a base, such that a compound of Formula III is formed; wherein $Y^1$ is hydrogen or deuterium; each $Y^2$ is the same and is hydrogen or deuterium; each $Y^3$ is the same and is hydrogen or deuterium; each $R^1$ is $C_1$-$C_6$ alkyl, or taken together the two $R^1$s form a $C_2$ or $C_3$ alkylene moiety; and each $R^6$ is independently selected from H and a protecting group. In certain embodiments, the base is selected from tripotassium phosphate, hydrated tripotassium phosphate and potassium carbonate.

In another aspect, the invention provides a process for preparing a compound of Formula III' (or a salt thereof):

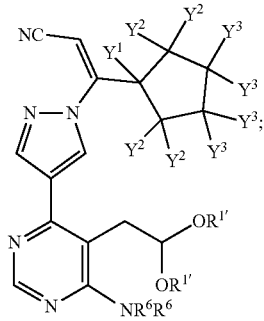

Formula III' the process comprising reacting a compound of Formula VIII' (or a salt thereof):

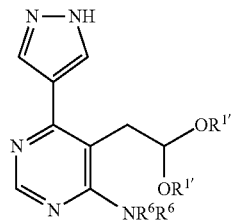

Formula VIII' with a compound of Formula VII:

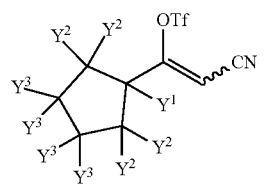

Formula VII in the presence of a base, such that a compound of Formula III' (or salt thereof) is formed; wherein in Formula III' and VII, $Y^1$ is hydrogen or deuterium; each $Y^2$ is the same and is hydrogen or deuterium; each $Y^3$ is the same and is hydrogen or deuterium; and in Formula III' and VIII', each $R^{1'}$ is $C_1$-$C_{10}$ alkyl (e.g., methyl or ethyl), or $C_2$-$C_{10}$ alkenyl (e.g., allyl), or the two $R^{1'}$s, taken together with the oxygen atoms to which they are attached, form a 5-7-membered heterocyclic ring which may optionally be substituted (e.g., a 1,3-dioxolan-2-yl ring, or a 1,3-dioxan-2-yl ring, or a 1,3-benzodioxolan-2-yl ring, which may be substituted with, e.g., one or more methyl groups); and each $R^6$ is independently selected from H and a protecting group. In certain embodiments, $Y^1$ is hydrogen; each $Y^2$ is the same and is hydrogen; and each $Y^3$ is the same and is hydrogen. In other embodiments, $Y^1$ is deuterium; each $Y^2$ is the same and is deuterium; and each $Y^3$ is the same and is deuterium. In certain embodiments, each $R^{1'}$ is $C_1$-$C_{10}$ alkyl; in further embodiments, each $R^{1'}$ is methyl or ethyl. In certain embodiments, each $R^6$ is H. In certain embodiments, one $R^6$ is H and one $R^6$ is a protecting group. In certain embodiments, each $R^6$ is a protecting group. In certain embodiments, the protecting group is a t-butoxycarbonyl group. In certain embodiments, the base is selected from tripotassium phosphate, hydrated tripotassium phosphate and potassium carbonate. In some embodiments, the step of reacting is performed in a solvent. Nonlimiting examples of solvents include dimethylacetamide (DMAc), water ($H_2O$), and combinations thereof. In certain embodiments, the solvent is a combination of dimethylacetamide and water, for example, dimethylacetamide and water in a ratio in the range between 7:1 DMac:water and 1:2 DMac:water, such as 7:1 DMac:water, 5:4 DMac/water, or 2:1 DMac/water. In some embodiments, the reaction is performed at one or more temperatures in the range of 0° C. to room temperature, e.g, in the range of 0 to 23° C.

Certain aspects of the present invention are directed to a process for preparing a compound of Formula VIII (or a salt thereof):

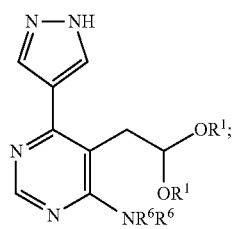

Formula VIII the process comprising reacting a compound of Formula IX (or a salt thereof):

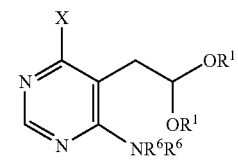

Formula IX with a compound represented by the formula:

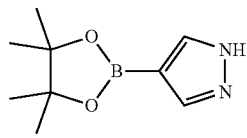

(BPin-pyrazole) (or another pyrazole boronic ester) and a catalytic amount of a palladium catalyst (such as Pd(PPh$_3$)$_4$) in the presence of a base such that a compound of Formula VIII is formed; wherein each $R^1$ is $C_1$-$C_6$ alkyl, or taken together the two $R^1$s form a $C_2$ or $C_3$ alkylene moiety; each $R^6$ is independently selected from H and a protecting group; and X is I, Br, Cl, or triflate. In certain embodiments, the base is selected from potassium carbonate and dibasic sodium phosphate dihydrate.

Certain aspects of the present invention are directed to a process for preparing a compound of Formula VIII' (or a salt thereof):

Formula VIII'

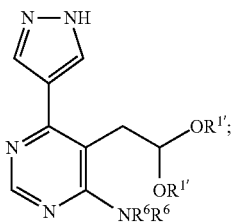

the process comprising reacting a compound of Formula IX' (or a salt thereof):

Formula IX'

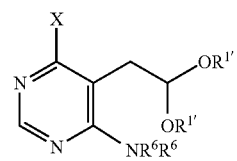

with a compound represented by the formula:

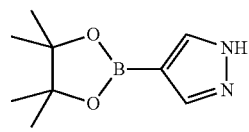

(BPin-pyrazole) (or another pyrazole boronic ester) and a catalytic amount of a palladium catalyst (such as Pd(PPh$_3$)$_4$) in the presence of a base, such that a compound of Formula VIII' is formed; wherein in Formula VIII' and IX', each R$^{1'}$ is C$_1$-C$_{10}$ alkyl (e.g., methyl or ethyl), or C$_2$-C$_{10}$ alkenyl (e.g., allyl), or the two R$^{1'}$s, taken together with the oxygen atoms to which they are attached, form a 5-7-membered heterocyclic ring which may optionally be substituted (e.g., a 1,3-dioxolan-2-yl ring, or a 1,3-dioxan-2-yl ring, or a 1,3-benzodioxolan-2-yl ring); and each R$^6$ is independently selected from H and a protecting group. In certain embodiments, each R$^{1'}$ is C$_1$-C$_{10}$ alkyl; in further embodiments, each R$^{1'}$ is methyl or ethyl. In certain embodiments, each R$^6$ is H. In certain embodiments, one R$^6$ is H and one R$^6$ is a protecting group. In certain embodiments, each R$^6$ is a protecting group. In certain embodiments, the protecting group is a t-butoxycarbonyl group. In certain embodiments, the base is selected from potassium carbonate and dibasic sodium phosphate dihydrate.

In any of the formulae described herein, in certain embodiments, the protecting group is selected from t-butoxycarbonyl (Boc), triflyl (Tf, SO$_2$—CF$_3$), trifluoroacetyl (F$_3$—Ac), and trityl (Tr, CPh$_3$). In certain embodiments, both R$^6$ are H. In certain embodiments, both R$^1$ are methyl. In certain embodiments, both R$^1$ are ethyl. In certain embodiments, both R$^{1'}$s are methyl. In certain embodiments, both R$^{1'}$s are ethyl. In certain embodiments, Y$^1$ is hydrogen and each of Y$^2$ and Y$^3$ is deuterium. In certain embodiments, each of Y$^1$, Y$^2$, and Y$^3$ is hydrogen. In certain embodiments, the deuterium incorporation at each position designated as deuterium is at least 90%, at least 95%, or at least 97%.

Certain aspects of the present invention provide intermediates useful for preparing ruxolitinib and deuterated analogs of ruxolitinib. In one embodiment, the invention provides a compound represented by the structure:

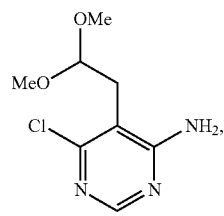 [SMILES: COC(Cc1c(N)ncnc1Cl)OC]

or a salt thereof.

In another embodiment, the invention provides a compound represented by the structure:

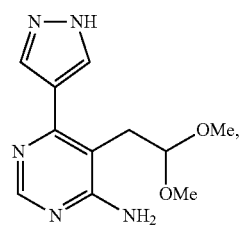 [SMILES: COC(Cc1c(N)ncnc1-c1cn[nH]c1)OC]

or a salt thereof.

In another embodiment, the invention provides a compound represented by the structure:

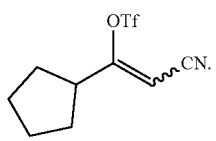 [SMILES: N#CC=C(OS(=O)(=O)C(F)(F)F)C1CCCC1]

In another embodiment, the invention provides a compound represented by the structure:

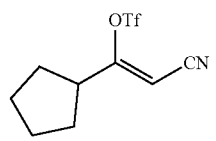 [SMILES: N#C/C=C(\OS(=O)(=O)C(F)(F)F)C1CCCC1]

In another embodiment, the invention provides a compound represented by the structure:

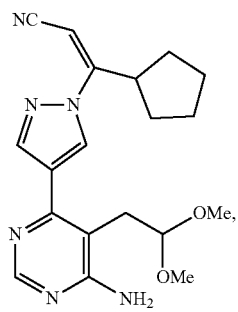 [SMILES: COC(Cc1c(N)ncnc1-c1cnn(/C(=C\C#N)C2CCCC2)c1)OC]

or a salt thereof.

In another embodiment, the invention provides a compound represented by the structure:

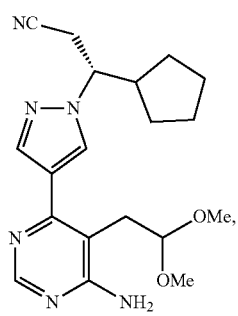 [SMILES: COC(Cc1c(N)ncnc1-c1cnn([C@H](CC#N)C2CCCC2)c1)OC]

or a salt thereof.

In another embodiment, the invention provides a compound represented by the structure:

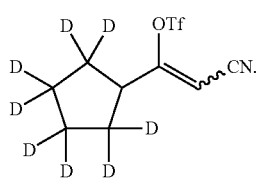 [SMILES: [2H]C1([2H])C(C(=CC#N)OS(=O)(=O)C(F)(F)F)C([2H])([2H])C([2H])([2H])C1([2H])[2H]]

In another embodiment, the invention provides a compound represented by the structure:

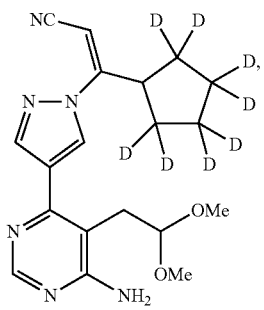

or a salt thereof.

In another embodiment, the invention provides a compound represented by the structure:

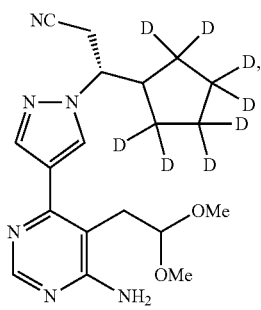

or a salt thereof.

In another embodiment, the invention provides a compound represented by the structure:

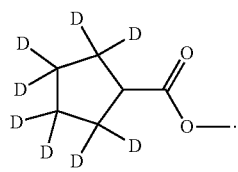

In another embodiment, the invention provides a compound represented by the structure:

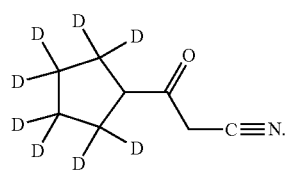 [SMILES: [2H]C1([2H])C(C(=O)CC#N)C([2H])([2H])C([2H])([2H])C1([2H])[2H]]

In another embodiment, the invention provides a compound represented by the structure:

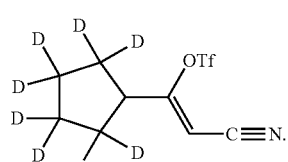

In certain embodiments, the deuterium incorporation at each position that is designated as deuterium in any compound of this invention is at least 90%, at least 95%, or at least 97%.

Other aspects and embodiments of the invention will be appreciated from the detailed description and claims herein.

DETAILED DESCRIPTION OF THE INVENTION

Definitions

The term "alkyl" refers to a monovalent saturated hydrocarbon group. $C_1$-$C_6$ alkyl is an alkyl having from 1 to 6 carbon atoms. In some embodiments, an alkyl may be linear or branched. In some embodiments, an alkyl may be primary, secondary, or tertiary. Non-limiting examples of alkyl groups include methyl; ethyl; propyl, including n-propyl and isopropyl; butyl, including n-butyl, isobutyl, sec-butyl, and t-butyl; pentyl, including, for example, n-pentyl, isopentyl, and neopentyl; and hexyl, including, for example, n-hexyl and 2-methylpentyl. Non-limiting examples of primary alkyl groups include methyl, ethyl, n-propyl, n-butyl, n-pentyl, and n-hexyl. Non-limiting examples of secondary alkyl groups include isopropyl, sec-butyl, and 2-methylpentyl. Non-limiting examples of tertiary alkyl groups include t-butyl.

Unless otherwise specified, "alkylene" by itself or as part of another substituent refers to a saturated straight-chain or branched divalent group having the stated number of carbon atoms and derived from the removal of two hydrogen atoms from the corresponding alkane. Examples of straight chained and branched alkylene groups include —$CH_2$— (methylene), —$CH_2$—$CH_2$— (ethylene), —$CH_2$—$CH_2$—$CH_2$— (propylene), —$C(CH_3)_2$—, —$CH_2$—$CH(CH_3)$—, —$CH_2$—$CH_2$—$CH_2$—$CH_2$— (butylene), —$CH_2$—$CH(CH_3)$—$CH_2$—, —$CH_2$—$CH_2$—$CH_2$—$CH_2$—$CH_2$— (pentylene), and —$CH_2$—$C(CH_3)_2$—$CH_2$—.

The term "alkenyl" refers to a monovalent unsaturated hydrocarbon group where the unsaturation is represented by a double bond. $C_2$-$C_6$ alkenyl is an alkenyl having from 2 to 6 carbon atoms. An alkenyl may be linear or branched. Examples of alkenyl groups include $CH_2$=CH— (vinyl), $CH_2$=$C(CH_3)$—, $CH_2$=CH—$CH_2$— (allyl), $CH_3$—CH=CH—$CH_2$— (crotyl), $CH_3$—CH=$C(CH_3)$— and $CH_3$—CH=CH—$CH(CH_3)$—$CH_2$—. Where double bond stereoisomerism is possible, the stereochemistry of an alkenyl may be (E), (Z), or a mixture thereof.

The term "alkynyl" refers to a monovalent unsaturated hydrocarbon group where the unsaturation is represented by a triple bond. $C_2$-$C_6$ alkynyl is an alkynyl having from 2 to 6 carbon atoms. An alkynyl may be linear or branched. Examples of alkynyl groups include HC≡C—, $CH_3$—C≡C—, $CH_3$—C≡C—$CH_2$—, $CH_3$—C≡C—$CH_2$—$CH_2$— and $CH_3$—C≡C—$CH(CH_3)$—$CH_2$—.

The term "cycloalkyl" refers to a monocyclic or bicyclic monovalent saturated or non-aromatic unsaturated hydrocarbon ring system. The term "$C_3$-$C_{10}$ cycloalkyl" refers to a cycloalkyl wherein the number of ring carbon atoms is from 3 to 10. Examples of $C_3$-$C_{10}$ cycloalkyl include $C_3$-$C_6$ cycloalkyl. Bicyclic ring systems include fused, bridged, and spirocyclic ring systems. Non-limiting examples of cycloalkyl groups include cyclopropyl, cyclobutyl, cyclopentyl, cyclohexyl, cycloheptyl, cis- and trans-decalinyl, norbornyl, and spiro[4.5]decanyl.

The term "carbocyclyl" refers to a monocyclic or bicyclic monovalent saturated or non-aromatic unsaturated hydrocarbon ring system. The term "$C_3$-$C_{10}$ carbocyclyl" refers to a carbocyclyl wherein the number of ring carbon atoms is from 3 to 10. Examples of $C_3$-$C_{10}$ carbocyclyl include $C_3$-$C_6$ carbocyclyl. Bicyclic ring systems include fused, bridged, and spirocyclic ring systems. More particular examples of carbocyclyl groups include, cyclopropyl, cyclobutyl, cyclopentyl, cyclopentenyl, cyclohexyl, cyclohexenyl, cycloheptyl, cis- and trans-decalinyl, norbornyl, norbornenyl, and spiro[4.5]decanyl.

The term "heterocycloalkyl" refers to a monocyclic or bicyclic monovalent saturated or non-aromatic unsaturated ring system wherein from 1 to 4 ring atoms are heteroatoms independently selected from the group consisting of O, N and S. The term "3 to 10-membered heterocycloalkyl" refers to a heterocycloalkyl wherein the number of ring atoms is from 3 to 10. Examples of 3 to 10-membered heterocycloalkyl include 3 to 6-membered heterocycloalkyl. Bicyclic ring systems include fused, bridged, and spirocyclic ring systems. More particular examples of heterocycloalkyl groups include azepanyl, azetidinyl, aziridinyl, imidazolidinyl, morpholinyl, oxazolidinyl, oxazolidinyl, piperazinyl, piperidinyl, pyrazolidinyl, pyrrolidinyl, quinuclidinyl, and thiomorpholinyl.

In the above heterocycloalkyl substituents, the nitrogen, phosphorus, carbon or sulfur atoms can be optionally oxidized to various oxidation states. In a specific example, the group —$S(O)_{0-2}$—, refers to —S-(sulfide), —S(O)-(sulfoxide), and —$SO_2$-(sulfone) respectively. For convenience, nitrogens, particularly but not exclusively, are meant to include their corresponding N-oxide form, although not explicitly defined as such in a particular example. Thus, for a compound of the invention having, for example, a pyridyl ring; the corresponding pyridyl-N-oxide is meant to be included as another compound of the invention. In addition, annular nitrogen atoms can be optionally quaternized; and the ring substituent can be partially or fully saturated or aromatic.

"Aryl" by itself or as part of another substituent refers to a monocyclic or polycyclic monovalent aromatic hydrocarbon group having the stated number of carbon atoms (i.e., $C_5$-$C_{14}$ means from 5 to 14 carbon atoms). Typical aryl groups include, but are not limited to, groups derived from aceanthrylene, acenaphthylene, acephenanthrylene, anthracene, azulene, benzene, chrysene, coronene, fluoranthene, fluorene, hexacene, hexaphene, hexylene, as-indacene, s-indacene, indane, indene, naphthalene, octacene, octophene, octalene, ovalene, penta-2,4-diene, pentacene, pentalene, pentaphene, perylene, phenalene, phenanthrene, picene, pleiadene, pyrene, pyranthrene, rubicene, triphenylene, trinaphthylene, and the like. In a specific embodiment, the aryl group is cyclopentadienyl, phenyl or naphthyl. In a more specific embodiment, the aryl group is phenyl or naphthyl.

"Arylalkyl" by itself or as part of another substituent refers to an acyclic alkyl group in which one of the hydrogen atoms bonded to a carbon atom, typically a terminal or sp³ carbon atom, is replaced with an aryl group. Typical arylalkyl groups include, but are not limited to, benzyl, 2-phenylethan-1-yl, 2-phenylethen-1-yl, naphthylmethyl, 2-naphthylethan-1-yl, 2-naphthylethen-1-yl, naphthobenzyl, 2-naphthophenylethan-1-yl and the like. In one embodiment, the alkyl moiety of the arylalkyl group is ($C_1$-$C_6$) and the aryl moiety is ($C_5$-$C_{14}$). In a more specific embodiment the alkyl group is ($C_1$-$C_3$) and the aryl moiety is ($C_5$-$C_{10}$), such as ($C_6$-$C_{10}$).

The term "heteroaryl" refers to a monocyclic or polycyclic (e.g., having 2, 3, or 4 fused rings) aromatic hydrocarbon ring system, wherein at least one ring atom is a heteroatom independently selected from the group consisting of O, N and S. In some embodiments, the heteroaryl group has 1 or 2 rings. When the heteroaryl group contains more than one heteroatom ring member, the heteroatoms may be the same or different. Nonlimiting examples of heteroaryl groups include without limitation, pyrrolopyrimidinyl, pyridyl, pyrimidinyl, pyrazinyl, pyridazinyl, triazinyl, furyl, quinolyl, isoquinolyl, thienyl, imidazolyl, thiazolyl, indolyl, pyrryl, oxazolyl, benzofuryl, benzothienyl, benzthiazolyl, isoxazolyl, pyrazolyl, triazolyl, tetrazolyl, indazolyl, 1,2,4-thiadiazolyl, isothiazolyl, benzothienyl, purinyl, carbazolyl, benzimidazolyl, indolinyl, and the like. The term 5-membered heteroaryl refers to a heteroaryl wherein the number of ring atoms is 5. Nonlimiting examples of 5-membered heteroaryl groups include pyrrolyl, pyrazolyl, oxazolyl, isoxazolyl, thiazolyl, isothiazolyl, oxadiazolyl, thiadiazolyl, furazanyl, imidazolinyl, and triazolyl.

"Heteroarylalkyl" by itself or as part of another substituent refers to an acyclic alkyl group in which one of the hydrogen atoms bonded to a carbon atom, typically a terminal or $sp^3$ carbon atom, is replaced with a heteroaryl group. In one embodiment, the alkyl moiety of the heteroarylalkyl is ($C_1$-$C_6$) alkyl and the heteroaryl moiety is a 5-14-membered heteroaryl. In a more specific embodiment, the alkyl moiety is ($C_1$-$C_3$) alkyl and the heteroaryl moiety is a 5-10 membered heteroaryl.

"Halogen" or "Halo" by themselves or as part of another substituent refers to fluorine, chlorine, bromine and iodine, or fluoro, chloro, bromo and iodo.

As used herein, the terms "contacting" and "reacting" are used as known in the art and generally refer to the bringing together of chemical reagents in such a manner so as to allow their interaction at the molecular level to achieve a chemical or physical transformation. In some embodiments, contacting or reacting involves two (or more) reagents, wherein one or more equivalents of a second reagent are used with respect to a first reagent. The reacting steps of the processes described herein can be conducted for a time and under conditions suitable for preparing the identified product.

"Compound (I)" or "CTP-543" is a deuterated analog of ruxolitinib, known by the chemical name (R)-3-(4-(7H-pyrrolo[2,3-d]pyrimidin-4-yl)-1H-pyrazol-1-yl)-3-(cyclopentyl-2,2,3,3,4,4,5,5-$d_8$)propanenitrile. Compound (I) may also be referred to herein as $D_8$-ruxolitinib. Compound (I) is represented by the following structural formula:

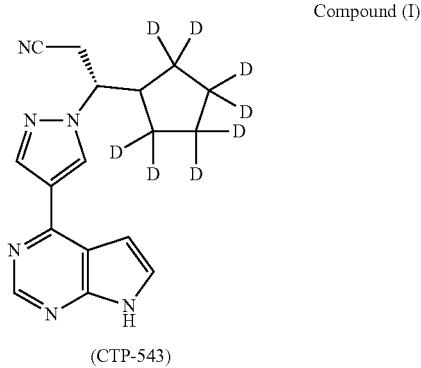 [SMILES: [2H]C1([2H])C([C@@H](CC#N)n2cc(-c3ncnc4[nH]ccc34)cn2)C([2H])([2H])C([2H])([2H])C1([2H])[2H]]

Compound (I)

(CTP-543)

It will be recognized that some variation of natural isotopic abundance occurs in a synthesized compound depending upon the origin of chemical materials used in the synthesis. Thus, a compound disclosed herein will inherently contain small amounts of deuterated isotopologues. The concentration of naturally abundant stable hydrogen and carbon isotopes, notwithstanding this variation, is small and immaterial as compared to the degree of stable isotopic substitution of compounds of this invention. See, for instance, Wada, E et al., Seikagaku, 1994, 66:15; Gannes, L Z et al., Comp Biochem Physiol Mol Integr Physiol, 1998, 119:725.

In the compounds of this invention any atom not specifically designated as a particular isotope is meant to represent any stable isotope of that atom. Unless otherwise stated, when a position is designated specifically as "H" or "hydrogen", the position is understood to have hydrogen at its natural abundance isotopic composition. In some embodiments, when a position is designated specifically as "H" or "hydrogen", the position is at least 90%, at least 95%, at least 96%, at least 97%, at least 98%, or at least 99% hydrogen. In some embodiments, when a position is designated specifically as "H" or "hydrogen", the position incorporates ≤10% deuterium, ≤5% deuterium, ≤4% deuterium, ≤3% deuterium, ≤2% deuterium, or ≤1% deuterium. Also unless otherwise stated, when a position is designated specifically as "D" or "deuterium", the position is understood to have deuterium at an abundance that is at least 3340 times greater than the natural abundance of deuterium, which is 0.015% (i.e., at least 50.1% incorporation of deuterium).

The term "isotopic enrichment factor" as used herein means the ratio between the isotopic abundance and the natural abundance of a specified isotope.

In other embodiments, a compound of this invention has an isotopic enrichment factor for each designated deuterium atom of at least 3500 (52.5% deuterium incorporation at each designated deuterium atom), at least 4000 (60% deuterium incorporation), at least 4500 (67.5% deuterium incorporation), at least 5000 (75% deuterium), at least 5500 (82.5% deuterium incorporation), at least 6000 (90% deuterium incorporation), at least 6333.3 (95% deuterium incorporation), at least 6466.7 (97% deuterium incorporation), at least 6600 (99% deuterium incorporation), or at least 6633.3 (99.5% deuterium incorporation).

In some embodiments, a compound of this invention has deuterium incorporation at each designated deuterium atom of at least 52.5%. In some embodiments, a compound of this invention has deuterium incorporation at each designated deuterium atom at least 60%. In some embodiments, a compound of this invention has deuterium incorporation at each designated deuterium atom of at least 67.5%. In some embodiments, a compound of this invention has deuterium incorporation at each designated deuterium atom of at least 75%. In some embodiments, a compound of this invention has deuterium incorporation at each designated deuterium atom of at least 82.5%. In some embodiments, a compound of this invention has deuterium incorporation at each designated deuterium atom of at least 90%. In some embodiments, a compound of this invention has deuterium incorporation at each designated deuterium atom of at least 95%. In some embodiments, a compound of this invention has deuterium incorporation at each designated deuterium atom of at least 97.5%. In some embodiments, a compound of this invention has deuterium incorporation at each designated deuterium atom of at least 99%. In some embodiments, a compound of this invention has deuterium incorporation at each designated deuterium atom of at least 99.5%.

The term "isotopologue" refers to a species (molecule) in which the chemical structure differs from another species (molecule) of a compound of this invention only in the isotopic composition thereof.

The term "compound," when referring to a compound of this invention, refers to a collection of molecules having an identical chemical structure, except that there may be isotopic variation among the constituent atoms of the molecules. Thus, for example, it will be clear to those of skill in the art that while Compound (I) is represented by a particular chemical structure having deuterium atoms at eight designated positions, Compound (I) will contain molecules having deuterium at each of the eight designated positions, and may also contain isotopologues having hydrogen atoms at one or more of the designated deuterium positions in that structure. The relative amount of such isotopologues in Compound (I) will depend upon a number of factors including the isotopic purity of deuterated reagents used to make the compound and the efficiency of incorporation of deuterium in the various synthesis steps used to prepare the compound.

As used herein, the term "reacting" is used as known in the art and generally refers to the bringing together of chemical reagents in such a manner so as to allow their interaction at the molecular level to achieve a chemical or physical transformation. In some embodiments, the reacting involves two reagents, wherein one or more equivalents of second reagent are used with respect to the first reagent. The reacting steps of the processes described herein can be conducted for a time and under conditions suitable for preparing the identified product.

Preparation of compounds can involve the protection and deprotection of various chemical groups. The need for protection and deprotection, and the selection of appropriate protecting groups can be readily determined by one skilled in the art. The chemistry of protecting groups can be found, for example, in Greene, et al., Protective Groups in Organic Synthesis, 4d. Ed., Wiley & Sons, 2007, which is incorporated herein by reference in its entirety. Thus, for example, a nitrogen atom can be protected as a carbamate, e.g., with a protecting group such as t-butoxycarbonyl (Boc); as a sulfonamide, e.g., with a protecting group such as triflyl (Tf, $SO_2$—$CF_3$); as an amide, e.g., with a protecting group such as acetyl, benzoyl, or trifluoroacetyl ($F_3$—Ac); as an amine, e.g., with a protecting group such as benzyl or trityl (Tr, —$CPh_3$); or as a silyl amine (e.g., with a protecting group such as $SiPh_2Bu^t$). Adjustments to the protecting groups and formation and cleavage methods described herein may be adjusted as necessary in light of the various substituents.

The reactions of the processes described herein can be carried out in suitable solvents which can be readily selected by one of skill in the art of organic synthesis. Suitable solvents can be substantially nonreactive with the starting materials (reactants), the intermediates, or products at the temperatures at which the reactions are carried out, e.g., temperatures which can range from the solvent's freezing temperature to the solvent's boiling temperature. A given reaction can be carried out in one solvent or a mixture of more than one solvent. Depending on the particular reaction step, suitable solvents for a particular reaction step can be selected. In some embodiments, reactions can be carried out in the absence of solvent, such as when at least one of the reagents is a liquid or gas.

Suitable solvents can include halogenated solvents such as carbon tetrachloride, bromodichloromethane, dibromochloromethane, bromoform, chloroform, bromochloromethane, dibromomethane, butyl chloride, dichloromethane (DCM), tetrachloroethylene, trichloroethylene, 1,1,1-trichloroethane, 1,1,2-trichloroethane, 1,1-dichloroethane, 2-chloropropane, α,α,α-trifluorotoluene, 1,2-dichloroethane, 1,2-dibromoethane, hexafluorobenzene, 1,2,4-trichlorobenzene, 1,2-dichlorobenzene, chlorobenzene, fluorobenzene, trifluorotoluene (TFT), and mixtures thereof.

Suitable ether solvents include: dimethoxymethane, tetrahydrofuran (THF), 1,3-dioxane, 1,4-dioxane, furan, diethyl ether, ethylene glycol dimethyl ether, ethylene glycol diethyl ether, diethylene glycol dimethyl ether, diethylene glycol diethyl ether, triethylene glycol dimethyl ether, anisole, t-butyl methyl ether, mixtures thereof. Additional ether solvents include 2-methyltetrahydrofuran and cyclopentyl methyl ether (and mixtures thereof, including with other ether solvents described herein).

Suitable protic solvents can include, by way of example and without limitation, water, methanol (MeOH), ethanol (EtOH), isopropanol (iPrOH), 2-nitroethanol, 2-fluoroethanol, 2,2,2-trifluoroethanol (TFE), ethylene glycol, 1-propanol, 2-propanol, 2-methoxyethanol, 1-butanol, 2-butanol, i-butyl alcohol, t-butyl alcohol, 2-ethoxyethanol, diethylene glycol, 1-, 2-, or 3-pentanol, neo-pentyl alcohol, t-pentyl alcohol, diethylene glycol monomethyl ether, diethylene glycol monoethyl ether, cyclohexanol, benzyl alcohol, phenol, glycerol, hexafluoroisopropanol (HFIP), acetic acid (AcOH), and mixtures thereof.

Suitable aprotic solvents can include, by way of example and without limitation, tetrahydrofuran (THF), N,N-dimethylformamide (DMF), N,N-dimethylacetamide (DMA), 1,3-dimethyl-3,4,5,6-tetrahydro-2(1H)-pyrimidinone (DMPU), 1,3-dimethyl-2-imidazolidinone (DMI), N-methylpyrrolidinone (NMP), formamide, N-methylacetamide, N-methylformamide, acetonitrile, dimethyl sulfoxide (DMSO), propionitrile, ethyl formate, methyl acetate, hexachloroacetone, acetone, ethyl methyl ketone, ethyl acetate (EtOAc), sulfolane, N,N-dimethylpropionamide, tetramethylurea, nitromethane, nitrobenzene, hexamethylphosphoramide, and mixtures thereof.

Suitable hydrocarbon solvents include benzene, cyclohexane, pentane, hexane, toluene, cycloheptane, methylcyclohexane, heptane, ethylbenzene, m-, o-, or p-xylene, octane, indane, nonane, naphthalene, and mixtures thereof.

The reactions of the processes described herein can be carried out at appropriate temperatures which can be readily determined by the skilled artisan. Reaction temperatures will depend on, for example, the melting and boiling points of the reagents and solvent, if present; the thermodynamics of the reaction (e.g., vigorously exothermic reactions may need to be carried out at reduced temperatures); and the kinetics of the reaction (e.g., a high activation energy barrier may need elevated temperatures). "Elevated temperature" refers to temperatures above room temperature (about 22° C.).

The reactions of the processes described herein can be carried out in air or under an inert atmosphere. Typically, reactions containing reagents or products that are substantially reactive with air can be carried out using air-sensitive synthetic techniques that are well known to the skilled artisan.

Examples of acids can be inorganic or organic acids. Non-limiting examples of inorganic acids include hydrochloric acid, hydrobromic acid, sulfuric acid, phosphoric acid, and nitric acid. Non-limiting examples of organic acids include formic acid, acetic acid, propionic acid, butanoic acid, benzoic acid, 4-nitrobenzoic acid, methanesulfonic acid, p-toluenesulfonic acid, benzenesulfonic acid, tartaric acid, trifluoroacetic acid, propiolic acid, butyric acid, 2-butynoic acid, vinyl acetic acid, pentanoic acid, hexanoic acid, heptanoic acid, octanoic acid, nonanoic acid and decanoic acid.

Non-limiting examples of bases include lithium hydroxide, sodium hydroxide, potassium hydroxide, lithium carbonate, sodium carbonate, and potassium carbonate. Some example strong bases include, but are not limited to, hydroxide, alkoxides, metal amides, metal hydrides, metal dialkylamides and arylamines, wherein; alkoxides include lithium, sodium and potassium salts of methyl, ethyl and t-butyl oxides; metal amides include sodium amide, potassium amide and lithium amide; metal hydrides include sodium hydride, potassium hydride and lithium hydride; and metal dialkylamides include sodium and potassium salts of methyl, ethyl, n-propyl, i-propyl, n-butyl, t-butyl, trimethylsilyl and cyclohexyl substituted amides.

Upon carrying out preparation of compounds according to the processes described herein, the usual isolation and purification operations such as concentration, filtration, extraction, solid-phase extraction, recrystallization, chromatography, and the like may be used to isolate the desired products.

In some embodiments, the compounds of the invention, and salts thereof, are substantially isolated. By "substantially isolated" is meant that the compound is at least partially or substantially separated from the environment in which it was formed or detected. Partial separation can include, for example, a composition enriched in the compound of the invention. Substantial separation can include compositions containing at least about 50%, at least about 60%, at least about 70%, at least about 80%, at least about 90%, at least about 95%, at least about 97%, or at least about 99% by weight of the compound of the invention, or salt thereof. Methods for isolating compounds and their salts are routine in the art.

The present invention also includes salt forms of the compounds described herein. A salt of a compound of this invention is formed between an acid and a basic group of the compound, such as an amino functional group, or a base and an acidic group of the compound, such as a carboxyl functional group. According to one embodiment, the compound is a pharmaceutically acceptable acid addition salt. In one embodiment the acid addition salt may be a deuterated acid addition salt.

The term "pharmaceutically acceptable," as used herein, refers to a component that is, within the scope of sound medical judgment, suitable for use in contact with the tissues of humans and other mammals without undue toxicity, irritation, allergic response and the like, and are commensurate with a reasonable benefit/risk ratio. A "pharmaceutically acceptable salt" means any non-toxic salt that, upon administration to a recipient, is capable of providing, either directly or indirectly, a compound of this invention. A "pharmaceutically acceptable counterion" is an ionic portion of a salt that is not toxic when released from the salt upon administration to a recipient.

Acids commonly employed to form pharmaceutically acceptable salts include inorganic acids such as hydrochloric acid, hydrobromic acid, hydroiodic acid, sulfuric acid and phosphoric acid, as well as organic acids such as para-toluenesulfonic acid, salicylic acid, tartaric acid, bitartaric acid, ascorbic acid, maleic acid, besylic acid, fumaric acid, gluconic acid, glucuronic acid, formic acid, glutamic acid, methanesulfonic acid, ethanesulfonic acid, benzenesulfonic acid, lactic acid, oxalic acid, para-bromophenylsulfonic acid, carbonic acid, succinic acid, citric acid, benzoic acid and acetic acid, as well as related inorganic and organic acids. Such pharmaceutically acceptable salts thus include sulfate, pyrosulfate, bisulfate, sulfite, bisulfite, phosphate, monohydrogenphosphate, dihydrogenphosphate, metaphosphate, pyrophosphate, chloride, bromide, iodide, acetate, propionate, decanoate, caprylate, acrylate, formate, isobutyrate, caprate, heptanoate, propiolate, oxalate, malonate, succinate, suberate, sebacate, fumarate, maleate, butyne-1, 4-dioate, hexyne-1,6-dioate, benzoate, chlorobenzoate, methylbenzoate, dinitrobenzoate, hydroxybenzoate, methoxybenzoate, phthalate, terephthalate, sulfonate, xylene sulfonate, phenylacetate, phenylpropionate, phenylbutyrate, citrate, lactate, β-hydroxybutyrate, glycolate, maleate, tartrate, methanesulfonate, propanesulfonate, naphthalene-1-sulfonate, naphthalene-2-sulfonate, mandelate and other salts. In one embodiment, pharmaceutically acceptable acid addition salts include those formed with mineral acids such as hydrochloric acid and hydrobromic acid, and especially those formed with organic acids such as maleic acid. In one embodiment, the acids commonly employed to form pharmaceutically acceptable salts include the above-listed inorganic acids, wherein at least one hydrogen is replaced with deuterium.

The compounds of the present invention may contain an asymmetric carbon atom, for example, as the result of deuterium substitution or otherwise. As such, unless otherwise stated (or illustrated) herein, compounds of this invention can exist as either individual enantiomers, or mixtures of the two enantiomers. Accordingly, a compound of the present invention may exist as either a racemic mixture or a scalemic mixture, or as individual respective stereoisomers that are substantially free from another possible stereoisomer. The term "substantially free of other stereoisomers" as used herein means less than 25% of other stereoisomers, preferably less than 10% of other stereoisomers, more preferably less than 5% of other stereoisomers and most preferably less than 2% of other stereoisomers are present. In certain embodiments, a compound which is substantially free of other stereoisomers has an enantiomeric excess (e.e.) of at least about 90%. In other embodiments, a compound which is substantially free of other stereoisomers has an enantiomeric excess (e.e.) of at least about 95%, 96%, 97%, 98%, 99%, or 99.5%. Methods of obtaining or synthesizing an individual enantiomer for a given compound are known in the art and may be applied as practicable to final compounds or to starting material or intermediates.

Unless otherwise indicated, when a disclosed compound is named or depicted by a structure without specifying the stereochemistry and has one or more chiral centers, it is understood to represent all possible stereoisomers of the compound.

The term "stable compounds," as used herein, refers to compounds which possess stability sufficient to allow for their manufacture and which maintain the integrity of the compound for a sufficient period of time to be useful for the purposes detailed herein (e.g., formulation into therapeutic products, intermediates for use in production of therapeutic compounds, isolatable or storable intermediate compounds, treating a disease or condition responsive to therapeutic agents).

"D" and "d" both refer to deuterium. "Stereoisomer" refers to both enantiomers and diastereomers. "ER" or "er" refers to enantiomeric ratio. "EE" or "ee" refers to enantiomeric excess. "AUC" refers to area under the curve. "Tert" and "t-" each refer to tertiary. "Sec" or "s-" each refer to secondary. "n-" refers to normal. "i-" refers to iso. "US" refers to the United States of America.

"Substituted with deuterium" refers to the replacement of one or more hydrogen atoms with a corresponding number of deuterium atoms. Throughout this specification, a variable may be referred to generally (e.g., "each R") or may be referred to specifically (e.g., $R^1$, $R^2$, $R^3$, etc.). Unless otherwise indicated, when a variable is referred to generally, it is meant to include all specific embodiments of that particular variable.

Compounds

In one aspect, the invention provides compounds and intermediates useful for preparing ruxolitinib and deuterated analogs of ruxolitinib.

In certain embodiments, the invention provides a compound of any one of Formula II, II', III. III', V, V', VIII, VIII', IX, IX', XI, or XI' as described herein; or a salt thereof.

In certain embodiments, the invention provides a compound of Formula II',

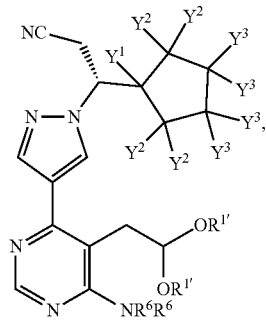

or a salt thereof,
in which each $Y^1$ is hydrogen or deuterium; each $Y^2$ is the same and is hydrogen or deuterium; each $Y^3$ is the same and is hydrogen or deuterium; each $R^{1'}$ is $C_1$-$C_{10}$ alkyl (e.g., methyl or ethyl), or $C_2$-$C_{10}$ alkenyl (e.g., allyl), or the two $R^{1'}$s, taken together with the oxygen atoms to which they are attached, form a 5-7-membered heterocyclic ring which may optionally be substituted (e.g., a 1,3-dioxolan-2-yl ring, or a 1,3-dioxan-2-yl ring, or a 1,3-benzodioxolan-2-yl ring); and each $R^6$ is independently selected from H and a protecting group.

In certain embodiments: each $R^{1'}$ is methyl or ethyl; and one $R^6$ is H and the other is a protecting group. In certain embodiments, $Y^1$ is hydrogen. In certain embodiments, each $Y^2$ is the same and is deuterium; and each $Y^3$ is the same and is deuterium. In other embodiments, each $Y^2$ is the same and is hydrogen; and each $Y^3$ is the same and is hydrogen. In certain embodiments, each $R^{1'}$ is methyl. In certain embodiments, each $R^{1'}$ is ethyl. In certain embodiments, each $R^6$ is H. In certain embodiments, one $R^6$ is H and the other $R^6$ is a protecting group. In certain embodiments, the protecting group is a Boc group.

In certain embodiments, the invention provides a compound of Formula II:

Formula II

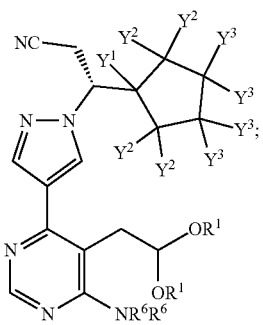

or a salt thereof,
wherein $Y^1$ is hydrogen or deuterium, each $Y^2$ is the same and is hydrogen or deuterium, and each $Y^3$ is the same and is hydrogen or deuterium; and wherein each $R^1$ is $C_1$-$C_6$ alkyl, or taken together the two $R^1$s form a $C_2$ or $C_3$ alkylene moiety; and each $R^6$ is independently selected from H or a protecting group. In certain embodiments, $Y^1$ is hydrogen. In certain embodiments, each $Y^2$ is the same and is deuterium; and each $Y^3$ is the same and is deuterium. In other embodiments, each $Y^2$ is the same and is hydrogen; and each $Y^3$ is the same and is hydrogen. In certain embodiments, each $R^1$ is methyl. In certain embodiments, each $R^1$ is ethyl. In certain embodiments, each $R^6$ is H. In certain embodiments, one $R^6$ is H and the other $R^6$ is a protecting group. In certain embodiments, the protecting group is a Boc group.

In certain embodiments, the invention provides a compound of Formula III':

Formula III'

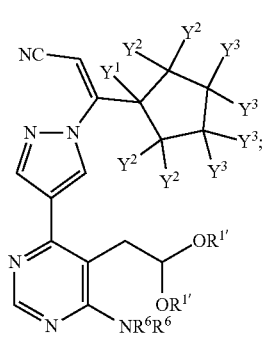

or a salt thereof;
wherein $Y^1$ is hydrogen or deuterium; each $Y^2$ is the same and is hydrogen or deuterium; each $Y^3$ is the same and is hydrogen or deuterium; each $R^{1'}$ is $C_1$-$C_{10}$ alkyl (e.g., methyl or ethyl), or $C_2$-$C_{10}$ alkenyl (e.g., allyl), or the two $R^{1'}$s, taken together with the oxygen atoms to which they are attached, form a 5-7-membered heterocyclic ring which may optionally be substituted (e.g., a 1,3-dioxolan-2-yl ring, or a 1,3-dioxan-2-yl ring, or a 1,3-benzodioxolan-2-yl ring); and each $R^6$ is independently selected from H and a protecting group. In certain embodiments, $Y^1$ is hydrogen; each $Y^2$ is the same and is hydrogen; and each $Y^3$ is the same and is hydrogen. In other embodiments, $Y^1$ is deuterium; each $Y^2$ is the same and is deuterium; and each $Y^3$ is the same and is deuterium. In certain embodiments, each $R^{1'}$ is $C_1$-$C_{10}$ alkyl; in further embodiments, each $R^{1'}$ is methyl or ethyl. In certain embodiments, each $R^6$ is H. In certain embodiments, one $R^6$ is H and one $R^6$ is a protecting group. In certain embodiments, each $R^6$ is a protecting group. In certain embodiments, the protecting group is a t-butoxycarbonyl group.

In certain embodiments, the invention provides a compound of Formula III:

Formula III

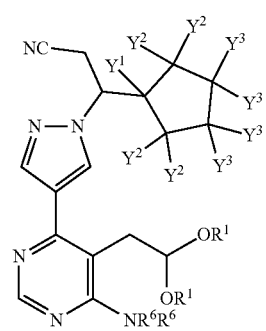

or a salt thereof,
wherein each of $Y^1$, $Y^2$, $Y^3$, $R^1$, and $R^6$ are as defined as in Formula II. In certain embodiments, $Y^1$ is hydrogen. In certain embodiments, each $Y^2$ is the same and is deuterium; and each $Y^3$ is the same and is deuterium. In other embodiments, each $Y^2$ is the same and is hydrogen; and each $Y^3$ is the same and is hydrogen. In certain embodiments, each $R^1$ is methyl. In certain embodiments, each $R^1$ is ethyl. In certain embodiments, each $R^6$ is H. In certain embodiments, one $R^6$ is H and the other $R^6$ is a protecting group. In certain embodiments, the protecting group is a Boc group. $Y^3$ is deuterium.

In certain embodiments, the invention provides a compound of Formula VII:

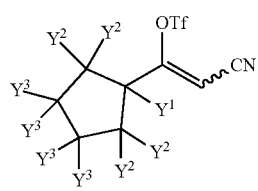

Formula VII wherein $Y^1$ is hydrogen or deuterium; each $Y^2$ is the same and is hydrogen or deuterium; each $Y^3$ is the same and is hydrogen or deuterium. In certain embodiments, $Y^1$ is hydrogen. In certain embodiments, each $Y^2$ is the same and is hydrogen. In certain embodiments, each $Y^2$ is the same and is deuterium. In certain embodiments, each $Y^3$ is the same and is hydrogen. In certain embodiments, each $Y^3$ is the same and is deuterium. In certain embodiments, each $Y^2$ and $Y^3$ is hydrogen. In certain embodiments, each $Y^2$ and $Y^3$ is deuterium. In one embodiment, $Y^1$ is hydrogen and each $Y^2$ and $Y^3$ is hydrogen. In another embodiment, $Y^1$ is hydrogen and each $Y^2$ and $Y^3$ is deuterium.

In another embodiment, the invention provides a compound of Formula VIII':

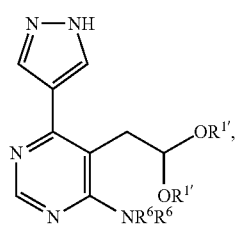

Formula VIII' wherein each $R^{1'}$ is $C_1$-$C_{10}$ alkyl (e.g., methyl or ethyl), or $C_2$-$C_{10}$ alkenyl (e.g., allyl), or the two $R^{1'}$'s, taken together with the oxygen atoms to which they are attached, form a 5-7-membered heterocyclic ring which may optionally be substituted (e.g., a 1,3-dioxolan-2-yl ring, or a 1,3-dioxan-2-yl ring, or a 1,3-benzodioxolan-2-yl ring); and each $R^6$ is independently selected from H and a protecting group. In certain embodiments, $Y^1$ is hydrogen; each $Y^2$ is the same and is hydrogen; and each $Y^3$ is the same and is hydrogen. In other embodiments, $Y^1$ is deuterium; each $Y^2$ is the same and is deuterium; and each $Y^3$ is the same and is deuterium. In certain embodiments, each $R^{1'}$ is $C_1$-$C_{10}$ alkyl; in further embodiments, each $R^{1'}$ is methyl or ethyl. In certain embodiments, each $R^6$ is H. In certain embodiments, one $R^6$ is H and one $R^6$ is a protecting group. In certain embodiments, each $R^6$ is a protecting group. In certain embodiments, the protecting group is a t-butoxycarbonyl group.

In another embodiment, the invention provides a compound of Formula VIII:

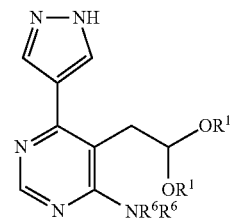

Formula VIII or a salt thereof;

wherein $R^1$ and $R^6$ are as defined for Compound II. In certain embodiments, $Y^1$ is hydrogen. In certain embodiments, each $Y^2$ is the same and is deuterium; and each $Y^3$ is the same and is deuterium. In other embodiments, each $Y^2$ is the same and is hydrogen; and each $Y^3$ is the same and is hydrogen. In certain embodiments, each $R^1$ is methyl. In certain embodiments, each $R^1$ is ethyl. In certain embodiments, each $R^6$ is H. In certain embodiments, one $R^6$ is H and the other $R^6$ is a protecting group. In certain embodiments, the protecting group is a Boc group.

In still another embodiment, the invention provides a compound of Formula XI:

or a salt thereof;

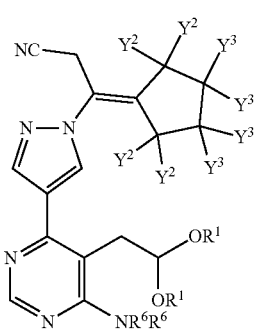

Formula XI or a salt thereof, wherein each of $Y^2$, $Y^3$, $R^1$, and $R^6$ are defined as in Formula II. In certain embodiments, $Y^1$ is hydrogen. In certain embodiments, each $Y^2$ is the same and is deuterium; and each $Y^3$ is the same and is deuterium. In other embodiments, each $Y^2$ is the same and is hydrogen; and each $Y^3$ is the same and is hydrogen. In certain embodiments, each $R^1$ is methyl. In certain embodiments, each $R^1$ is ethyl. In certain embodiments, each $R^6$ is H. In certain embodiments, one $R^6$ is H and the other $R^6$ is a protecting group. In certain embodiments, the protecting group is a Boc group.

In another embodiment, the invention provides a compound of Formula XI':

or a salt thereof;

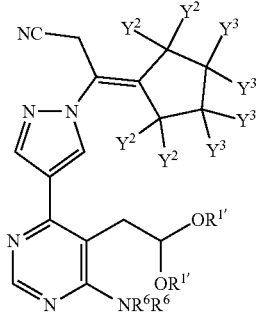

Formula XI' or a salt thereof,
wherein each of Y², Y³, R¹, and R⁶ are as defined as in Formula II'. In certain embodiments, Y¹ is hydrogen. In certain embodiments, each Y² is the same and is deuterium; and each Y³ is the same and is deuterium. In other embodiments, each Y² is the same and is hydrogen; and each Y³ is the same and is hydrogen. In certain embodiments, each R¹' is methyl. In certain embodiments, each R¹' is ethyl. In certain embodiments, each R⁶ is H. In certain embodiments, one R⁶ is H and the other R⁶ is a protecting group. In certain embodiments, the protecting group is a Boc group.

In one embodiment, the invention provides a compound represented by the structure:

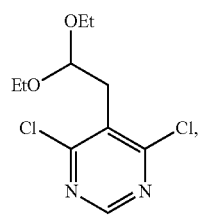 [SMILES: CCOC(Cc1c(Cl)ncnc1Cl)OCC]

or a salt thereof.

In another embodiment, the invention provides a compound represented by the structure:

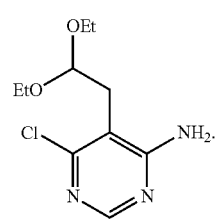

In another embodiment, the invention provides a compound represented by the structure:

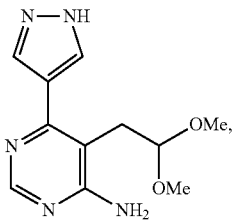

or a salt thereof.

In another embodiment, the invention provides a compound represented by the structure:

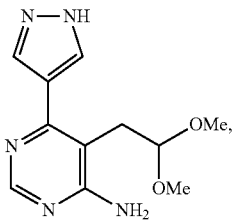

In another embodiment, the invention provides a compound represented by the structure:

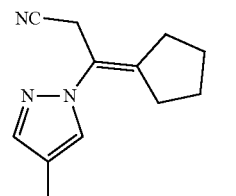

or a salt thereof.

In another embodiment, the invention provides a compound represented by the structure:

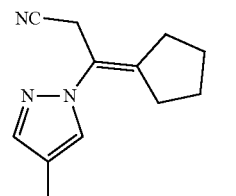

or a salt thereof.

In another embodiment, the invention provides a compound represented by the structure:

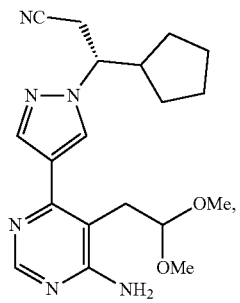 [SMILES: COC(Cc1c(N)ncnc1-c1cnn([C@H](CC#N)C2CCCC2)c1)OC]

or a salt thereof.

In another embodiment, the invention provides a compound represented by the structure:

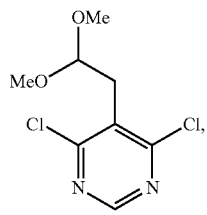 [SMILES: COC(Cc1c(Cl)ncnc1Cl)OC]

or a salt thereof.

In another embodiment, the invention provides a compound represented by the structure:

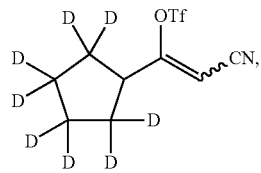

or a salt thereof.

In another embodiment, the invention provides a compound represented by the structure:

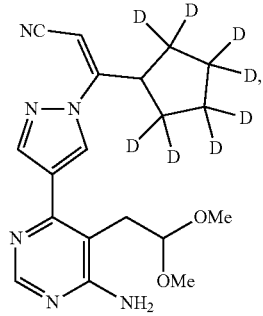

or a salt thereof.

In another embodiment, the invention provides a compound represented by the structure:

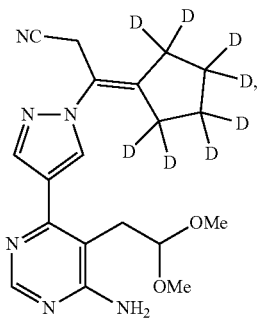

or a salt thereof.

In another embodiment, the invention provides a compound represented by the structure:

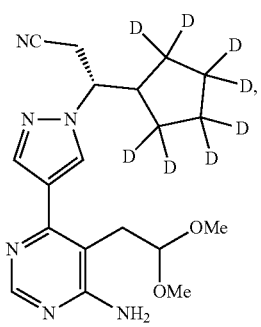

or a salt thereof.

In another embodiment, the invention provides a compound represented by the structure:

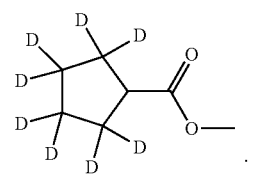 [SMILES: [2H]C1([2H])C(C(=O)OC)C([2H])([2H])C([2H])([2H])C1([2H])[2H]]

In another embodiment, the invention provides a compound represented by the structure:

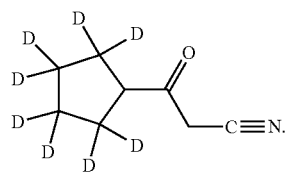

In another embodiment, the invention provides a compound represented by the structure:

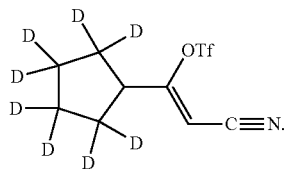 [SMILES: [2H]C1([2H])C(/C(=C/C#N)OS(=O)(=O)C(F)(F)F)C([2H])([2H])C([2H])([2H])C1([2H])[2H]]

In another embodiment, the invention provides a compound represented by the structure:

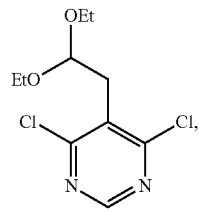

or a salt thereof.

In another embodiment, the invention provides a compound represented by the structure:

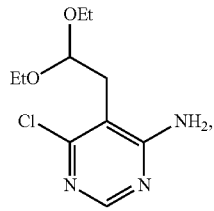

or a salt thereof.

In another embodiment, the invention provides a compound represented by the structure:

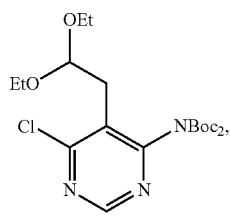

or a salt thereof.

In another embodiment, the invention provides a compound represented by the structure:

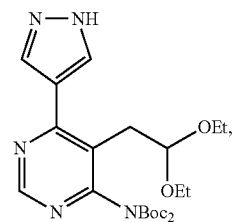

or a salt thereof.

In another embodiment, the invention provides a compound represented by the structure:

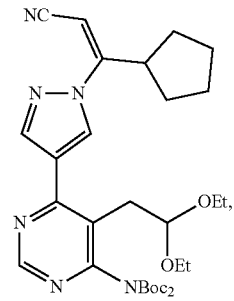

or a salt thereof.

In another embodiment, the invention provides a compound represented by the structure:

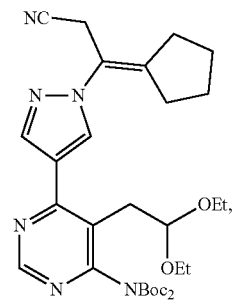

or a salt thereof.

In another embodiment, the invention provides a compound represented by the structure:

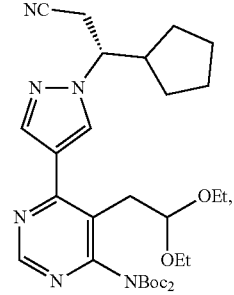

or a salt thereof.

In another embodiment, the invention provides a compound represented by the structure:

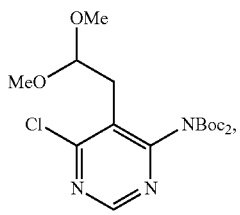

or a salt thereof.

In another embodiment, the invention provides a compound represented by the structure:

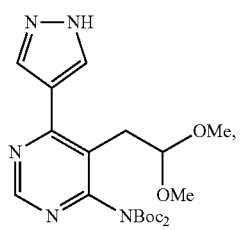

or a salt thereof.

In another embodiment, the invention provides a compound represented by the structure:

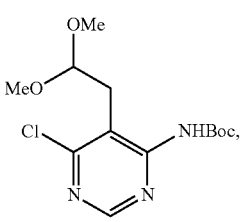 [SMILES: COC(Cc1c(Cl)ncnc1NC(=O)OC(C)(C)C)OC]

or a salt thereof.

In another embodiment, the invention provides a compound represented by the structure:

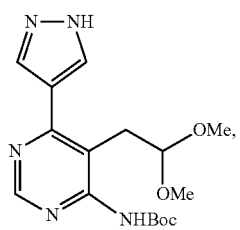 [SMILES: COC(Cc1c(NC(=O)OC(C)(C)C)ncnc1-c1cn[nH]c1)OC]

or a salt thereof.

In another embodiment, the invention provides a compound represented by the structure:

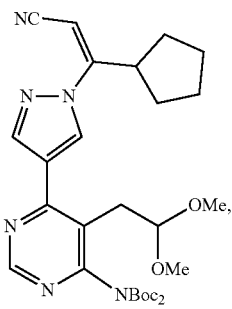

or a salt thereof.

In another embodiment, the invention provides a compound represented by the structure:

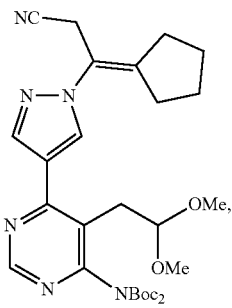

or a salt thereof.

In another embodiment, the invention provides a compound represented by the structure:

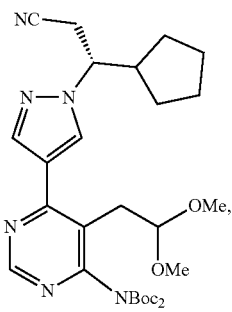

or a salt thereof.

In another embodiment, the invention provides a compound represented by the structure:

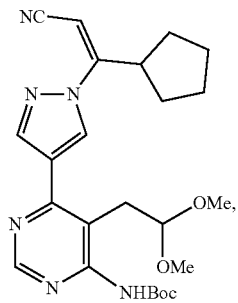 [SMILES: COC(Cc1c(NC(=O)OC(C)(C)C)ncnc1-c1cnn(/C(=C\C#N)C2CCCC2)c1)OC]

or a salt thereof.

In another embodiment, the invention provides a compound represented by the structure:

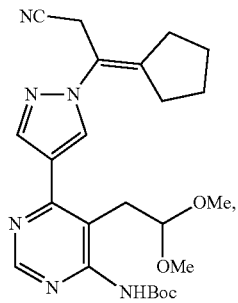 [SMILES: COC(Cc1c(NC(=O)OC(C)(C)C)ncnc1-c1cnn(C(CC#N)=C2CCCC2)c1)OC]

or a salt thereof.

In another embodiment, the invention provides a compound represented by the structure:

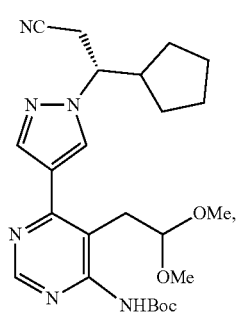 [SMILES: COC(Cc1c(NC(=O)OC(C)(C)C)ncnc1-c1cnn([C@H](CC#N)C2CCCC2)c1)OC]

or a salt thereof.

In still another embodiment, the invention provides a compound of Formula I (e.g., a compound of Formula I prepared by any method disclosed herein) for use in the manufacture of a medicament for the treatment of a JAK1- or JAK2-related disorder, including alopecia areata.

Processes

In one aspect, the invention provides a process for preparing ruxolitinib. In certain embodiments, the method comprises the steps shown below:

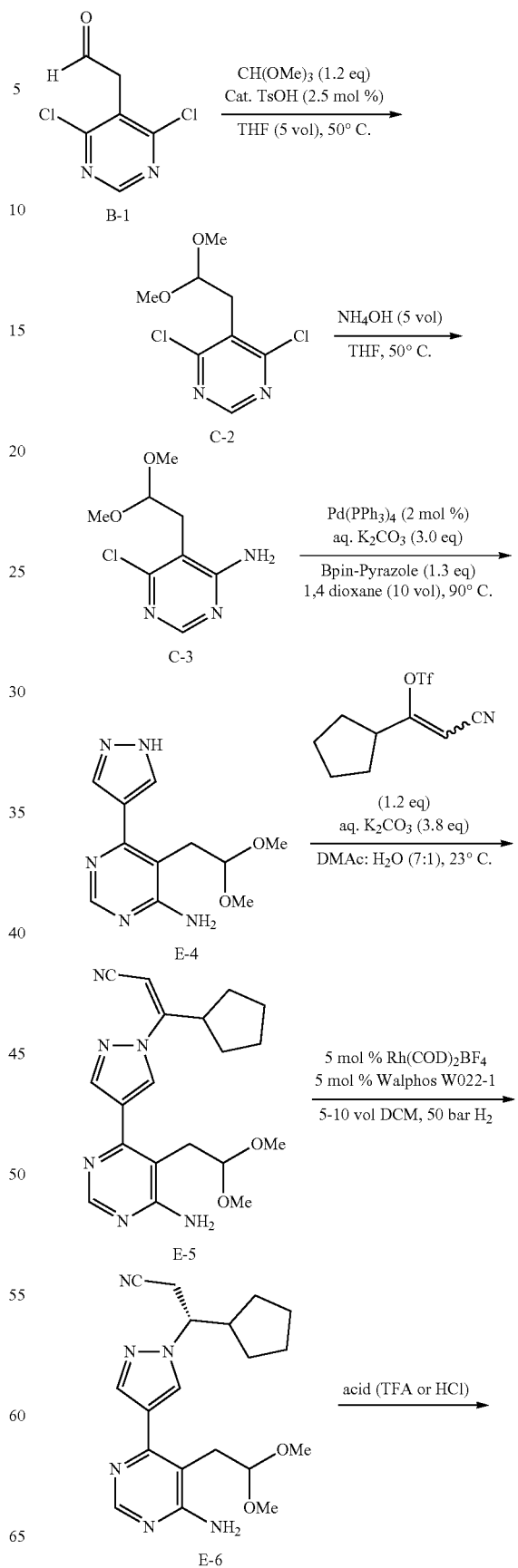

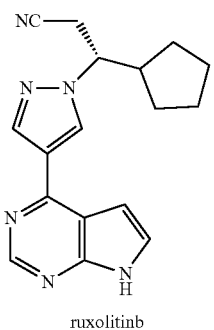

ruxolitnb

In one aspect, a method for preparing ruxolitinib, or a salt thereof, comprises the step of reacting a compound represented by the formula E-6, or a salt thereof, in the presence of an acid under conditions such that ruxolitinib, or a salt thereof, is formed. In certain embodiments, the compound represented by the formula E-6, or a salt thereof, is the D-DBTA salt. In certain embodiments, when the compound represented by the formula E-6, or a salt thereof, is a salt, the method includes the further step of contacting the salt of the compound represented by the formula E-6 with a base prior to the step of reacting in the presence of an acid. In certain embodiments, the acid is trifluoroacetic acid or hydrochloric acid (HCl); in certain embodiments, the acid is HCl. In certain embodiments, the acid is present in molar excess relative to the compound represented by the formula E-6 or salt thereof. In certain embodiments, the step of reacting the compound represented by the formula E-6, or a salt thereof, in the presence of an acid is performed in a solvent. In certain embodiments, the solvent is an aprotic solvent; in certain embodiments, the solvent is toluene. In certain embodiments, the solvent is a mixture of solvents, e.g., a mixture of an aprotic solvent, such as toluene, and an alcoholic solvent, such as isopropanol. In one embodiment, the solvent is a mixture of toluene and isopropanol. In certain embodiments, the acid is provided in an aqueous solvent, and the step of reacting the compound represented by the formula E-6, or a salt thereof, in the presence of the acid is performed in a biphasic reaction mixture. In certain embodiments, the step of reacting the compound represented by the formula E-6, or a salt thereof, in the presence of the acid is performed at a temperature in the range of 15-40° C., e.g., at about 25° C. In certain embodiments, the method comprises, after the step of reacting the compound represented by the formula E-6, or a salt thereof, in the presence of the acid, the additional step of contacting the ruxolitinib, or a salt thereof, with a base, such as an inorganic base, such as potassium phosphate. In certain embodiments, the base is provided in an aqueous solvent, and the step of reacting the compound represented by the formula E-6, or a salt thereof, in the presence of the acid is performed in a biphasic reaction mixture. In certain embodiments, the method further comprises, after the step of contacting the ruxolitinib, or a salt thereof, with a base, the further step of contacting the ruxolitinib with a second acid, such as phosphoric acid, to provide a salt of ruxolitinib, such as the phosphate salt. In certain embodiments, the step of contacting the ruxolitinib with a second acid comprises contacting ruxolitinib with 85% phosphoric acid, optionally in a solvent, such as isopropanol or an isopropanol/water mixture.

In another aspect, the invention provides a process for preparing CTP-543, or a pharmaceutically acceptable salt thereof. In certain embodiments, the method comprises the steps shown below:

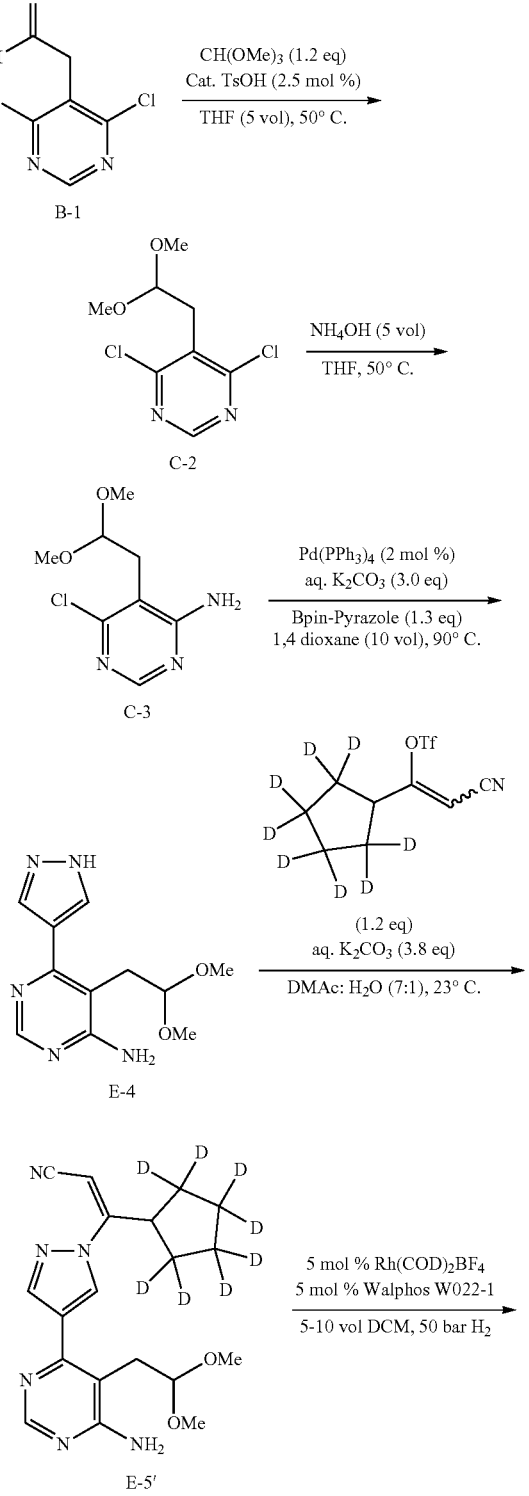

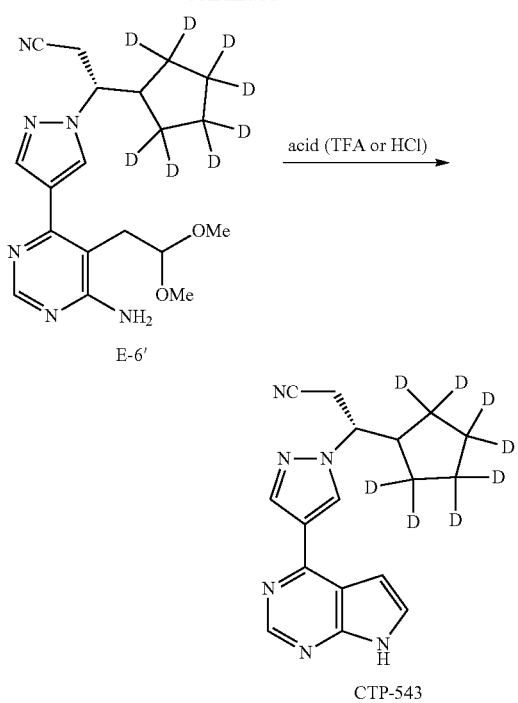

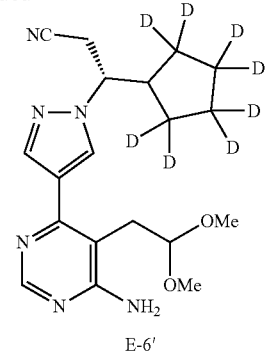

Treatment of CTP-543 produced by the above process with phosphoric acid (H$_3$PO$_4$) produces the phosphate salt of CTP-543. In certain embodiments, E-5' is converted to E-6' through intermediate E-7' (an exemplary embodiment is shown):

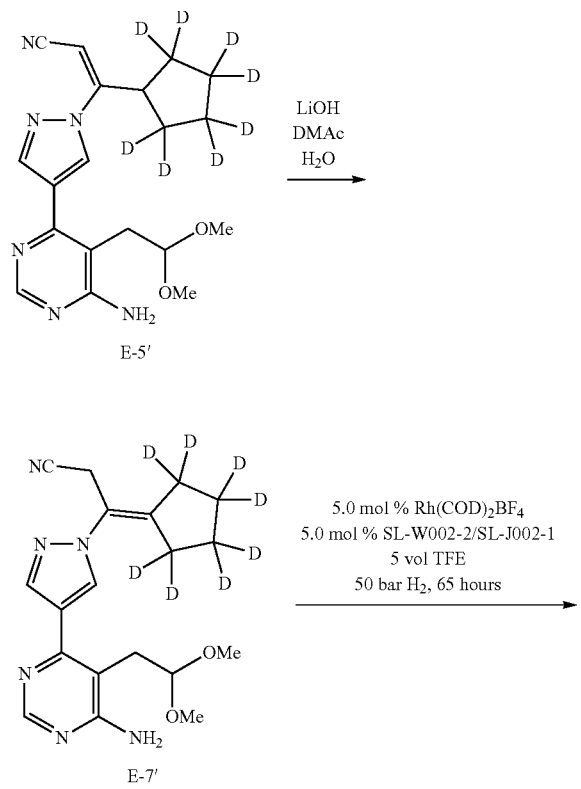

In one aspect, a method for preparing CTP-543, or a salt thereof, comprises the step of reacting a compound represented by the formula E-6', or a salt thereof, in the presence of an acid under conditions such that CTP-543, or a salt thereof, is formed. In certain embodiments, the compound represented by the formula E-6', or a salt thereof, is the D-DBTA salt. In certain embodiments, when the compound represented by the formula E-6', or a salt thereof, is a salt, the method includes the further step of contacting the salt of the compound represented by the formula E-6' with a base prior to the step of reacting in the presence of an acid. In certain embodiments, the acid is trifluoroacetic acid or hydrochloric acid (HCl); in certain embodiments, the acid is HCl. In certain embodiments, the acid is present in molar excess relative to the compound represented by the formula E-6', or salt thereof. In certain embodiments, the step of reacting the compound represented by the formula E-6', or a salt thereof, in the presence of an acid is performed in a solvent. In certain embodiments, the solvent is an aprotic solvent; in certain embodiments, the solvent is toluene. In certain embodiments, the solvent is a mixture of solvents, e.g., a mixture of an aprotic solvent, such as toluene, and an alcoholic solvent, such as isopropanol. In one embodiment, the solvent is a mixture of toluene and isopropanol. In certain embodiments, the acid is provided in an aqueous solvent, and the step of reacting the compound represented by the formula E-6', or a salt thereof, in the presence of the acid is performed in a biphasic reaction mixture. In certain embodiments, the step of reacting the compound represented by the formula E-6', or a salt thereof, in the presence of the acid is performed at a temperature in the range of 15-40° C., e.g., at about 25° C. In certain embodiments, the method comprises, after the step of reacting the compound represented by the formula E-6', or a salt thereof, in the presence of the acid, the additional step of contacting the CTP-543, or a salt thereof, with a base, such as an inorganic base, such as potassium phosphate. In certain embodiments, the method further comprises, after the step of contacting the CTP-543, or a salt thereof, with a base, the further step of contacting the CTP-543 with a second acid, such as phosphoric acid, to provide a salt of CTP-543, such as the phosphate salt. In certain embodiments, the step of contacting the CTP-543 with a second acid comprises contacting CTP-543 with 85% phosphoric acid, optionally in a solvent, such as isopropanol or an isopropanol/water mixture.

In another aspect, the invention provides CTP-543, or a salt thereof, prepared by a process shown above, or by any process disclosed herein that produces CTP-543, or a salt thereof, or a compound of Formula I.

In another aspect, the invention provides a method for preparing a compound of Formula I:

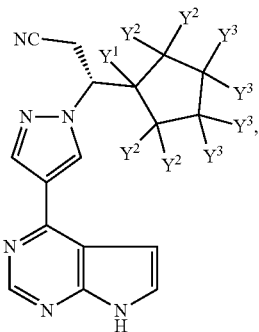

Formula I or a salt thereof;
wherein $Y^1$ is hydrogen or deuterium, each $Y^2$ is the same and is hydrogen or deuterium, and each $Y^3$ is the same and is hydrogen or deuterium;
the method comprising reacting a compound of Formula II:

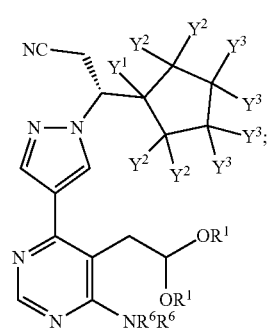

Formula II or a salt thereof
wherein
$Y^1$ is hydrogen or deuterium, each $Y^2$ is the same and is hydrogen or deuterium, and each $Y^3$ is the same and is hydrogen or deuterium; and
each $R^1$ is $C_1$-$C_6$ alkyl, or taken the two $R^1$s together form a $C_2$ or $C_3$ alkylene moiety; and
each $R^6$ is independently selected from H or a protecting group;
under conditions such that a compound of Formula I is formed.

In certain embodiments, each $Y^1$, $Y^2$ and $Y^3$ is deuterium. In certain embodiments, $Y^1$ is hydrogen and each $Y^2$ and $Y^3$ is deuterium. In certain embodiments, $Y^1$ is hydrogen and each $Y^2$ and $Y^3$ is hydrogen. In certain embodiments, the step of reacting comprises reacting the compound of Formula II, or a salt thereof, in the presence of an acid. In certain embodiments, the acid is selected from trifluoroacetic acid (TFA), phosphoric acid, trifluoroacetic anhydride (TFAA), or a combination thereof. In certain embodiments, the acid is selected from trifluoroacetic acid (TFA), phosphoric acid, hydrochloric acid, or a combination thereof. In certain embodiments, the acid is hydrochloric acid.

In certain embodiments, the compound of Formula II, or a salt thereof, is the D-DBTA salt. In certain embodiments, when the compound of Formula II, or a salt thereof, is a salt, the method includes the further step of contacting the salt of the compound of Formula II with a base prior to the step of reacting in the presence of an acid. In certain embodiments, the acid is trifluoroacetic acid or hydrochloric acid (HCl); in certain embodiments, the acid is HCl. In certain embodiments, the acid is present in molar excess relative to the compound of Formula II or salt thereof. In certain embodiments, the step of reacting the compound of Formula II, or a salt thereof, in the presence of an acid is performed in a solvent. In certain embodiments, the solvent is an aprotic solvent; in certain embodiments, the solvent is toluene. In certain embodiments, the solvent is a mixture of solvents, e.g., a mixture of an aprotic solvent, such as toluene, and an alcoholic solvent, such as isopropanol. In one embodiment, the solvent is a mixture of toluene and isopropanol. In certain embodiments, the acid is provided in an aqueous solvent, and the step of reacting the compound of Formula II, or a salt thereof, in the presence of the acid is performed in a biphasic reaction mixture. In certain embodiments, the step of reacting the compound of Formula II, or a salt thereof, in the presence of the acid is performed at a temperature in the range of 15-40° C., e.g., at about 25° C. In certain embodiments, the method comprises, after the step of reacting the compound of Formula II, or a salt thereof, in the presence of the acid, the additional step of contacting the ruxolitinib, or a salt thereof, with a base, such as an inorganic base, such as potassium phosphate. In certain embodiments, the base is provided in an aqueous solvent, and the step of reacting the compound of Formula II, or a salt thereof, in the presence of the acid is performed in a biphasic reaction mixture. In certain embodiments, the method further comprises, after the step of contacting the ruxolitinib, or a salt thereof, with a base, the further step of contacting the ruxolitinib with a second acid, such as phosphoric acid, to provide a salt of ruxolitinib, such as the phosphate salt. In certain embodiments, the step of contacting the ruxolitinib with a second acid comprises contacting ruxolitinib with 85% phosphoric acid, optionally in a solvent, such as isopropanol.

In one aspect, the invention provides a process for preparing a compound of Formula I:

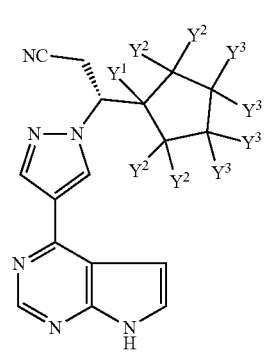

Formula I or a salt thereof,
the process comprising reacting a compound of Formula II':

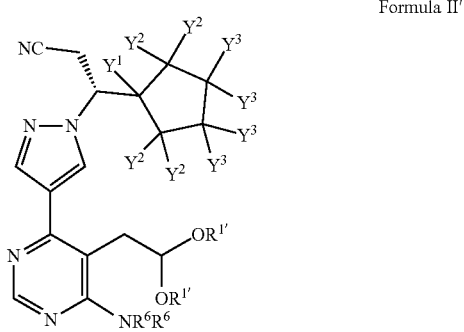

Formula II' or a salt thereof, in the presence of an acid such that a compound of Formula I is formed; wherein in Formula I and Formula II', $Y^1$ is hydrogen or deuterium; each $Y^2$ is the same and is hydrogen or deuterium; each $Y^3$ is the same and is hydrogen or deuterium; and in Formula II', each $R^{1'}$ is $C_1$-$C_{10}$ alkyl (e.g., methyl or ethyl), or $C_2$-$C_{10}$ alkenyl (e.g., allyl), or the two $R^{1'}$s, taken together with the oxygen atoms to which they are attached, form a 5-7-membered heterocyclic ring which may optionally be substituted (e.g., a 1,3-dioxolan-2-yl ring, or a 1,3-dioxan-2-yl ring, or a 1,3-benzodioxolan-2-yl ring); and each $R^6$ is independently selected from H and a protecting group. In certain embodiments, the acid is selected from hydrochloric acid, trifluoroacetic acid (TFA), phosphoric acid, or a combination thereof. In certain embodiments, $Y^1$ is hydrogen; each $Y^2$ is the same and is hydrogen; and each $Y^3$ is the same and is hydrogen. In other embodiments, $Y^1$ is deuterium; each $Y^2$ is the same and is deuterium; and each $Y^3$ is the same and is deuterium. In certain embodiments, each $R^{1'}$ is $C_1$-$C_{10}$ alkyl; in further embodiments, each $R^{1'}$ is methyl or ethyl. In certain embodiments, each $R^6$ is H. In certain embodiments, one $R^6$ is H and one $R^6$ is a protecting group. In certain embodiments, each $R^6$ is a protecting group. In certain embodiments, the protecting group is a t-butoxycarbonyl group.

In certain embodiments, the compound of Formula II', or a salt thereof, is the D-DBTA salt. In certain embodiments, when the compound of Formula II', or a salt thereof, is a salt, the method includes the further step of contacting the salt of the compound of Formula II' with a base prior to the step of reacting in the presence of an acid. In certain embodiments, the acid is trifluoroacetic acid or hydrochloric acid (HCl); in certain embodiments, the acid is HCl. In certain embodiments, the acid is present in molar excess relative to the compound of Formula II' or salt thereof. In certain embodiments, the step of reacting the compound of Formula II', or a salt thereof, in the presence of an acid is performed in a solvent. In certain embodiments, the solvent is an aprotic solvent; in certain embodiments, the solvent is toluene. In certain embodiments, the solvent is a mixture of solvents, e.g., a mixture of an aprotic solvent, such as toluene, and an alcoholic solvent, such as isopropanol. In one embodiment, the solvent is a mixture of toluene and isopropanol. In certain embodiments, the acid is provided in an aqueous solvent, and the step of reacting the compound of Formula II', or a salt thereof, in the presence of the acid is performed in a biphasic reaction mixture. In certain embodiments, the step of reacting the compound of Formula II', or a salt thereof, in the presence of the acid is performed at a temperature in the range of 15-40° C., e.g., at about 25° C. In certain embodiments, the method comprises, after the step of reacting the compound of Formula II', or a salt thereof, in the presence of the acid, the additional step of contacting the ruxolitinib, or a salt thereof, with a base, such as an inorganic base, such as potassium phosphate. In certain embodiments, the base is provided in an aqueous solvent, and the step of reacting the compound of Formula II', or a salt thereof, in the presence of the acid is performed in a biphasic reaction mixture. In certain embodiments, the method further comprises, after the step of contacting the ruxolitinib, or a salt thereof, with a base, the further step of contacting the ruxolitinib with a second acid, such as phosphoric acid, to provide a salt of ruxolitinib, such as the phosphate salt. In certain embodiments, the step of contacting the ruxolitinib with a second acid comprises contacting ruxolitinib with 85% phosphoric acid, optionally in a solvent, such as isopropanol.

In another aspect, the invention provides a method for preparing a compound of Formula II:

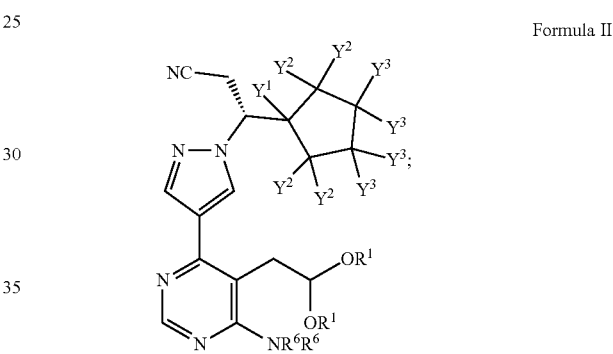

Formula II or a salt thereof
wherein
  $Y^1$ is hydrogen or deuterium;
  each $Y^2$ is the same and is hydrogen or deuterium;
  each $Y^3$ is the same and is hydrogen or deuterium; and
  each $R^1$ is $C_1$-$C_6$ alkyl, or taken the two $R^1$s together form a $C_2$ or $C_3$ alkylene moiety; and each $R^6$ is independently selected from H or a protecting group;
the method comprising reacting a compound of Formula III:

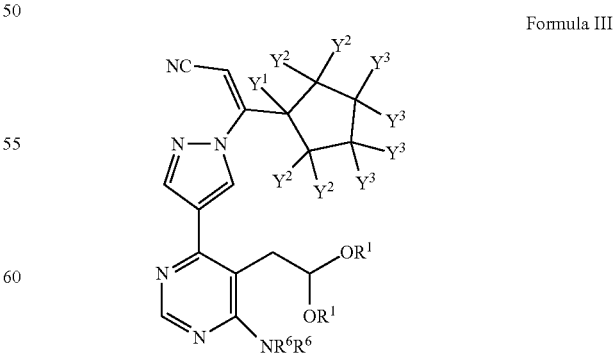

Formula III or a salt thereof, wherein each of $Y^1$, $Y^2$, $Y^3$, $R^1$, and $R^6$ are as defined as in Formula II, with hydrogen gas in the presence of a hydrogenation catalyst.

In another aspect, the invention provides a process for preparing a compound of Formula II:

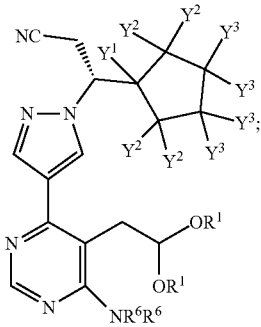

Formula II or a salt thereof,
wherein
$Y^1$ is hydrogen or deuterium;
each $Y^2$ is the same and is hydrogen or deuterium;
each $Y^3$ is the same and is hydrogen or deuterium; and
each $R^1$ is $C_1$-$C_6$ alkyl, or taken the two $R^1$s together form a $C_2$ or $C_3$ alkylene moiety; and each $R^6$ is independently selected from H or a protecting group;
the method comprising reacting a compound of Formula XI:

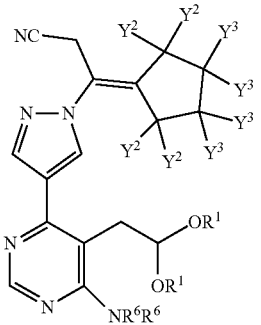

Formula XI or a salt thereof,
wherein each of $Y^2$, $Y^3$, $R^1$, and $R^6$ are as defined as in Formula II, with hydrogen gas in the presence of a hydrogenation catalyst.

In another aspect, the invention provides a process for preparing a compound of Formula II':

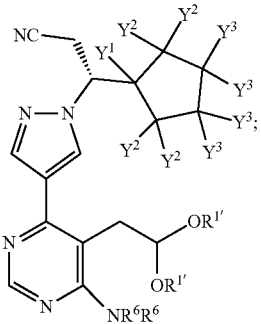

Formula II' or a salt thereof,
wherein
$Y^1$ is hydrogen or deuterium; each $Y^2$ is the same and is hydrogen or deuterium; each $Y^3$ is the same and is hydrogen or deuterium; each $R^{1'}$ is $C_1$-$C_{10}$ alkyl (e.g., methyl or ethyl), or $C_2$-$C_{10}$ alkenyl (e.g., allyl), or the two $R^{1'}$s, taken together with the oxygen atoms to which they are attached, form a 5-7-membered heterocyclic ring which may optionally be substituted (e.g., a 1,3-dioxolan-2-yl ring, or a 1,3-dioxan-2-yl ring, or a 1,3-benzodioxolan-2-yl ring, each optionally substituted with, e.g., one or more methyl groups); and each $R^6$ is independently selected from H and a protecting group;
the method comprising reacting a compound of Formula XI':

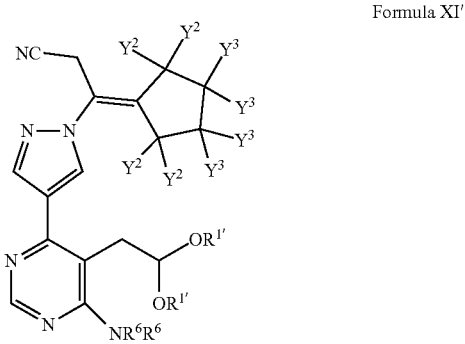

Formula XI' or a salt thereof,
wherein each of $Y^2$, $Y^3$, $R^1$, and $R^6$ are as defined as in Formula II', with a hydrogen source (such as hydrogen gas) in the presence of a hydrogenation catalyst (e.g., a rhodium-containing hydrogenation catalyst).

In certain embodiments of the above processes for producing a compound of Formula II or II', the hydrogenation catalyst comprises a transition metal including, but not limited to, rhodium, ruthenium, and iridium. In certain embodiments, the hydrogenation catalyst comprises a transition metal selected from rhodium, ruthenium, and iridium, and a chiral phosphine ligand (L) according to Formula IV below. In certain embodiments, the hydrogenation catalyst comprises rhodium. In certain embodiments, the hydrogenation catalyst comprises rhodium and a chiral phosphine ligand (L) according to Formula IV:

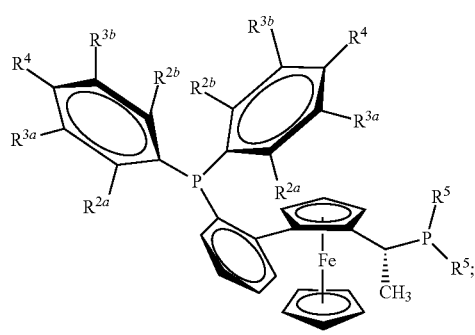

Formula IV wherein each of $R^{2a}$, $R^{2b}$, $R^{3a}$, $R^{3b}$, and $R^4$ is independently selected from hydrogen, methyl, methoxy, and trifluoromethyl; and $R^5$ is secondary alkyl, tertiary alkyl, or cycloalkyl.

In certain embodiments, each of $R^{2a}$, $R^{2b}$, $R^{3a}$, $R^{3b}$, and $R^4$ is hydrogen, and $R^5$ is norbornyl. In certain embodiments, each of $R^{2a}$, $R^{2b}$, $R^{3a}$, $R^{3b}$, and $R^4$ is hydrogen, and $R^5$ is cyclohexyl. In certain embodiments, the hydrogenation catalyst is present in an amount of 2.5 mol % or less. In certain embodiments, the hydrogenation catalyst is present in an amount of 1 mol % or less.

In certain embodiments, the hydrogen gas is present at a pressure of 15 bar or less. In certain embodiments, the hydrogen gas is present at a pressure of 10 bar or less. In certain embodiments, the step of reacting the compound of Formula III or III' with hydrogen gas in the presence of a hydrogenation catalyst is performed in a solvent, and the solvent is selected from dichloromethane (DCM), trifluorotoluene (TFT), tetrahydrofuran (THF), 2-methyltetrahydrofuran (2-methyl-THF), methanol (MeOH), ethanol (EtOH), trifluoroethanol (TFE), isopropanol (iPrOH), hexafluoroisopropanol (HFIP), ethyl acetate (EtOAc), isopropyl acetate (iPrOAc), acetic acid (AcOH), and mixtures thereof. In certain embodiments, the solvent is trifluoroethanol (TFE). In certain embodiments, the compound of Formula II or II' has an enantiomeric excess of the (R)-enantiomer of at least 95%. In certain embodiments, the compound of Formula II or II' has an enantiomeric excess of the (R)-enantiomer of at least 98%.

In another aspect, the invention provides a process for preparing a compound of Formula III' (or a salt thereof):

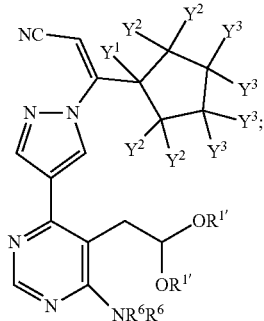

Formula III' the process comprising reacting a compound of Formula VIII' (or a salt thereof):

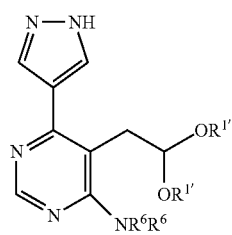

Formula VIII' with a compound of Formula VII:

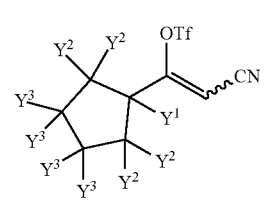

Formula VII in the presence of a base, such that a compound of Formula III' (or salt thereof) is formed; wherein in Formula III' and VII, $Y^1$ is hydrogen or deuterium; each $Y^2$ is the same and is hydrogen or deuterium; each $Y^3$ is the same and is hydrogen or deuterium; and in Formula III' and Formula VIII', each $R^{1'}$ is $C_1$-$C_{10}$ alkyl (e.g., methyl or ethyl), or $C_2$-$C_{10}$ alkenyl (e.g., allyl), or the two $R^{1'}$s, taken together with the oxygen atoms to which they are attached, form a 5-7-membered heterocyclic ring which may optionally be substituted (e.g., a 1,3-dioxolan-2-yl ring, or a 1,3-dioxan-2-yl ring, or a 1,3-benzodioxolan-2-yl ring); and each $R^6$ is independently selected from H and a protecting group. In certain embodiments, $Y^1$ is hydrogen; each $Y^2$ is the same and is hydrogen; and each $Y^3$ is the same and is hydrogen. In other embodiments, $Y^1$ is deuterium; each $Y^2$ is the same and is deuterium; and each $Y^3$ is the same and is deuterium. In certain embodiments, each $R^{1'}$ is $C_1$-$C_{10}$ alkyl; in further embodiments, each $R^{1'}$ is methyl or ethyl. In certain embodiments, each $R^6$ is H. In certain embodiments, one $R^6$ is H and one $R^6$ is a protecting group. In certain embodiments, each $R^6$ is a protecting group. In certain embodiments, the protecting group is a t-butoxycarbonyl group. In certain embodiments, the base is selected from tripotassium phosphate, hydrated tripotassium phosphate and potassium carbonate. In certain embodiments, the step of reacting the compound of Formula VIII' with the compound of Formula VII occurs in a solvent. Nonlimiting examples of solvents include dimethylacetamide (DMAc), water ($H_2O$), and combinations thereof. In certain embodiments, the solvent is a combination of dimethylacetamide and water, for example, dimethylacetamide and water in a ratio in the range between 7:1 DMac:water and 1:2 DMac:water, such as 7:1 DMac:water, 5:4 DMac/water, or 2:1 DMac/water. In some embodiments, the reaction is performed at one or more temperatures in the range of 0° C. to room temperature, e.g, in the range of 0 to 23° C.

In certain aspects, the invention provides methods and compounds for the preparation of a compound of Formula I:

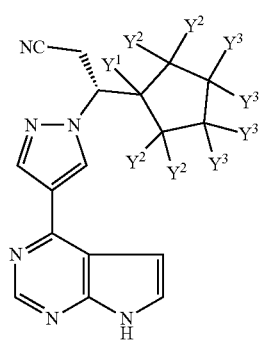

Formula I or a salt thereof, wherein $Y^1$ is hydrogen or deuterium, each $Y^2$ is the same and is hydrogen or deuterium, and each $Y^3$ is the same and is hydrogen or deuterium.

In certain embodiments, a method of preparing a compound of Formula I comprises reacting a compound of Formula II:

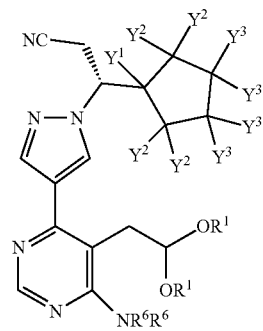

Formula II or a salt thereof,
wherein $Y^1$ is hydrogen or deuterium, each $Y^2$ is the same and is hydrogen or deuterium, and each $Y^3$ is the same and is hydrogen or deuterium; and wherein each $R^1$ is $C_1$-$C_6$ alkyl, or taken together the two $R^1$s form a $C_2$ or $C_3$ alkylene moiety; and each $R^6$ is independently selected from H or a protecting group; under conditions such that a compound of Formula I is formed. In certain embodiments, the step of reacting comprises contacting the compound of Formula II with an acid, such as trifluoroacetic acid, phosphoric acid, trifluoroacetic anhydride, or a combination thereof, under conditions such that a compound of Formula I is formed. In certain embodiments, the acid is selected from trifluoroacetic acid (TFA), phosphoric acid, hydrochloric acid, or a combination thereof. In certain embodiments, the acid is hydrochloric acid. In certain embodiments, wherein the step of reacting comprises contacting the compound of Formula II with phosphoric acid, the compound of Formula I is formed as a phosphoric acid salt. In certain embodiments, the reaction is performed at a temperature from room temperature (or about 20-22° C.) to about 100° C. In certain embodiments, the reaction is performed in a solvent such as toluene, dichloromethane, isopropanol, or a combination thereof. In certain embodiments, the compound of Formula I has an e.e. of at least 90%, 95%, 96%, 97%, 98%, 99% or 99.5% of the (R)-enantiomer. In certain embodiments, the compound of Formula I is ruxolitinib, or a salt thereof. In certain embodiments, the compound of Formula I is CTP-543, or a salt thereof.

Certain aspects of the present invention are directed to processes of synthesizing compounds of Formula II, which are useful as intermediates for the synthesis of JAK inhibitors including ruxolitinib and CTP-543, e.g., as disclosed herein. In certain embodiments, the process comprises an asymmetric hydrogenation which produces an enantiomeric excess of the (R)-enantiomer of the intermediate thereof.

Some embodiments provide a process for preparing a compound of Formula II:

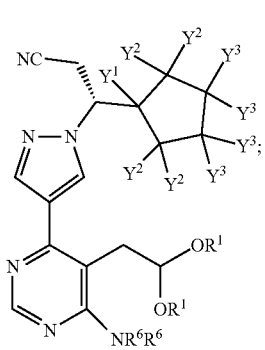

Formula II or a salt thereof,
wherein $Y^1$ is hydrogen or deuterium, each $Y^2$ is the same and is hydrogen or deuterium, and each $Y^3$ is the same and is hydrogen or deuterium; and wherein each $R^1$ is $C_1$-$C_6$ alkyl, or taken together the two $R^1$s form a $C_2$ or $C_3$ alkylene moiety; and each $R^6$ is independently selected from H or a protecting group. In certain embodiments, the process comprises the step of reacting a compound of Formula III:

Formula III or a salt thereof,
(wherein each of $Y^1$, $Y^2$, $Y^3$, $R^1$, and $R^6$ are as defined as in Formula II) with hydrogen gas in the presence of a hydrogenation catalyst to form a compound of Formula II.

In another aspect, the invention provides a process for preparing a compound of Formula II' (or a salt thereof):

Formula II' the process comprising reacting a compound of Formula III' (or a salt thereof):

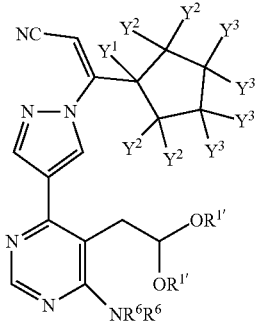

Formula III' with a hydrogen source (e.g., hydrogen gas) in the presence of a hydrogenation catalyst; wherein in Formula II' and III', $Y^1$ is hydrogen or deuterium; each $Y^2$ is the same and is hydrogen or deuterium; each $Y^3$ is the same and is hydrogen or deuterium; each $R^{1'}$ is $C_1$-$C_{10}$ alkyl (e.g., methyl or ethyl), or $C_2$-$C_{10}$ alkenyl (e.g., allyl), or the two $R^{1'}$'s, taken together with the oxygen atoms to which they are attached, form a 5-7-membered heterocyclic ring which may optionally be substituted (e.g., a 1,3-dioxolan-2-yl ring, or a 1,3-dioxan-2-yl ring, or a 1,3-benzodioxolan-2-yl ring); and each $R^6$ is independently selected from H and a protecting group. In certain embodiments, $Y^1$ is hydrogen; each $Y^2$ is the same and is hydrogen; and each $Y^3$ is the same and is hydrogen. In other embodiments, $Y^1$ is deuterium; each $Y^2$ is the same and is deuterium; and each $Y^3$ is the same and is deuterium. In certain embodiments, each $R^{1'}$ is $C_1$-$C_{10}$ alkyl; in further embodiments, each $R^{1'}$ is methyl or ethyl. In certain embodiments, each $R^6$ is H. In certain embodiments, one $R^6$ is H and one $R^6$ is a protecting group. In certain embodiments, each $R^6$ is a protecting group. In certain embodiments, the protecting group is a t-butoxycarbonyl group.

In certain embodiments of the processes for preparing a compound of Formula II or Formula II', the hydrogenation catalyst comprises a transition metal including, but not limited to, rhodium, ruthenium, and iridium. In certain embodiments, the hydrogenation catalyst comprises a transition metal selected from rhodium, ruthenium, and iridium, and a chiral phosphine ligand selected from Walphos W022-1 (CAS #849925-29-7), Walphos W003-1 (CAS #565184-29-4), Walphos W002-1 (CAS #565124-32-9), Walphos W005-1 (CAS #494227-30-4), Walphos W006-1 (CAS #894771-25-6), Walphos W008-1 (CAS #821009-34-1), Walphos W009-1 (CAS #894771-28-9), Walphos W012-1 (CAS #565184-30-7), Walphos W029-1 (CAS #18540687-50-7), Walphos W030-1 (CAS #1854067-62-1), Josiphos J002-1 (CAS #155830-69-6), Josiphos J003-1 (CAS #167416-28-6), Josiphos J006-1 (CAS #292638-88-1), Josiphos J007-1 (CAS #360048-63-1), Josiphos J009-1 (CAS #158923-11-6), Mandyphos M002-1 (CAS #494227-35-), and Taniaphos T002-1 (CAS #1156547-61-3). In certain embodiments, the hydrogenation catalyst is a rhodium-containing catalyst comprising rhodium. In certain embodiments, the hydrogenation catalyst comprises rhodium and a chiral phosphine ligand selected from Walphos W022-1 (CAS #849925-29-7), Walphos W003-1 (CAS #565184-29-4), Walphos W002-1 (CAS #565124-32-9), Walphos W005-1 (CAS #494227-30-4), Walphos W006-1 (CAS #894771-25-6), Walphos W008-1 (CAS #821009-34-1), Walphos W009-1 (CAS #894771-28-9), Walphos W012-1 (CAS #565184-30-7), Walphos W029-1 (CAS #18540687-50-7), Walphos W030-1 (CAS #1854067-62-1), Josiphos J002-1 (CAS #155830-69-6), Josiphos J003-1 (CAS #167416-28-6), Josiphos J006-1 (CAS #292638-88-1), Josiphos J007-1 (CAS #360048-63-1), Josiphos J009-1 (CAS #158923-11-6), Mandyphos M002-1 (CAS #494227-35-), and Taniaphos T002-1 (CAS #1156547-61-3). In certain embodiments, the hydrogenation catalyst comprises a transition metal selected from rhodium, ruthenium, and iridium, and a chiral phosphine ligand (L) according to Formula IV below. In certain embodiments, the hydrogenation catalyst comprises rhodium and a chiral phosphine ligand (L) according to Formula IV:

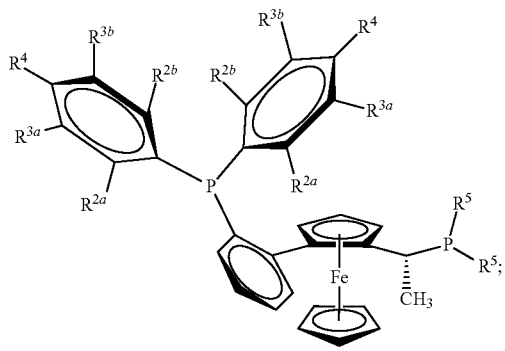

Formula IV wherein each of $R^{2a}$, $R^{2b}$, $R^{3a}$, $R^{3b}$, and $R^4$ is independently selected from hydrogen, methyl, methoxy, and trifluoromethyl; and $R^5$ is secondary alkyl, tertiary alkyl, or cycloalkyl.

In certain embodiments, the reaction of a compound of Formula III to form a compound of Formula II is performed in the presence of a catalyst/ligand amount of about 0.25 mol % to about 10 mol % of Rh catalyst and a ligand (such as Walphos W022-1). In certain embodiments, the solvent is trifluoroethanol. In certain embodiments, the pressure of hydrogen gas is 10 bar. In certain embodiments, the temperature is a temperature in the range of 15-25° C. In certain embodiments, the compound of Formula II has an e.e. of at least 90%, 95%, 96%, 97%, 98%, 99% or 99.5% of the (R)-enantiomer. In another aspect, the invention provides a process for preparing a compound of Formula II, the method comprising the step of reacting a compound of Formula V:

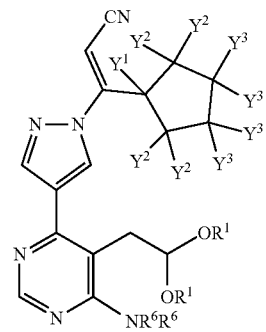

Formula V or a salt thereof
(wherein each of $Y^1$, $Y^2$, $Y^3$, $R^1$ and $R^6$ is defined as in Formula II) with hydrogen gas in the presence of a hydrogenation catalyst comprising rhodium and a chiral phosphine ligand (L') according to Formula VI:

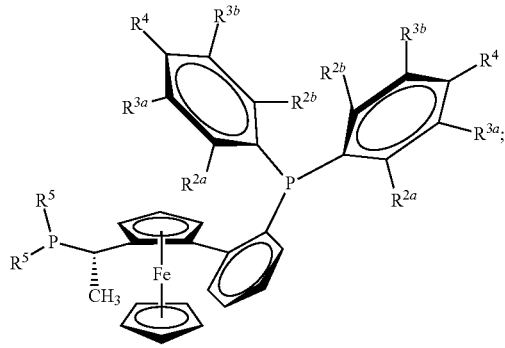

Formula VI wherein each of $R^{2a}$, $R^{2b}$, $R^{3a}$, $R^{3b}$, and $R^4$ is independently selected from hydrogen, methyl, methoxy, and trifluoromethyl; and $R^5$ is secondary alkyl, tertiary alkyl, or cycloalkyl. In certain embodiments, the hydrogenation catalyst comprises a transition metal selected from rhodium, ruthenium, and iridium, and a chiral phosphine ligand according to Formula VI above.

In another aspect, the invention provides a process for preparing a compound of Formula II', the method comprising the step of reacting a compound of Formula V':

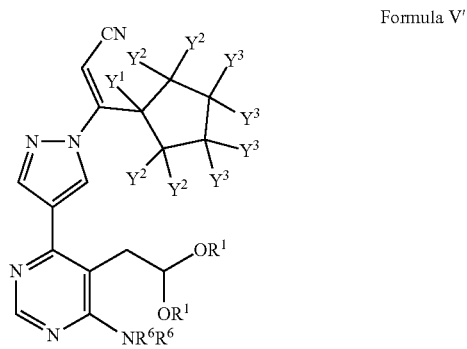

Formula V' or a salt thereof
(wherein each of $Y^1$, $Y^2$, $Y^3$, $R^1$ and $R^6$ is defined as in Formula II') with hydrogen gas in the presence of a hydrogenation catalyst comprising rhodium and a chiral phosphine ligand (L') according to Formula VI:

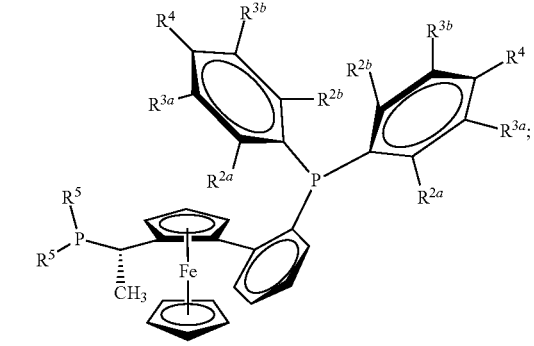

Formula VI wherein each of $R^{2a}$, $R^{2b}$, $R^{3a}$, $R^{3b}$, and $R^4$ is independently selected from hydrogen, methyl, methoxy, and trifluoromethyl; and $R^5$ is secondary alkyl, tertiary alkyl, or cycloalkyl. In certain embodiments, the hydrogenation catalyst comprises a transition metal selected from rhodium, ruthenium, and iridium, and a chiral phosphine ligand according to Formula VI above. In some embodiments, the process for preparing a compound of Formula II or II' comprises the step of reacting a mixture comprising a mole ratio of ≥80% of a compound of Formula III (for preparing a compound of Formula II) or III' (for preparing a compound of Formula II') as disclosed herein to ≤20% of a compound of Formula V (for preparing a compound of Formula II) or V' (for preparing a compound of Formula II') as disclosed herein with hydrogen gas in the presence of a hydrogenation catalyst comprising rhodium and a chiral phosphine ligand (L) according to Formula IV as disclosed herein. In some embodiments, the process comprises the step of reacting a mixture comprising a mole ratio of ≥90% of a compound of Formula III (for preparing a compound of Formula II) or III' (for preparing a compound of Formula II') as disclosed herein to ≤10% of a compound of Formula V or V' as disclosed herein with hydrogen gas in the presence of a hydrogenation catalyst comprising rhodium and a chiral phosphine ligand (L) according to Formula IV as disclosed herein. In certain embodiments, the process comprises the step of reacting a mixture comprising a mole ratio of ≥95% of a compound of Formula III or III' as disclosed herein to ≤5% of a compound of Formula V or V' as disclosed herein with hydrogen gas in the presence of a hydrogenation catalyst comprising rhodium and a chiral phosphine ligand (L) according to Formula IV as disclosed herein. In certain embodiments, the compound of Formula I has an e.e. of at least 90%, 95%, 96%, 97%, 98%, 99% or 99.5% (of the (R)-enantiomer). In certain embodiments, the hydrogenation catalyst disclosed above comprises a transition metal selected from rhodium, ruthenium, and iridium, and a chiral phosphine ligand (L) according to Formula IV as disclosed herein. In certain embodiments, the process for preparing a compound of Formula II comprises the step of reacting a mixture comprising a mole ratio of ≥80% of a compound of Formula V as disclosed herein to ≤20% of a compound of Formula III as disclosed herein with hydrogen gas in the presence of a hydrogenation catalyst comprising rhodium and a chiral phosphine ligand (L') according to Formula VI as disclosed herein. In some embodiments, the process comprises the step of reacting a mixture comprising mole ratio of ≥90% of a compound of Formula V as disclosed herein to ≤10% of a compound of Formula III as disclosed herein with hydrogen gas in the presence of a hydrogenation catalyst comprising rhodium and a chiral phosphine ligand (L') according to Formula VI as disclosed herein. In some embodiments, the process comprises the step of reacting a mixture comprising a mole ratio of ≥95% of a compound of Formula V as disclosed herein to ≤5% of a compound of Formula III as disclosed herein with hydrogen gas in the presence of a hydrogenation catalyst comprising rhodium and a chiral phosphine ligand (L') according to Formula VI as disclosed herein. In certain embodiments, the hydrogenation catalyst disclosed above comprises a transition metal selected from rhodium, ruthenium, and iridium, and a chiral phosphine ligand (L') according to Formula VI as disclosed herein.

In certain embodiments, the process for preparing a compound of Formula II' comprises the step of reacting a mixture comprising a mole ratio of ≥80% of a compound of Formula V as disclosed herein to ≤20% of a compound of Formula III' as disclosed herein with hydrogen gas in the presence of a hydrogenation catalyst comprising rhodium and a chiral phosphine ligand (L') according to Formula VI as disclosed herein. In some embodiments, the process comprises the step of reacting a mixture comprising mole ratio of ≥90% of a compound of Formula V as disclosed herein to ≤10% of a compound of Formula III' as disclosed herein with hydrogen gas in the presence of a hydrogenation catalyst comprising rhodium and a chiral phosphine ligand (L') according to Formula VI as disclosed herein. In some embodiments, the process comprises the step of reacting a mixture comprising a mole ratio of ≤95% of a compound of Formula V as disclosed herein to ≥5% of a compound of Formula III' as disclosed herein with hydrogen gas in the presence of a hydrogenation catalyst comprising rhodium and a chiral phosphine ligand (L') according to Formula VI as disclosed herein. In certain embodiments, the hydrogenation catalyst disclosed above comprises a transition metal selected from rhodium, ruthenium, and iridium, and a chiral phosphine ligand (L') according to Formula VI as disclosed herein.

In some embodiments of the Formulas described herein, $R^5$ is selected from norbornyl, cyclohexyl, cyclopentyl, and tert-butyl. In some embodiments, $R^5$ is norbornyl. In some embodiments, $R^5$ is cyclohexyl.

In some embodiments of the formulas described herein, each of $R^{2a}$, $R^{2b}$, $R^{3a}$, $R^{3b}$, and $R^4$ is hydrogen. In some embodiments, each of $R^{2a}$, $R^{2b}$, and $R^4$ is hydrogen, and $R^{3a}$ and $R^{3b}$ are each methyl or each trifluoromethyl. In some embodiments, each of $R^{2a}$ and $R^{2b}$ is hydrogen, $R^4$ is methoxy, and $R^{3a}$ and $R^{3b}$ are each methyl. In some embodiments, each of $R^{2a}$, $R^{2b}$, $R^{3a}$, and $R^{3b}$ is hydrogen, and $R^4$ is methoxy, trifluoromethyl, or methyl. In some embodiments, each of $R^{3a}$, $R^{3b}$, and $R^4$ is hydrogen, one of $R^{2a}$ and $R^{2b}$ is hydrogen and the other of $R^{2a}$ and $R^{2b}$ is methyl. In some embodiments, each of $R^{2a}$, $R^{2b}$, $R^{3a}$, $R^{3b}$, and $R^4$ is hydrogen, and $R^5$ is selected from norbornyl, cyclohexyl, cyclopentyl, and tert-butyl. In some embodiments, each of $R^{2a}$, $R^{2b}$, $R^{3a}$, $R^{3b}$, and $R^4$ is hydrogen, and $R^5$ is norbornyl. In some embodiments, each of $R^{2a}$, $R^{2b}$, $R^{3a}$, $R^{3b}$, and $R^4$ is hydrogen, and $R^5$ is cyclohexyl.

In some embodiments of the formulas described herein, the hydrogenation catalyst is formed by mixing a rhodium pre-catalyst of the formula $[Rh(L_1)(L_2)]^+NC^-$ with the chiral phosphine ligand (L) of Formula IV or (L') of Formula VI; wherein $L_1$ and $L_2$ are the same or different, $L_1$ and $L_2$ are each independently a pair of monodentate ligands or a bidentate ligand, wherein the monodentate ligand is selected from an alkene ligand and a solvent ligand, wherein the bidentate ligand is a diene; and wherein $NC^-$ is a non-coordinating counterion selected from tetrafluoroborate, triflate, hexafluorophosphate, hexafluoroantimonate, and perchlorate. In some embodiments, the alkene ligand may have one, two, three, four, or more double bonds. In some embodiments, the alkene ligand is selected from ethylene, cyclooctene, and norbornene. In some embodiments, the solvent ligand is selected from acetonitrile, tetrahydrofuran, 2-methyltetrahydrofuran, methanol, ethanol, trifluoroethanol, and isopropanol. In some embodiments, the diene ligand is selected from 1,5-cyclooctadiene (COD), 1,5-hexadiene, and norbornadiene. In some embodiments, the rhodium pre-catalyst is bis(norbornadiene)rhodium(I)tetrafluoroborate or $[Rh(COD)_2]^+BF_4^-$. In some embodiments, the rhodium pre-catalyst is $[Rh(COD)_2]^+BF_4^-$.

In some embodiments, the hydrogenation catalyst comprises $[Rh(L_1)(L)]^+BF_4^-$, wherein $(L_1)$ is a pair of monodentate ligands or a bidentate ligand, and (L) is:

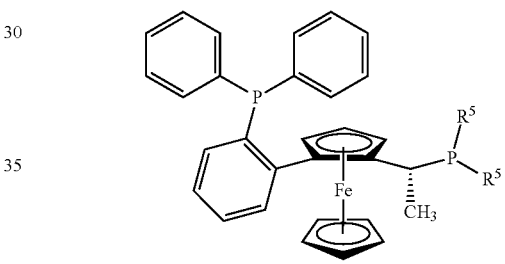

(1S)-1-[(1R)-1-(Dicyclohexylphosphino)ethyl]-2-[2-(diphenylphosphino)phenyl]ferrocene (CAS #565184-29-4), wherein $R^5$ is cyclohexyl. In some embodiments, the hydrogenation catalyst comprises $[Rh(COD)(565184-29-4)]^+BF_4^-$.

In some embodiments, the hydrogenation catalyst comprises $[Rh(L_1)(L')]^+BF_4^-$, wherein $(L_1)$ is a pair of monodentate ligands or a bidentate ligand, and (L') is:

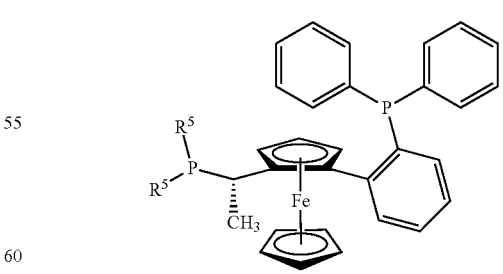

(1R)-1-[(1S)-1-(Dicyclohexylphosphino)ethyl]-2-[2-(diphenylphosphino)phenyl]ferrocene (CAS #849925-19-5), wherein $R^5$ is cyclohexyl. In some embodiments, the hydrogenation catalyst comprises $[Rh(COD)(849925-19-5)]^+BF_4^-$.

In some embodiments, the hydrogenation catalyst comprises [Rh(L₁)(L)]⁺BF₄⁻, wherein (L₁) is a pair of monodentate ligands or a bidentate ligand, and (L) is:

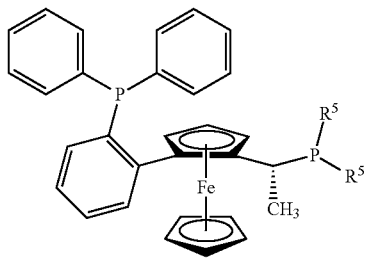

(1S)-1-[(1R)-1-[Bis(bicyclo[2.2.1]hept-2-yl)phosphino]ethyl]-2-[2-(diphenylphosphino)phenyl]ferrocene (CAS #849925-29-7), wherein R⁵ is norbornyl. In some embodiments, the hydrogenation catalyst comprises [Rh(COD)(849925-29-7)]⁺BF₄⁻.

In some embodiments, the hydrogenation catalyst comprises [Rh(L₁)(L')]⁺BF₄⁻, wherein (L₁) is a pair of monodentate ligands or a bidentate ligand, and (L') is:

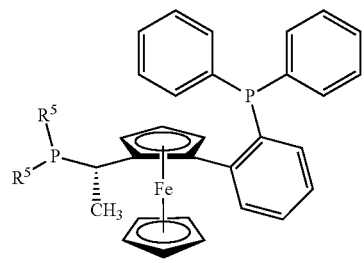

(1R)-1-[(1S)-1-[Bis(bicyclo[2.2.1]hept-2-yl)phosphino]ethyl]-2-[2-(diphenylphosphino)phenyl]ferrocene (CAS #849925-45-7), wherein R⁵ is norbornyl. In some embodiments, the hydrogenation catalyst comprises [Rh(COD)(849925-45-7)]⁺BF₄⁻.

In some embodiments wherein R⁵ is norbornyl, the norbornyl groups are bonded to the phosphorus atom in any of the following configurations shown in Table 1 below:

TABLE 1

| Nb₁ | | Nb₂ | | P(Nb₁)(Nb₂) |
|---|---|---|---|---|
| endo | R | endo | R | N/A |
| exo | R | exo | R | N/A |
| endo | S | endo | S | N/A |
| exo | S | exo | S | N/A |
| endo | R | exo | R | $R_P$ |
| endo | R | endo | S | $R_P$ |
| endo | R | exo | S | $R_P$ |
| endo | R | exo | R | $S_P$ |
| endo | R | endo | S | $S_P$ |
| endo | R | exo | S | $S_P$ |
| exo | R | endo | R | $R_P$ |
| exo | R | endo | S | $R_P$ |
| exo | R | exo | S | $R_P$ |
| exo | R | endo | R | $S_P$ |
| exo | R | endo | S | $S_P$ |
| exo | R | exo | S | $S_P$ |
| endo | S | exo | S | $R_P$ |
| endo | S | endo | R | $R_P$ |
| endo | S | exo | R | $R_P$ |
| endo | S | exo | S | $S_P$ |

TABLE 1-continued

| Nb₁ | | Nb₂ | | P(Nb₁)(Nb₂) |
|---|---|---|---|---|
| endo | S | endo | R | $S_P$ |
| endo | S | exo | R | $S_P$ |
| exo | S | endo | S | $R_P$ |
| exo | S | endo | R | $R_P$ |
| exo | S | exo | R | $R_P$ |
| exo | S | endo | S | $S_P$ |
| exo | S | endo | R | $S_P$ |
| exo | S | exo | R | $S_P$ | wherein (1S)-exo-norbornyl is

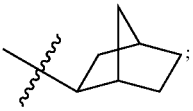 [SMILES: *C1CC2CCC1C2]

(1R)-exo-norbornyl is

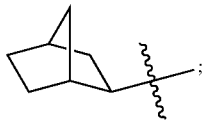

(1S)-endo-norbornyl is

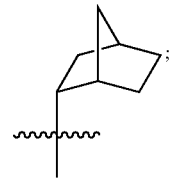 [SMILES: *C1CC2CCC1C2]

and (1R)-endo-norbornyl is

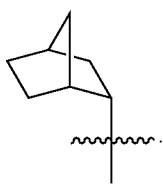 [SMILES: *C1CC2CCC1C2]

In some embodiments, the chiral phosphine ligand (L) according to Formula III or (L') according to Formula VI, wherein R⁵ is norbornyl, comprises a single isomer selected from Table 1, or comprises a mixture of 2, 3, 4, or more isomers selected from Table 1. The column P(Nb₁)(Nb₂) provides the stereochemical configuration of the phosphorus atom.

In certain embodiments, the invention provides a process for preparing a compound of Formula II:

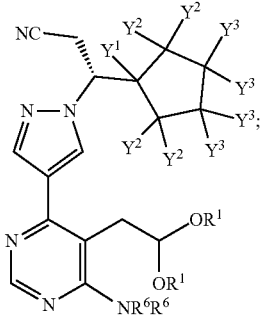

Formula II or a salt thereof;

wherein $Y^1$ is hydrogen; each $Y^2$ is the same and is hydrogen or deuterium; each $Y^3$ is the same and is hydrogen or deuterium; and each $R^1$ is $C_1$-$C_6$ alkyl, or taken the two $R^1$s together form a $C_2$ or $C_3$ alkylene moiety; and each $R^6$ is independently selected from H or a protecting group. In certain embodiments, the process comprises the step of reacting a compound of Formula XI:

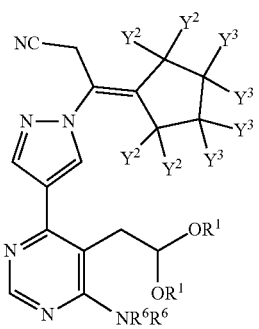

Formula XI or a salt thereof;

(wherein each of $Y^2$, $Y^3$, $R^1$, and $R^6$ are as defined as in Formula II), with hydrogen gas in the presence of a hydrogenation catalyst to form a compound of Formula II. In certain embodiments, the hydrogenation catalyst comprises a transition metal selected from rhodium, ruthenium, and iridium. In certain embodiments, the hydrogenation catalyst further comprises a chiral phosphine ligand selected from Formula VI:

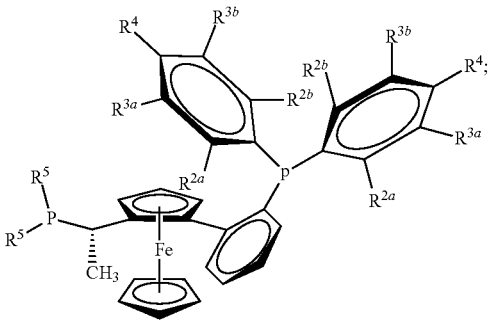

Formula VI wherein each of $R^{2a}$, $R^{2b}$, $R^{3a}$, $R^{3b}$, and $R^4$ is independently selected from hydrogen, methyl, methoxy, and trifluoromethyl; and $R^5$ is aryl, secondary alkyl, tertiary alkyl, or cycloalkyl, and Formula XII:

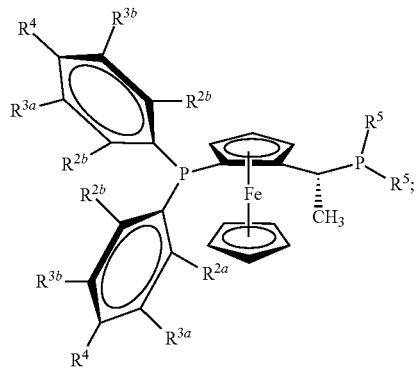

Formula XII wherein each of $R^{2a}$, $R^{2b}$, $R^{3a}$, $R^{3b}$, and $R^4$ is independently selected from hydrogen, methyl, methoxy, and trifluoromethyl; and $R^5$ is secondary alkyl, tertiary alkyl, or cycloalkyl. In certain embodiments, the hydrogenation catalyst comprises rhodium and a chiral phosphine ligand selected from Walphos W002-2 (CAS #1854067-25-6) and Josiphos J002-1 (CAS #155830-69-6). In certain embodiments, the compound of Formula I has an e.e. of at least 90%, 95%, 96%, 97%, 98%, 99% or 99.5% of the (R)-enantiomer.

In certain embodiments, the invention provides a process for preparing a compound of Formula II':

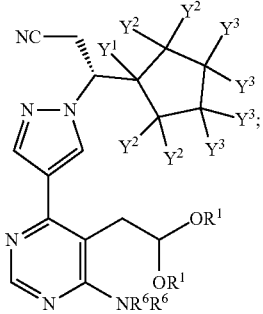

Formula II' or a salt thereof;
wherein $Y^1$ is hydrogen and $Y^2$, $Y^3$, $R^1$ and $R^6$ are defined above for Formula II'. In certain embodiments, the process comprises the step of reacting a compound of Formula XI':

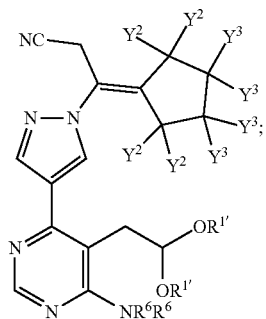

Formula XI' or a salt thereof;
(wherein each of $Y^2$, $Y^3$, $R^{1'}$, and $R^6$ are as defined as in Formula II'), with a hydrogen source (such as hydrogen gas) in the presence of a hydrogenation catalyst to form a compound of Formula II. In certain embodiments, the hydrogenation catalyst comprises a transition metal selected from rhodium, ruthenium, and iridium. In certain embodiments, the hydrogenation catalyst further comprises a chiral phosphine ligand selected from Formula VI:

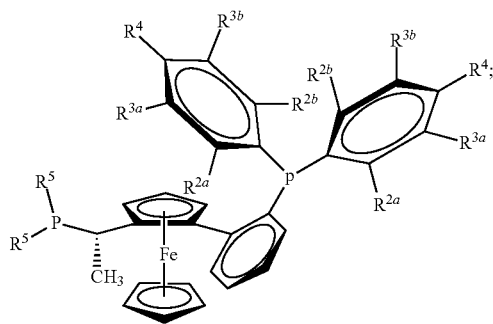

Formula VI wherein each of $R^{2a}$, $R^{2b}$, $R^{3a}$, $R^{3b}$, and $R^4$ is independently selected from hydrogen, methyl, methoxy, and trifluoromethyl; and $R^5$ is aryl, secondary alkyl, tertiary alkyl, or cycloalkyl, and Formula XII:

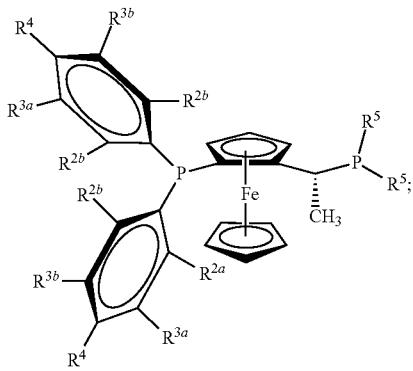

Formula XII wherein each of $R^{2a}$, $R^{2b}$, $R^{3a}$, $R^{3b}$, and $R^4$ is independently selected from hydrogen, methyl, methoxy, and trifluoromethyl; and $R^5$ is secondary alkyl, tertiary alkyl, or cycloalkyl. In certain embodiments, the hydrogenation catalyst comprises rhodium and a chiral phosphine ligand selected from Walphos W002-2 (CAS #1854067-25-6) and Josiphos J002-1 (CAS #155830-69-6). In certain embodiments, the compound of Formula I has an e.e. of at least 90%, 95%, 96%, 97%, 98%, 99% or 99.5% of the (R)-enantiomer.

In some embodiments of the above methods for preparing a compound of Formula II or II', the amount of hydrogenation catalyst comprising rhodium and a chiral phosphine ligand, or the amount of hydrogenation catalyst comprising rhodium, or the amount of chiral phosphine ligand is 0.1-10 mol %, 0.5-8 mol %, 1-6 mol %, 1.5-5 mol %, 2-4 mol %, or 2.5-3 mol %. In some embodiments, the amount of hydrogenation catalyst comprising rhodium and a chiral phosphine ligand, or the amount of hydrogenation catalyst comprising rhodium, or the amount of chiral phosphine ligand is 5 mol % or less, 2.5 mol % or less, 2 mol % or less, 1.5 mol % or less, 1 mol % or less, or 0.5 mol % or less. In some embodiments, the amount is 5 mol % or less. In some embodiments, the amount is 2.5 mol % or less. In some embodiments, the amount is 1 mol % or less. In some embodiments, the amounts of hydrogenation catalyst disclosed above include amounts of hydrogenation catalyst comprising a transition metal selected from rhodium, ruthenium, and iridium, and a chiral phosphine ligand, or an amount of hydrogenation catalyst comprising a transition metal selected from rhodium, ruthenium, and iridium.

In some embodiments, the step of reacting further comprises treating with an additive, a non-limiting example of which is tetrafluoroboric acid (HBF$_4$). In some embodiments, the amount of HBF$_4$ is in the range of 0.5 to 1.0 equivalents.

In some embodiments, the step of reacting is performed in a solvent. Non-limiting examples of the solvent include dichloromethane (DCM), trifluorotoluene (TFT), tetrahydrofuran (THF), 2-methyltetrahydrofuran (2-methyl-THF), methanol (MeOH), ethanol (EtOH), trifluoroethanol (TFE), isopropanol (iPrOH), hexafluoroisopropanol (HFIP), ethyl acetate (EtOAc), isopropyl acetate (iPrOAc), acetic acid (AcOH), and mixtures thereof. In some embodiments, the solvent is dichloromethane. In some embodiments, the solvent is tetrahydrofuran. In some embodiments, the solvent is trifluoroethanol. In some embodiments, the solvent is hexafluoroisopropanol (HFIP). In some embodiments, the solvent is DCM and the step of reacting further comprises treating with HBF$_4$. In some embodiments, the solvent is TFE and the step of reacting further comprises treating with HBF$_4$.

In certain embodiments, the solvent is present at 1-50 volumes (vol), 2.5-20 volumes, 5-15 volumes, or 5-10 volumes. In certain embodiments, the solvent is present at 10 volumes. In certain embodiments, the solvent is present at 5 volumes. In certain embodiments, the solvent is present at 2.5 volumes.

In certain embodiments, hydrogen gas is present in the reaction step at a pressure in the range of 1-200 bar, 5-100 bar, 10-50 bar, or 15-30 bar. In certain embodiments, hydrogen gas is present in the reaction step at a pressure of 50 bar or less. In certain embodiments, hydrogen gas is present in the reaction step at a pressure of 20 bar or less. In certain embodiments, hydrogen gas is present at a pressure of 15 bar or less. In certain embodiments, hydrogen gas is present at a pressure of 10 bar or less. In certain embodiments, hydrogen gas is present at a pressure of 5 bar or less.

In certain embodiments, the process forms a compound of Formula II or II' having an enantiomeric excess of the (R)-enantiomer of at least 80%. In some embodiments, the process forms a compound of Formula II or II' having an enantiomeric excess of the (R)-enantiomer of at least 90%. In some embodiments, the process forms a compound of Formula II or II' having an enantiomeric excess of the (R)-enantiomer of at least 95%. In some embodiments, the process forms a compound of Formula II or II' having an enantiomeric excess of the (R)-enantiomer of at least 97%. In some embodiments, the process forms a compound of Formula II or II' having an enantiomeric excess of the (R)-enantiomer of at least 98%. In some embodiments, the process forms a compound of Formula II or II' having an enantiomeric excess of the (R)-enantiomer of at least 99%.

In certain embodiments of the above methods for preparing a compound of Formula II or II', the method comprises the further step of treating the compound of Formula II or II' with an acid to form a salt of the compound of Formula II or II'.

Certain aspects of the present invention are directed to processes of synthesizing compounds of Formula III, which are useful as intermediates for the synthesis of JAK inhibitors including ruxolitinib and CTP-543, e.g., as disclosed herein.

In certain embodiments, the invention provides a process for preparing a compound of Formula III:

Formula III or a salt thereof;
comprising reacting a compound of Formula VIII:

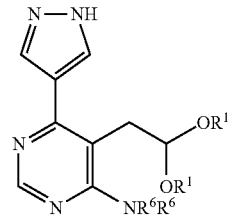

Formula VIII or a salt thereof;
with a compound of Formula VII:

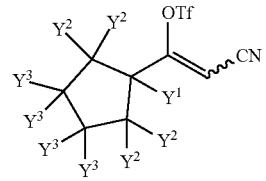

Formula VII in the presence of a base to form a compound of Formula III; wherein Y$^1$ is hydrogen or deuterium, each Y$^2$ is the same and is hydrogen or deuterium, each Y$^3$ is the same and is hydrogen or deuterium, each R$^1$ is C$_1$-C$_6$ alkyl, or taken together the two R$^1$s form a C$_2$ or C$_3$ alkylene moiety; and each R$^6$ is independently selected from H or a protecting group. The base can be an inorganic base such as sodium or potassium phosphate, or sodium or potassium carbonate. Nonlimiting examples of the base include tripotassium phosphate, such as hydrated tripotassium phosphate, and potassium carbonate. In some embodiments, the step of reacting is performed in a solvent. Nonlimiting examples of solvents include dimethylacetamide (DMAc), water (H$_2$O), and combinations thereof. In certain embodiments, the solvent is a combination of dimethylacetamide and water, for example, dimethylacetamide and water in a ratio in the range between 7:1 DMAc:water and 1:2 DMac:water, such as 7:1 DMac:water, 5:4 DMac/water, or 2:1 DMac/water. In some embodiments, the reaction is performed at one or more temperatures in the range of 0° C. to room temperature, e.g, in the range of 0 to 23° C.

In another aspect, the invention provides a process for preparing a compound of Formula III' (or a salt thereof):

Formula III' the process comprising reacting a compound of Formula VIII' (or a salt thereof):

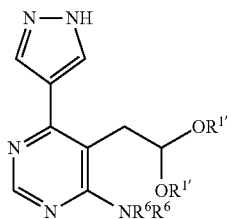
Formula VIII' with a compound of Formula VII:

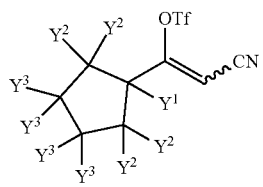
Formula VII in the presence of a base, such that a compound of Formula III' (or salt thereof) is formed; wherein in Formula III' and VII, $Y^1$ is hydrogen or deuterium; each $Y^2$ is the same and is hydrogen or deuterium; each $Y^3$ is the same and is hydrogen or deuterium; and in Formula III' and VIII', each $R^{1'}$ is $C_1$-$C_{10}$ alkyl (e.g., methyl or ethyl), or $C_2$-$C_{10}$ alkenyl (e.g., allyl), or the two $R^{1'}$s, taken together with the oxygen atoms to which they are attached, form a 5-7-membered heterocyclic ring which may optionally be substituted (e.g., a 1,3-dioxolan-2-yl ring, or a 1,3-dioxan-2-yl ring, or a 1,3-benzodioxolan-2-yl ring); and each $R^6$ is independently selected from H and a protecting group. In certain embodiments, $Y^1$ is hydrogen; each $Y^2$ is the same and is hydrogen; and each $Y^3$ is the same and is hydrogen. In other embodiments, $Y^1$ is deuterium; each $Y^2$ is the same and is deuterium; and each $Y^3$ is the same and is deuterium. In certain embodiments, each $R^{1'}$ is $C_1$-$C_{10}$ alkyl; in further embodiments, each $R^{1'}$ is methyl or ethyl. In certain embodiments, each $R^6$ is H. In certain embodiments, one $R^6$ is H and one $R^6$ is a protecting group. In certain embodiments, each $R^6$ is a protecting group. In certain embodiments, the protecting group is a t-butoxycarbonyl group. The base can be an inorganic base such as sodium or potassium phosphate, or sodium or potassium carbonate. Nonlimiting examples of the base include tripotassium phosphate, such as hydrated tripotassium phosphate, and potassium carbonate. In some embodiments, the step of reacting is performed in a solvent. Nonlimiting examples of solvents include dimethylacetamide (DMAc), water (H$_2$O), and combinations thereof. In certain embodiments, the solvent is a combination of dimethylacetamide and water, for example, dimethylacetamide and water in a ratio in the range between 7:1 DMac:water and 1:2 DMac:water, such as 7:1 DMac:water, 5:4 DMac/water, or 2:1 DMac/water. In some embodiments, the reaction is performed at one or more temperatures in the range of 0° C. to room temperature, e.g, in the range of 0 to 23° C.

Certain aspects of the present invention are directed to processes of synthesizing compounds of Formula XI, which are useful as intermediates for the synthesis of JAK inhibitors including ruxolitinib and CTP-543, e.g., as disclosed herein. In certain embodiments, the invention provides a process for preparing a compound of Formula XI:

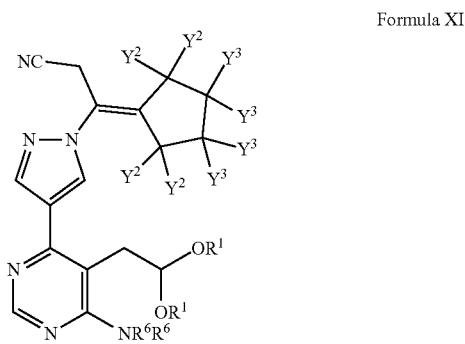
Formula XI or a salt thereof;

comprising reacting a compound of Formula III:

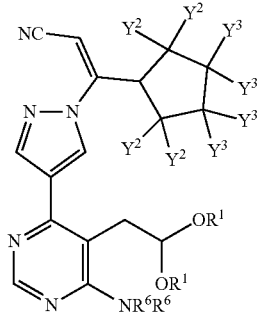
Formula III or a salt thereof;

with a base to form a compound of Formula XI; wherein $Y^1$ is hydrogen or deuterium, each $Y^2$ is the same and is hydrogen or deuterium, each $Y^3$ is the same and is hydrogen or deuterium, each $R^1$ is $C_1$-$C_6$ alkyl, or taken together the two $R^1$s form a $C_2$ or $C_3$ alkylene moiety; and each $R^6$ is independently selected from H or a protecting group. Nonlimiting examples of the base include lithium hydroxide, sodium hydroxide and potassium hydroxide. In some embodiments, the step of reacting is performed in a solvent. Nonlimiting examples of solvents include dimethylacetamide (DMAc), water (H$_2$O), and combinations thereof. In some embodiments, the reaction is performed at one or more temperatures in the range of 0° C. to room temperature, e.g, in the range of 0 to 23° C.

Certain aspects of the present invention are directed to processes of synthesizing compounds of Formula XI, which are useful as intermediates for the synthesis of JAK inhibitors including ruxolitinib and CTP-543, e.g., as disclosed herein. In certain embodiments, the invention provides a process for preparing a compound of Formula XI':

Formula XI'

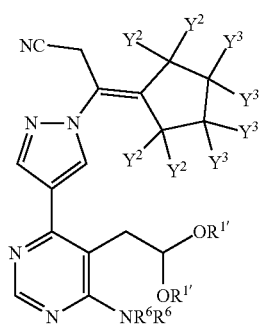

or a salt thereof;
the method comprising reacting a compound of Formula III':

Formula III'

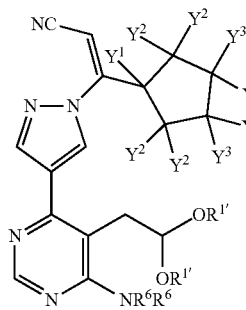

or a salt thereof;
with a base to form a compound of Formula XI'; wherein $Y^1$ is hydrogen or deuterium and wherein each of $Y^2$, $Y^3$, $R^{1'}$, and $R^6$ are as defined as in Formula II'. In certain embodiments, $Y^1$ is hydrogen. In certain embodiments, each $Y^2$ is the same and is deuterium; and each $Y^3$ is the same and is deuterium. In other embodiments, each $Y^2$ is the same and is hydrogen; and each $Y^3$ is the same and is hydrogen. In certain embodiments, each $R^{1'}$ is methyl. In certain embodiments, each $R^{1'}$ is ethyl. In certain embodiments, each $R^6$ is H. In certain embodiments, one $R^6$ is H and the other $R^6$ is a protecting group. In certain embodiments, the protecting group is a Boc group. Nonlimiting examples of the base include lithium hydroxide, sodium hydroxide and potassium hydroxide. In some embodiments, the step of reacting is performed in a solvent. Nonlimiting examples of solvents include dimethylacetamide (DMAc), water (H₂O), and combinations thereof. In some embodiments, the reaction is performed at one or more temperatures in the range of 0° C. to room temperature, e.g., a temperature in the range of 0 to about 23° C.

Certain aspects of the present invention are directed to processes of synthesizing compounds of Formula VIII, which are useful as intermediates for the synthesis of JAK inhibitors including ruxolitinib and CTP-543, e.g., as disclosed herein. In certain embodiments, a process for preparing a compound of Formula VIII (or a salt thereof):

Formula VIII

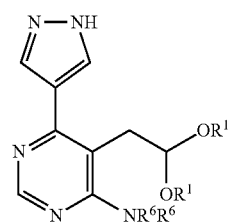

comprises reacting a compound of Formula IX:

Formula IX

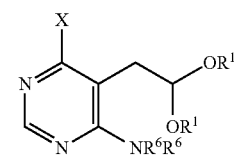

or a salt thereof;
with

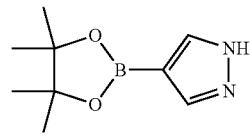

(BPin-pyrazole) (or another pyrazol-4-yl boronic ester) and a catalytic amount of a palladium catalyst in the presence of a base such that a compound of Formula VIII is formed; wherein each $R^1$ is $C_1$-$C_6$ alkyl, or taken together the two $R^1$s form a $C_2$ or $C_3$ alkylene moiety; each $R^6$ is independently selected from H or a protecting group; and X is I, Br, Cl, or triflate.

Certain aspects of the present invention are directed to a process for preparing a compound of Formula VIII' (or a salt thereof):

Formula VIII'

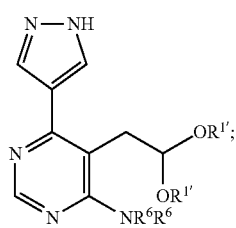

the process comprising reacting a compound of Formula IX' (or a salt thereof):

Formula IX'

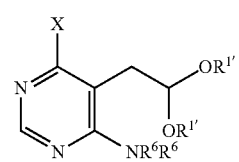

with a compound represented by the formula:

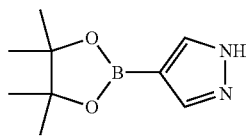

(BPin-pyrazole) (or another pyrazole boronic ester) and a catalytic amount of a palladium catalyst (such as Pd(PPh₃)₄) in the presence of a base, such that a compound of Formula VIII' is formed; wherein in Formula VIII' and IX', each $R^{1'}$ is $C_1$-$C_{10}$ alkyl (e.g., methyl or ethyl), or $C_2$-$C_{10}$ alkenyl (e.g., allyl), or the two $R^{1'}$s, taken together with the oxygen atoms to which they are attached, form a 5-7-membered heterocyclic ring which may optionally be substituted (e.g., a 1,3-dioxolan-2-yl ring, or a 1,3-dioxan-2-yl ring, or a 1,3-benzodioxolan-2-yl ring); and each $R^6$ is independently selected from H and a protecting group. In certain embodiments, each $R^{1'}$ is $C_1$-$C_{10}$ alkyl; in further embodiments, each $R^{1'}$ is methyl or ethyl. In certain embodiments, each $R^6$ is H. In certain embodiments, one $R^6$ is H and one $R^6$ is a protecting group. In certain embodiments, each $R^6$ is a protecting group. In certain embodiments, the protecting group is a t-butoxycarbonyl group. In certain embodiments, the base is selected from potassium carbonate and dibasic sodium phosphate dihydrate.

In certain embodiments of Formula IX or IX', X is Cl. In certain embodiments, the palladium catalyst is Pd(PPh₃)₄ or a combination of Pd₂(dba)₃ and XPhos. In certain embodiments, the catalytic amount of palladium catalyst is in the range of 0.1-10 mol %, 0.5-5 mol %, 3-6 mol %, or 1-2.5 mol %. In certain embodiments, nonlimiting examples of the base include potassium carbonate and dibasic sodium phosphate dihydrate. In some embodiments, the step of reacting is performed in a solvent. Nonlimiting examples of solvents include n-butanol, 1,4-dioxane, THF, and combinations thereof. In some embodiments, the reaction is performed at one or more temperatures in the range of room temperature to 120° C., or 60-90° C., or the reflux temperature of the solvent.

In certain embodiments of Formulas II, II', III, III', V, V', VIII, VIII', IX, IX', XI or XI', the protecting group is selected from t-butoxycarbonyl (Boc), triflyl (Tf, SO₂—CF₃), trifluoroacetyl (F₃—Ac), and trityl (Tr, CPh₃). In certain embodiments, both $R^6$ are t-butoxycarbonyl (Boc). In certain embodiments, one $R^6$ is t-butoxycarbonyl (Boc) and the other $R^6$ is H. In certain embodiments, one $R^6$ is triflyl (Tf) and the other $R^6$ is H. In certain embodiments, one $R^6$ is trifluoroacetyl (F₃—Ac) and the other $R^6$ is H. In certain embodiments, one $R^6$ is trityl (Tr) and the other $R^6$ is H. In certain embodiments, both $R^6$ are H.

In certain embodiments of Formulas II, II', III, III', V, VIII, IX, IX', XI, or XI', each $R^1$ or $R^{1'}$ is methyl, ethyl, propyl, butyl, pentyl, or hexyl. In certain embodiments, both $R^1$ or $R^{1'}$ are methyl. In certain embodiments, the two $R^1$'s or $R^{1'}$'s taken together form a $C_2$ or $C_3$ alkylene moiety to form a heterocyclic ring selected from

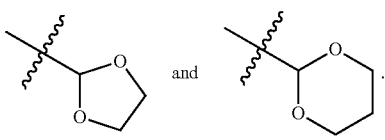 [SMILES: *C1OCCO1 ; *C1OCCCO1]

In certain embodiments of Formulas I, II, II', III, III', V, V', VII, or VII', each of $Y^1$, $Y^2$, and $Y^3$ is hydrogen. In certain embodiments of Formulas I, II, II', III, III', V, V', VII, or VII', each of $Y^1$, $Y^2$, and $Y^3$ is deuterium. In certain embodiments of Formulas I, II, III, V, or VII, $Y^1$ is hydrogen and each of $Y^2$ and $Y^3$ is deuterium. In certain embodiments of Formulas I, II, II', III, III', V, V', VII, or VII', $Y^1$ is at least 95% hydrogen. In certain embodiments of Formulas I, II, II', III, III', V, V', VII, or VII', $Y^1$ is at least 96% hydrogen. In some embodiments, $Y^1$ is at least 97% hydrogen. In some embodiments, $Y^1$ is at least 98% hydrogen. In some embodiments, $Y^1$ is at least 99% hydrogen.

In certain embodiments, a compound of Formula I, II, II', III, III', V, V', VII, VII', XI or XI' has deuterium incorporation at each designated deuterium atom of at least 90%. In certain embodiments, a compound of Formula I, II, II', III, III', V, V', VII, VII', XI or XI' has deuterium incorporation at each designated deuterium atom of at least 95%. In certain embodiments, a compound of Formula I, II, II', III, III', V, V', VII, VII', XI or XI' has deuterium incorporation at each designated deuterium atom of at least 97.5%. In certain embodiments, a compound of Formula I, II, II', III, III', V, V', VII, VII', XI or XI' has deuterium incorporation at each designated deuterium atom of at least 98%. In certain embodiments, a compound of Formula I, II, II', III, III', V, V', VII, VII', XI or XI' has deuterium incorporation at each designated deuterium atom of at least 99%.

In certain aspects, the invention provides methods and compounds for the preparation of a compound of Formula I:

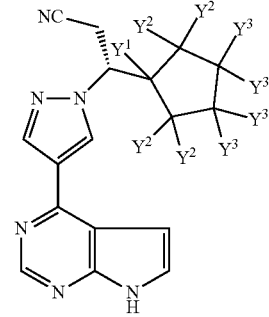

Formula I or a salt thereof;

comprises the steps of:

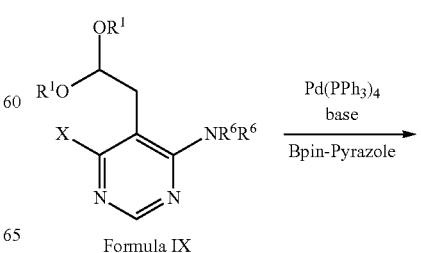

Formula IX

-continued

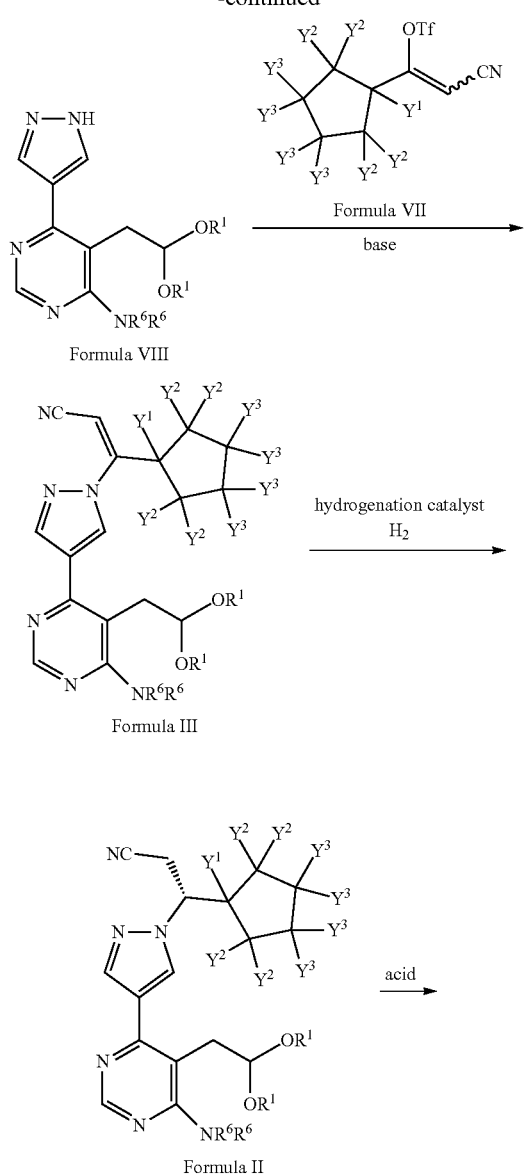

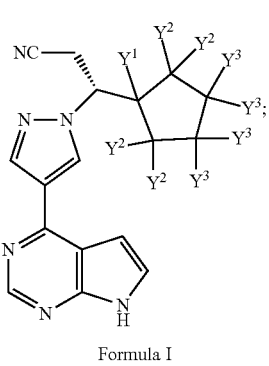

Formula I wherein each of $Y^1$, $Y^2$, $Y^3$, $R^1$ and $R^6$ is defined as in Formula II, and each reactant and reaction condition is defined as for each transformation herein. In certain embodiments, a compound of Formula III is converted to a compound of Formula II through an intermediate compound of Formula XI:

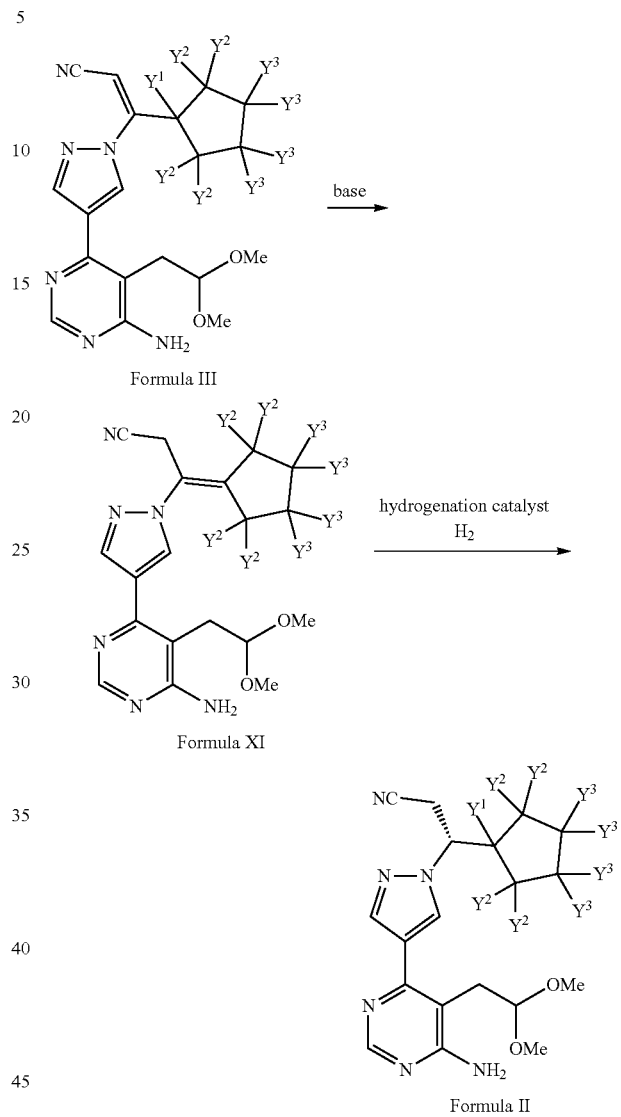

The invention further provides methods of preparing compounds of the invention, for example, a compound of Formula I, or a compound of Formula II or II', or a compound of Formula III or III', or a compound of Formula VII, or a compound of Formula VIII or VIII', using more than one of the methods described herein. For example, a the invention provides a method of making a compound of Formula I by first preparing a compound of VIII or VIII' as disclosed herein, followed by preparing a compound of Formula III or III' from the compound of Formula VIII or VIII' as disclosed herein, followed by preparing the compound of Formula I from the compound of Formula III or III' as described herein.

The invention further provides methods of preparing compounds of the invention, for example, a compound of Formula I, or a compound of Formula II or II', or a compound of Formula III or III', or a compound of Formula VII, or a compound of Formula VIII or VIII', using more than one of the methods described herein. For example, a the invention provides a method of making a compound of Formula I by first preparing a compound of VIII or VIII' as disclosed herein, followed by preparing a compound of Formula III or III' from the compound of Formula VIII or VIII' as disclosed herein, followed by preparing the compound of Formula I from the compound of Formula III or III' as described herein.

Certain aspects of the processes of the present invention provide a compound of Formula I, wherein each of $Y^1$, $Y^2$, and $Y^3$ is defined as in Formula II (e.g., CTP-543 or ruxolitinib) or a pharmaceutically acceptable salt thereof (e.g., CTP-543 phosphate or ruxolitinib phosphate), which is substantially free of impurities. In some embodiments, the compound of Formula I has a purity of at least 98%, 98.5%, 99.0%, 99.5%, 99.8%, 99.9%, or 99.95% (as measured by HPLC and/or NMR). In some embodiments, a compound of Formula I comprises less than 0.30%, less than 0.15%, less than 0.10%, less than 0.05%, less than 0.01%, less than 0.005%, less than 0.001%, less than 0.0005%, or less than 0.0001% of a compound of Formula X, wherein each of $Y^1$, $Y^2$, and $Y^3$ is defined as in Formula II:

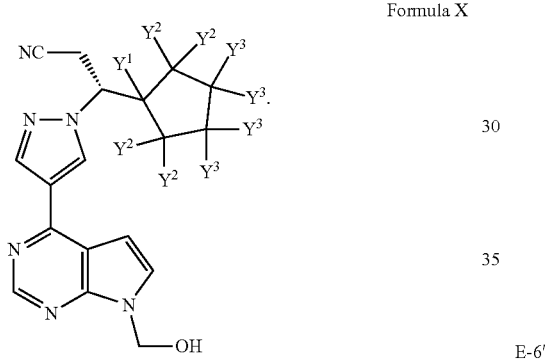

Formula X

Some embodiments provide CTP-543 comprising less than 0.30%, less than 0.15%, less than 0.10%, less than 0.05%, less than 0.01%, less than 0.005%, less than 0.001%, less than 0.0005%, or less than 0.0001% of a compound represented by the structure:

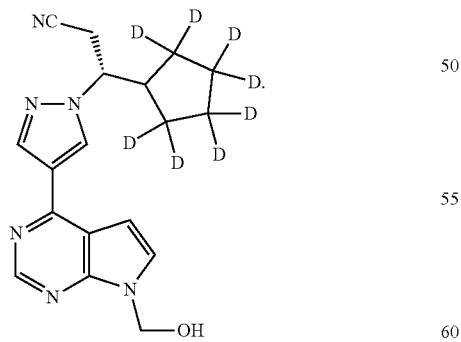

Some embodiments provide ruxolitinib comprising less than 0.30%, less than 0.15%, less than 0.10%, less than 0.05%, less than 0.01%, less than 0.005%, less than 0.001%, less than 0.0005%, or less than 0.0001% of a compound represented by the structure:

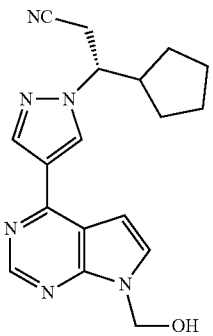

In another aspect, the invention provides a method of purifying a compound of Formula E-6:

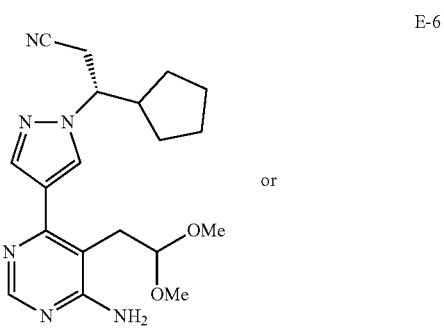

E-6 or

E-6'

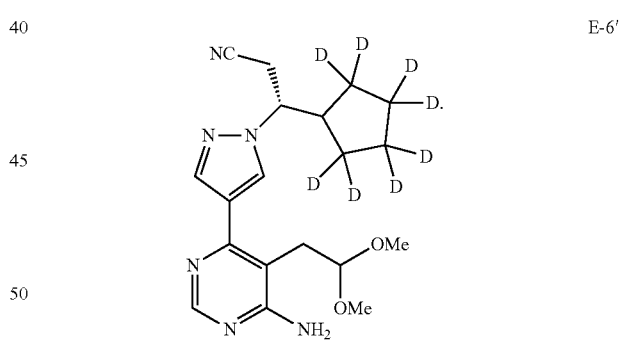

E-6'

The method comprises contacting the compound of Formula E-6 or E-6' with an acid to form a salt of the compound of Formula E-6 or E-6', and crystallizing a crystalline salt of the compound of Formula E-6 or E-6'. In certain embodiments, the acid is a chiral acid, such as D-dibenzoyltartaric acid. In certain embodiments, the step of contacting the compound of Formula E-6 or E-6' with an acid is performed in a solvent; in certain embodiments, the solvent is trifluoroethanol, acetonitrile, isopropyl acetate, or a mixture thereof. In certain embodiments, the crystalline salt of the compound of Formula E-6 or E-6' has an enantiomeric ratio (er) of at least 99:1, or at least 99.5:0.5, or at least 99.6:0.4.

In another aspect, the invention provides a method of purifying Compound 15:

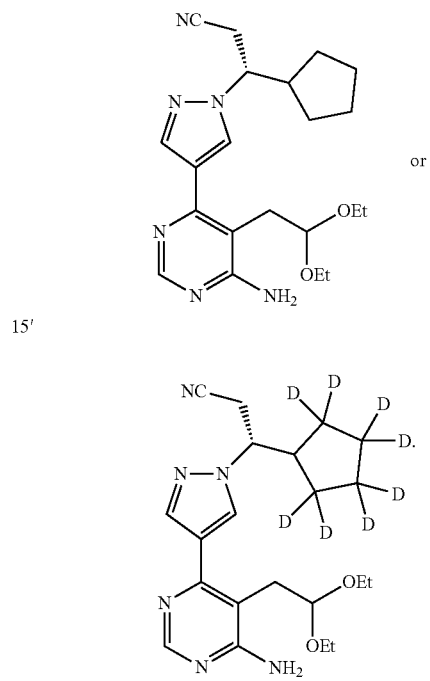

The method comprises contacting Compound 15 or 15' with an acid to form a salt of the compound of Formula 15 or 15', and crystallizing a crystalline salt of the compound of Formula 15 or 15'. In certain embodiments, the acid is a chiral acid, such as D-dibenzoyltartaric acid. In certain embodiments, the step of contacting the compound of Formula 15 or 15' with an acid is performed in a solvent; in certain embodiments, the solvent is trifluoroethanol, acetonitrile, isopropyl acetate, or a mixture thereof. In certain embodiments, the crystalline salt of the compound of Formula 15 or 15' has an enantiomeric ratio (er) of at least 99:1, or at least 99.5:0.5, or at least 99.6:0.4.

Intermediates

Certain aspects of the present invention are directed to additional intermediates useful, e.g., in the preparation of compounds of Formula I.

In certain embodiments, the intermediate comprises a compound of Formula II:

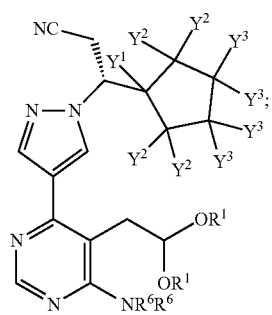

Formula II or a salt thereof;

wherein $Y^1$ is hydrogen or deuterium, each $Y^2$ is the same and is hydrogen or deuterium, and each $Y^3$ is the same and is hydrogen or deuterium; and wherein each $R^1$ is $C_1$-$C_6$ alkyl, or taken the two $R^1$s together form a $C_2$ or $C_3$ alkylene moiety; and each $R^6$ is independently selected from H or a protecting group. In certain embodiments, the intermediate comprises a compound of Formula III:

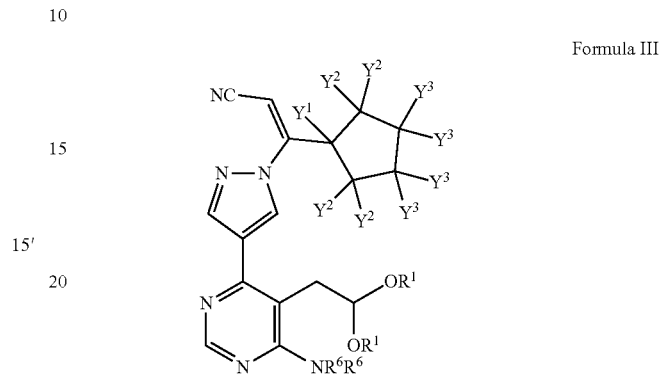

Formula III or a salt thereof;

wherein $Y^1$ is hydrogen or deuterium, each $Y^2$ is the same and is hydrogen or deuterium, and each $Y^3$ is the same and is hydrogen or deuterium; and wherein each $R^1$ is $C_1$-$C_6$ alkyl, or taken the two $R^1$s together form a $C_2$ or $C_3$ alkylene moiety; and each $R^6$ is independently selected from H or a protecting group.

In certain embodiments, the intermediate comprises a compound of Formula III:

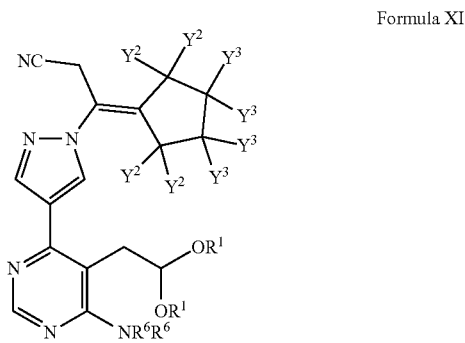

Formula XI or a salt thereof;

wherein each $Y^2$ is the same and is hydrogen or deuterium, and each $Y^3$ is the same and is hydrogen or deuterium; and wherein each $R^1$ is $C_1$-$C_6$ alkyl, or taken the two $R^1$s together form a $C_2$ or $C_3$ alkylene moiety; and each $R^6$ is independently selected from H or a protecting group.

In certain embodiments of Formula II, III, or XI, the protecting group is selected from t-butoxycarbonyl (Boc), triflyl (Tf, $SO_2$—$CF_3$), trifluoroacetyl ($F_3$—Ac), and trityl (Tr, $CHPh_3$). In certain embodiments, both $R^6$ are t-butoxycarbonyl (Boc). In certain embodiments, one $R^6$ is t-butoxycarbonyl (Boc) and the other $R^6$ is H. In certain embodiments, one $R^6$ is triflyl (Tf) and the other $R^6$ is H. In certain embodiments, one $R^6$ is trifluoroacetyl ($F_3$—Ac) and the other $R^6$ is H. In certain embodiments, one $R^6$ is trityl (Tr) and the other $R^6$ is H. In certain embodiments, both $R^6$ are H.

In certain embodiments of Formula II, III, or XI, $R^1$ is methyl, ethyl, propyl, butyl, pentyl, or hexyl. In certain embodiments of Formula II, III, or XI, $R^1$ is methyl or ethyl. In certain embodiments of Formula II, III, or XI, both $R^1$ are methyl.

In another embodiment, the invention provides a compound of Formula VII:

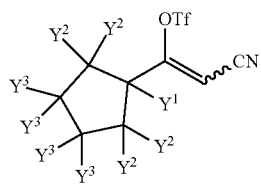

Formula VII wherein $Y^1$ is hydrogen or deuterium, each $Y^2$ is the same and is hydrogen or deuterium, and each $Y^3$ is the same and is hydrogen or deuterium; and OTf is triflate ($-OSO_2CF_3$). In certain embodiments, the compound of Formula VII is a compound of Formula VIIa:

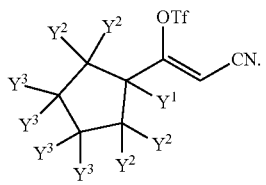

Formula VIIa

In certain embodiments, the compound of Formula VII is a compound of Formula VIIb:

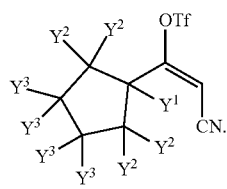

Formula VIIb

In certain embodiments, the compound of Formula VII is a mixture of the compounds of Formula VIIa and Formula VIIb.

In certain embodiments of Formula II, III or VII, or Formula I, II', II', or VII', each of $Y^1$, $Y^2$, and $Y^3$ is hydrogen. In certain embodiments of Formula II, III or VII, or Formula I, II', II', or VII', each of $Y^1$, $Y^2$, and $Y^3$ is deuterium. In certain embodiments of Formula II, III or VII, or Formula I, II', II', or VII', $Y^1$ is hydrogen and each of $Y^2$ and $Y^3$ is deuterium. In certain embodiments of Formula II, III or VII, or Formula I, II', II', or VII', $Y^1$ is at least 95% hydrogen. In certain embodiments of Formula II, III or VII, or Formula I, II', II', or VII', $Y^1$ is at least 96% hydrogen. In some embodiments, $Y^1$ is at least 97% hydrogen. In some embodiments, $Y^1$ is at least 98% hydrogen. In some embodiments, $Y^1$ is at least 99% hydrogen.

In certain embodiments, a compound of Formula II, III, VII, or XI or Formula I, II', II', VII', or XI' has deuterium incorporation at each designated deuterium atom of at least 90%. In certain embodiments, a compound of Formula II, III, VII, or XI, or Formula I, II', II', VII', or XI' has deuterium incorporation at each designated deuterium atom of at least 95%. In certain embodiments, a compound of Formula II, III, VII, or XI, or Formula I, II', II', VII', or XI' has deuterium incorporation at each designated deuterium atom of at least 97%. In certain embodiments, a compound of Formula II, III, VII, or XI, or Formula I, II', II', VII', or XI' has deuterium incorporation at each designated deuterium atom of at least 98%. In certain embodiments, a compound of Formula II, III, VII, or XI, or Formula I, II', II', VII', or XI' has deuterium incorporation at each designated deuterium atom of at least 99%.

In another set of embodiments of the formulas described herein, any atom not designated as deuterium in any of the embodiments set forth herein is present at its natural isotopic abundance.

In another embodiment, the invention provides a compound of Formula VIII:

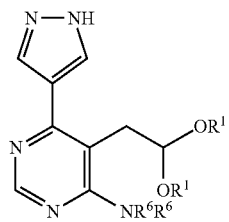

Formula VIII or a salt thereof;
wherein each $R^1$ is methyl, propyl, butyl, pentyl, hexyl, or taken together the two $R^1$'s form a $C_2$ or $C_3$ alkylene moiety; and each $R^6$ is independently selected from H or a protecting group.

In certain embodiments of Formula VIII, the protecting group is selected from t-butoxycarbonyl (Boc), triflyl (Tf, $SO_2-CF_3$), trifluoroacetyl ($F_3-Ac$), and trityl (Tr, $CHPh_3$). In certain embodiments, both $R^6$ are t-butoxycarbonyl (Boc). In certain embodiments, one $R^6$ is t-butoxycarbonyl (Boc) and the other $R^6$ is H. In certain embodiments, one $R^6$ is triflyl (Tf) and the other $R^6$ is H. In certain embodiments, one $R^6$ is trifluoroacetyl ($F_3-Ac$) and the other $R^6$ is H. In certain embodiments, one $R^6$ is trityl (Tr) and the other $R^6$ is H. In certain embodiments, both $R^6$ are H. In certain embodiments of Formula VIII, both $R^1$ are methyl.

In another embodiment, the invention provides a compound of Formula IX:

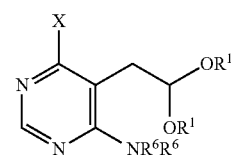

Formula IX or a salt thereof;
wherein each $R^1$ is methyl, propyl, butyl, pentyl, hexyl, or taken together the two $R^1$'s form a $C_2$ or $C_3$ alkylene moiety; each $R^6$ is independently selected from H or a protecting group; and X is I, Br, Cl, or triflate.

In certain embodiments of Formula IX, the protecting group is selected from t-butoxycarbonyl (Boc), triflyl (Tf, $SO_2$—$CF_3$), trifluoroacetyl ($F_3$—Ac), and trityl (Tr, $CHPh_3$). In certain embodiments, both $R^6$ are t-butoxycarbonyl (Boc). In certain embodiments, one $R^6$ is t-butoxycarbonyl (Boc) and the other $R^6$ is H. In certain embodiments, one $R^6$ is triflyl (Tf) and the other $R^6$ is H. In certain embodiments, one $R^6$ is trifluoroacetyl ($F_3$—Ac) and the other $R^6$ is H. In certain embodiments, one $R^6$ is trityl (Tr) and the other $R^6$ is H. In certain embodiments, both $R^6$ are H. In certain embodiments of Formula IX, both $R^1$ are methyl. In certain embodiments of Formula XI, $R^1$ is not ethyl.

In certain embodiments of Formula IX, X is Cl.

In another embodiment, the invention provides a compound of Formula IX':

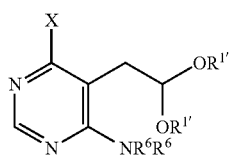

Formula IX' or a salt thereof;

wherein each $R^{1'}$ is $C_1$-$C_{10}$ alkyl (e.g., methyl or ethyl), or $C_2$-$C_{10}$ alkenyl (e.g., allyl), or the two $R^{1'}$s, taken together with the oxygen atoms to which they are attached, form a 5-7-membered heterocyclic ring which may optionally be substituted (e.g., a 1,3-dioxolan-2-yl ring, or a 1,3-dioxan-2-yl ring, or a 1,3-benzodioxolan-2-yl ring, which may each be substituted with, e.g., one or more methyl groups); and each $R^6$ is independently selected from H and a protecting group; and X is I, Br, Cl, or triflate. In certain embodiments, each $R^{1'}$ is $C_1$-$C_{10}$ alkyl; in further embodiments, each $R^{1'}$ is methyl or ethyl. In certain embodiments, each $R^6$ is H. In certain embodiments, one $R^6$ is H and one $R^6$ is a protecting group. In certain embodiments, each $R^6$ is a protecting group. In certain embodiments, the protecting group is a t-butoxycarbonyl group. In certain embodiments, the base is selected from potassium carbonate and dibasic sodium phosphate dihydrate.

In certain embodiments of Formula IX, the protecting group is selected from t-butoxycarbonyl (Boc), triflyl (Tf, $SO_2$—$CF_3$), trifluoroacetyl ($F_3$—Ac), and trityl (Tr, $CPh_3$). In certain embodiments, both $R^6$ are t-butoxycarbonyl (Boc). In certain embodiments, one $R^6$ is t-butoxycarbonyl (Boc) and the other $R^6$ is H. In certain embodiments, one $R^6$ is triflyl (Tf) and the other $R^6$ is H. In certain embodiments, one $R^6$ is trifluoroacetyl ($F_3$—Ac) and the other $R^6$ is H. In certain embodiments, one $R^6$ is trityl (Tr) and the other $R^6$ is H. In certain embodiments, both $R^6$ are H. In certain embodiments of Formula IX', both $R^1$ are methyl. In certain embodiments of Formula IX', X is Cl. In certain embodiments of Formula XI', $R^{1'}$ is not ethyl.

The synthesis of compounds of Formulas II-XII may be readily achieved by synthetic chemists of ordinary skill by reference to the Exemplary Synthesis disclosed herein.

Such methods can be carried out utilizing corresponding deuterated and optionally, other isotope-containing reagents and/or intermediates to synthesize the compounds delineated herein, or invoking standard synthetic protocols known in the art for introducing isotopic atoms to a chemical structure.

As used herein, the terms method and process are interchangeable.

EXAMPLES

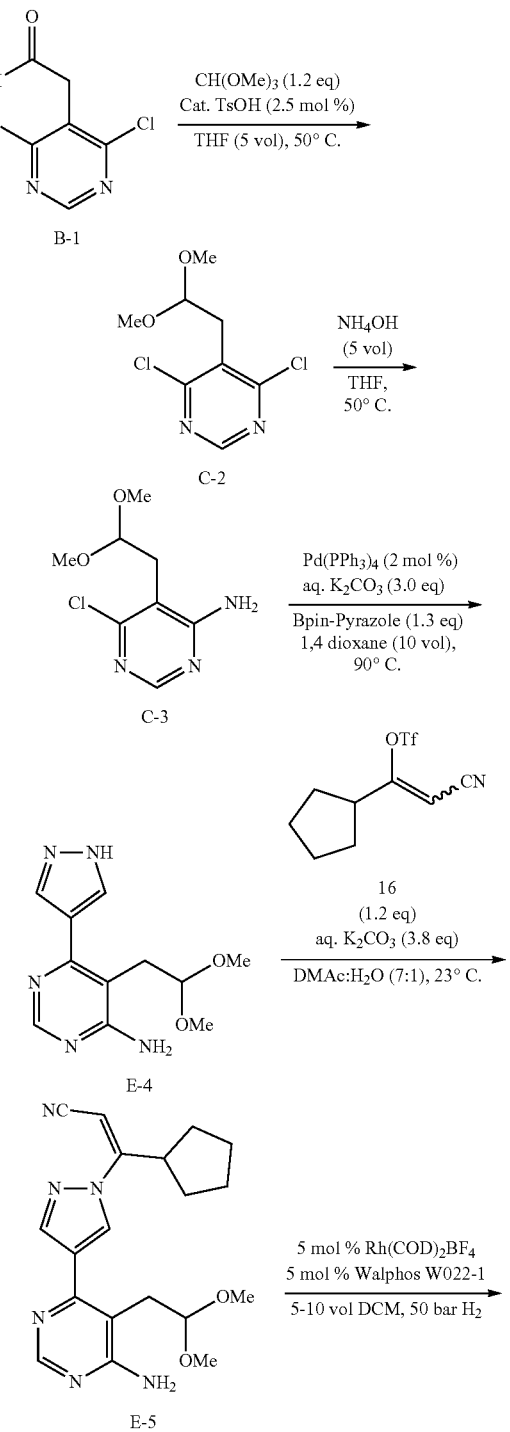

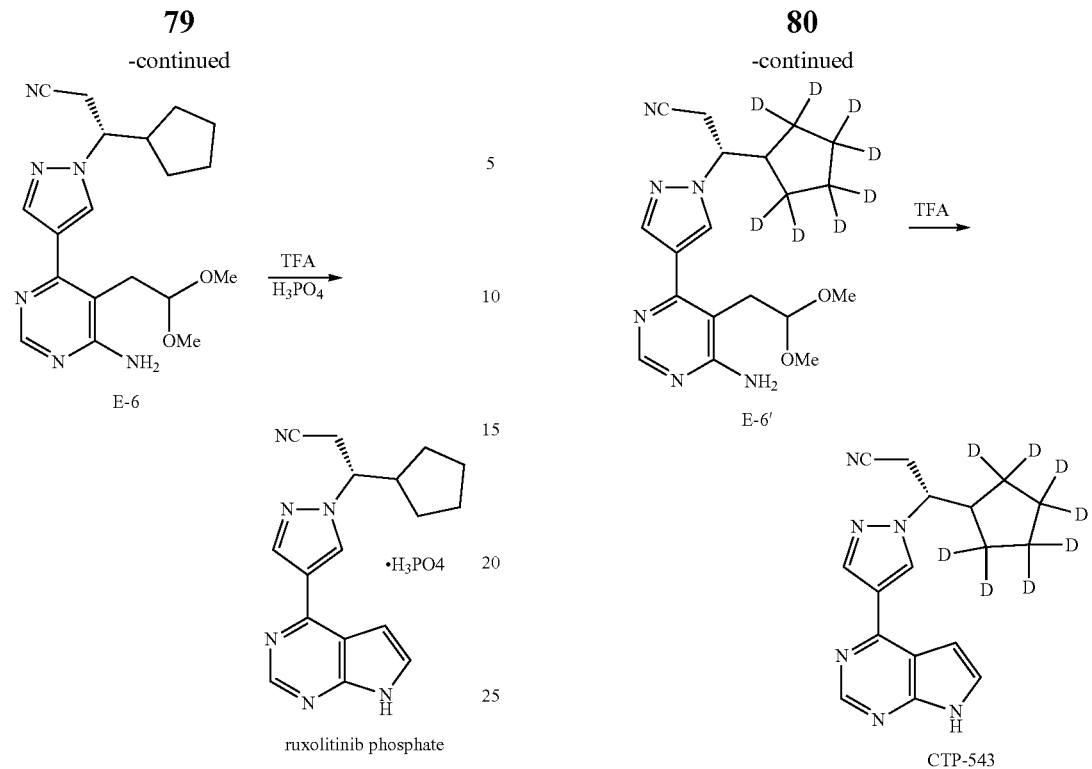
ruxolitinib phosphate
CTP-543
Scheme 2: Preparation of D8-Ruxolitinib (CTP-543)
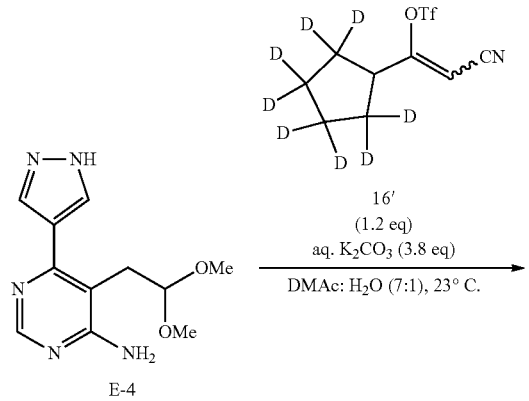
Scheme 3: Preparation of enol triflates (2-Cyano-1-(cyclopentyl)vinyl trifluoromethanesulfonate and 2-Cyano-1-(2,2,3,3,4,4,5,5-D8-cyclopentyl)vinyltrifluoromethanesulfonate
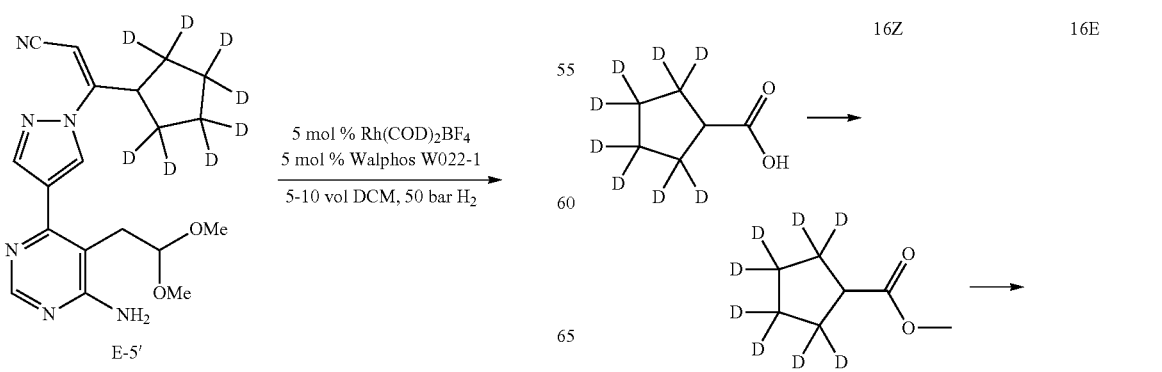

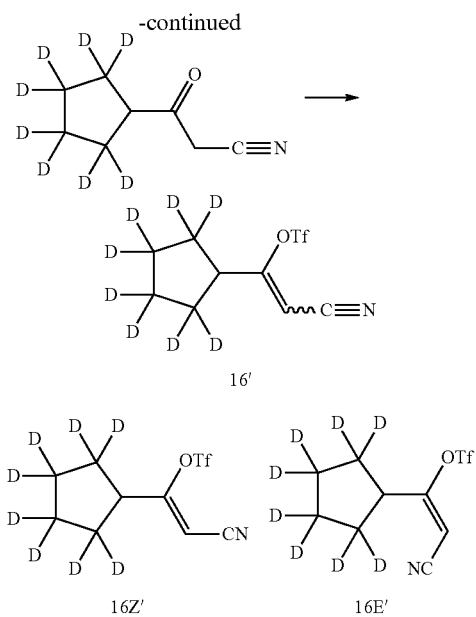

16'

16Z'  16E'

As shown in Scheme 3, above, 2-Cyano-1-(cyclopentyl) vinyl trifluoromethanesulfonate (enol triflate 16) can be prepared from the corresponding beta-ketonitrile, which in turn can be prepared from cyclopentanecarboxylic acid, methyl ester (readily available from the commercially available cyclopentanecarboxylic acid). Enol triflate 16 is synthesized as a mixture of Z and E isomers, which may optionally be separated into 16Z and 16E. Similarly, deuterated enol triflate 16' can be prepared from corresponding deuterated precursors. Enol triflate 16' is synthesized as a mixture of Z and E isomers, which may optionally be separated into 16Z' and 16E'. Deuterated enol triflates 16', 16Z', or 16E' may be substituted for enol triflates 16, 16Z, or 16E in any synthesis disclosed herein to produce CTP-543 or pharmaceutically acceptable salts thereof.

A) Preparation of beta-ketonitrile

To a 3-neck, 500-mL European-style flask equipped with a mechanical stirrer and thermocouple, and flushed with nitrogen was added a solution of NaHMDS in THF via a syringe (173 mL, 343.2 mmol, 2.2 eq; 2M solution in THF), then the yellow solution was cooled to −14.6° C. under $N_2$. To the cold solution was added a solution of methyl cyclopentanecarboxylate (20 g, 156 mmol, 1.0 eq) in MeCN (9.8 mL, 187.2 mmol, 1.2 eq) in MeCN (9.8 mL, 187.2 mmol, 1.2 eq), dropwise via a syringe; rinsed the flask with anhydrous THF (10 mL) and added the rinse to the reaction mixture, the addition time was 50 min, during which period the internal temperature was kept below −3° C. and it became cloudy and thin slurry. The mixture was agitated at ca. −10° C. for 10 min, then was warmed up to 20° C. for over a period of 1 h. The agitation was continued at 24° C. for overnight, a very thick slurry formed with a crusty top layer. The mixture was cooled to ~3° C., then was added cold 6 N HCl (~5° C., 130 mL) portion-wise to keep internal temperature mainly below 27° C. After the quench was finished, the mixture was agitated and warmed up to 22° C., transferred to a separatory funnel to collect organic and aqueous layers. The aqueous layer (140 mL) was extracted with MTBE (2×55 mL). The combined organic layers was washed with satd. $NaHCO_3$ (60 mL), 1N HCl (2×50 mL), 20% aq. NaCl (50 mL), then lastly water (2×50 mL). The resulting organic layer was concentrated in a rotovap (45° C.) to remove organic volatiles, and more MTBE (2×) was used to azeotrope off residual water. The crude product was obtained as an amber liquid, weight=20.09 g. $^1$H NMR ($CDCl_3$) showed the desired product with a very clean profile. Molar yield=93%.

$^1$H NMR ($CDCl_3$) δ: 3.50 (s, 3H), 3.07 (quintet, J=8 Hz, 1H), 1.98-1.54 (m, 8H)

B) Preparation of 2-Cyano-1-(cyclopentyl)vinyl trifluoromethanesulfonate 16

To a 1-L jacketed reactor equipped with a mechanical stirrer and thermocouple was added β-ketonitrile solution in toluene (50 g, 364 mmol, solution weight=213.6 g, w %=23.4%) under nitrogen. The solution was cooled to 0° C., followed by addition of N-Methylmorpholine (50.1 g, 455.5 mmol, 1.25 eq) while keeping the batch temperature below 2° C. At ~0° C., the mixture was added $Tf_2O$ (111.5 g, 395.2 mmol, 1.09 eq) dropwise over a period of 80 minutes to keep the batch temperature below 5° C. The reaction mixture was agitated at cold for ~2 hrs. GC analysis showed >99.8% conversion. To the cold mixture was added water (300 mL), the resulting cold bi-phasic mixture was warmed up to ambient temperature. The upper organic layer was collected and washed with water (300 mL), then was partially concentrated in a rotovap to obtain enol-triflate solution in toluene (163.2 g).

$^1$H NMR ($CDCl_3$) assay analysis indicated w/w % for enol-triflate 16 was 55%, as a mixture of E/Z isomers (Z:E~89:11). The corrected weight=88.9 g, molar yield=91%.

$^1$H NMR ($CDCl_3$) δ: 16Z-isomer—5.33 (d, J=4 Hz, 1H), 2.99 (dq, J=8 Hz, 4 Hz, 1H), 2.18-1.99 (m, 2H), 1.89-1.68 (m, 4H), 1.67-1.51 (m, 2H); 16E-isomer—5.54 (s, 1H), 3.37 (q, J=8 Hz, 1H), 2.18-1.51 (m, 8H).

The corresponding D8-deuterated compound 16' (2-Cyano-1-(2,2,3,3,4,4,5,5-D8-cyclopentyl)vinyl trifluoromethanesulfonate) can be prepared using similar procedures starting from methyl 2,2,3,3,4,4,5,5-D8-cyclopentanecarboxylic acid (which can be prepared in a manner analogous to the preparation of 1,2,2,3,3,4,4,5,5-D9-cyclopentanecarboxylic acid; see, e.g., U.S. Pat. No. 9,249,149). Similarly to enol triflate 16, 2-cyano-1-(2,2,3,3,4,4,5,5-D8-cyclopentyl)vinyl trifluoromethanesulfonate 16' is synthesized as a mixture of isomers, which may optionally be separated into 16Z' and 16E'.

Scheme 4: Preparartion of Ruxolitinib (free base)

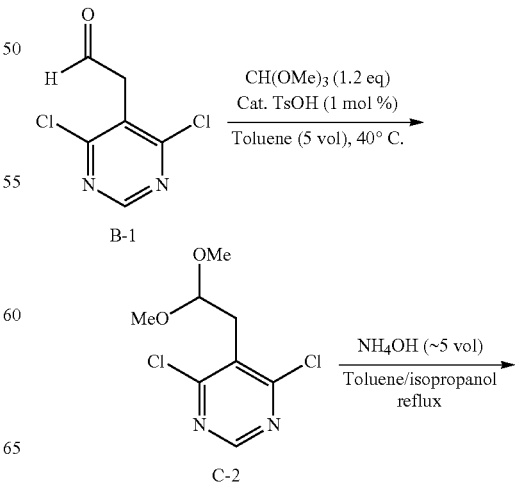

-continued

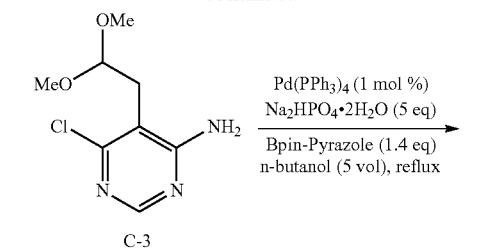

C-3

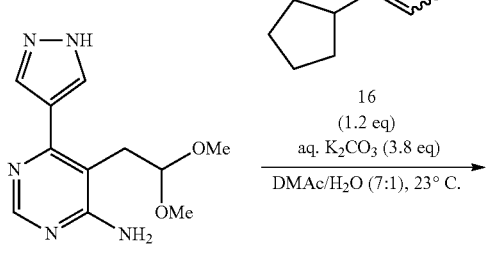

E-4

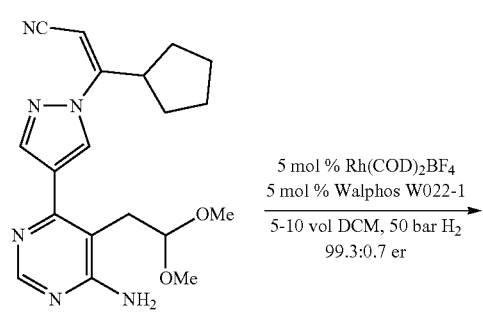

E-5

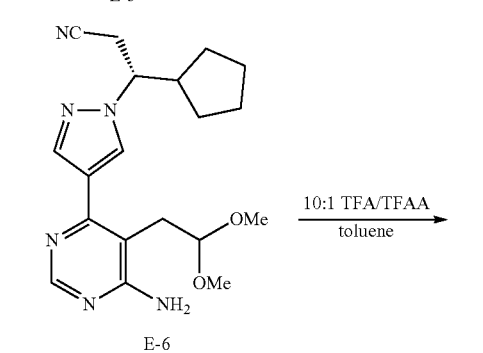

E-6

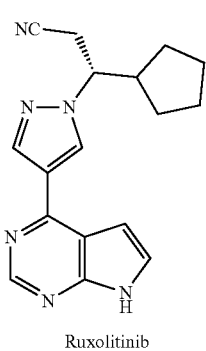

Ruxolitinib

Example 1

Step 1: Preparation of 4,6-Dichloro-5-(2,2-dimethoxyethyl)pyrimidine (C-2)

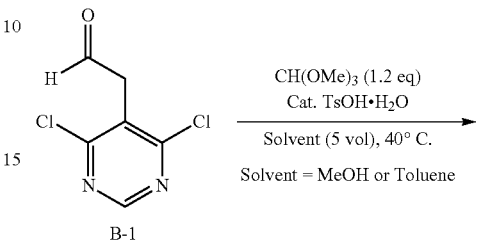

B-1

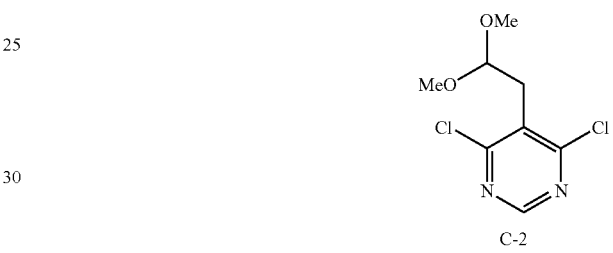

C-2 a) MeOH, TsOH (10 mol %):

A mixture of compound B-1 (10 g, 52.4 mmol), trimethyl orthoformate (6.67 g, 62.8 mmol, 1.2 eq), and TsOH·H$_2$O (0.902 g, 5.24 mmol, 0.10 eq) in MeOH (50 ml) was stirred at 40° C. for 1.5 h. The reaction mixture was cooled to room temperature, aqueous Na$_2$CO$_3$ (20 mL) was added to adjust pH to 8 and extracted with EtOAc (2×50 ml). The combined organic extract was washed with water (20 ml), brine (15 ml) and dried over anhydrous Na$_2$SO$_4$, filtered and concentrated under reduced pressure to give C-2 (11.9 g, 96% yield) as brown solid.

b) Toluene, TsOH (1 mol %):

To suspension of compound B-1 (635 g, 88% assay, 2.93 mol) in toluene (2988 g) was charged trimethyl orthoformate (371 g, 3.50 mol, 1.2 eq). The batch was cooled to 20° C. and solid TsOH·H$_2$O (5.76 g, 0.03 mol, 0.01 eq) was charged. Batch temperature was maintained by lowering the jacket temperature to 16° C. for 10 minutes during a minor exotherm, before adjustment to 20° C. After stirring the suspension for 2 hours at 20° C., the jacket temperature was raised to 40° C. for 11.5 hours before returning the jacket to 20° C. HPLC indicated consumption of starting material. Assay of the brown solution provided a concentration of approximately 136 mg/mL C-2 (total volume approximately 4.40 L, 597-631 g product, 86% yield).

The batch was filtered through a coarse glass frit before use in the next step.

Step 2: Preparation of 6-Chloro-5-(2,2-dimethoxy-ethyl)pyrimidin-4-amine (C-3)

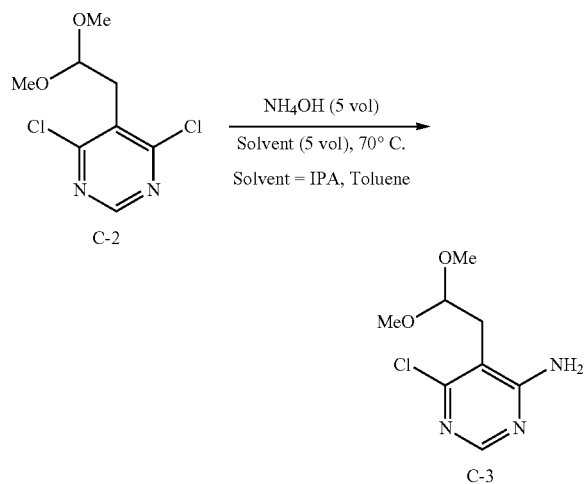

a) Isopropanol (iPA):

A mixture of compound C-2 (6.0 g, 25.3 mmol) and NH₄OH (30 ml) in iPA (30 ml) was stirred at 70° C. for 8 h. The reaction mixture was then cooled to room temperature and solvent was removed under reduced pressure. The residue was extracted with EtOAc (2×60 ml). The combined organic extract was washed with water (20 ml), brine (15 ml) and dried over anhydrous Na₂SO₄, filtered and concentrated under reduced pressure to give C-3 (5.3 g, 96%) as pale brown solid.

b) Toluene/iPA:

To a toluene solution of C-2 (4.40 L, approximately 136 mg/mL) in a 10 L jacketed glass reactor (Jacket temperature 20° C., stir rate 130 RPM, condenser temperature: −5° C.) was charged ammonium hydroxide solution (235 g). The mixture presented an exotherm that raised batch temperature 3° C. The mixture was stirred for 4 hours before agitation was paused to allow removal of the aqueous layer (dark brown, lower layer, 376 g). The reactor jacket was set to 40° C. Ammonium hydroxide solution (298 g) was charged and the batch was held for 2 days. Additional ammonium hydroxide (200 g) and isopropanol (4 L) were charged, and the reactor jacket was set to 70° C. Additional ammonium hydroxide solution (421 g) was periodically added over the next 24 hours, and the reaction was deemed complete after agitation at 70° C. for 6 days. The batch was cooled to 20° C. and water (1.0 L) wash charged to the batch. Agitation was stopped and the aqueous cut was removed. The batch was discharged into a drum and treated with activated charcoal (78 g). After standing for three hours, the batch was filtered into a clean reactor. A distillation apparatus was attached and the batch was distilled to volume of 2.5 L. Toluene was charged (876 g). After additional distillation (1023 g distilled) the reactor jacket was cooled to 10° C. over 4 hours. Heptane (100 g) was charged and the batch was agitated for 4 hours. The batch was filtered with suction onto three disposable polypropylene fritted funnels to obtain a tan solid. The reactor was washed with 280 g toluene. Each filter cake was washed with 100 mL toluene. Each filter cake was dried with suction to a transferrable solid before combination into a drying tray. The solids were dried under vacuum with a nitrogen stream to yield a tan solid (343.2 g, 94.6 wt %, 55% yield.

Step 3: Preparation of 5-(2,2-Dimethoxyethyl)-6-(1H-pyrazol-4-yl)pyrimidin-4-amine (E-4)

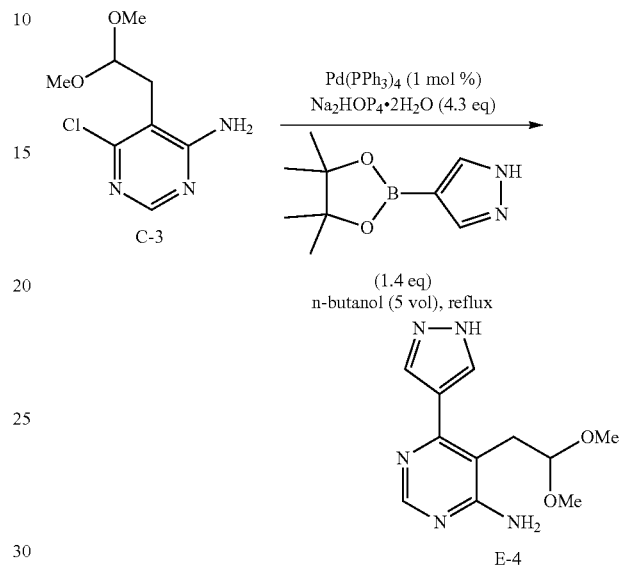

a) Small Batch

A 100 mL reactor with overhead stirring and nitrogen purge was charged with C-3 (9.95 g), 4-(4,4,5,5-tetramethyl-1,3,2-dioxaborolan-2-yl)-1H-pyrazole (12.12 g), and dibasic sodium phosphate dihydrate (35.02 g). n-Butanol (50 mL) was charged to the reactor and the reactor headspace was purged while stirring for 15 minutes. Tetrakis(triphenylphosphine)palladium(0) (0.498 g) was charged to the reactor. The reactor jacket was set to 100° C. while agitating. The reaction appeared complete (HPLC/UV, 210 nm) after 16.5 hours at reflux. The batch was cooled to 25° C. before addition of 50 mL of water. The batch was agitated until all salts had dissolved. The batch was transferred to a separatory funnel and the phases were allowed to separate. The aqueous layer was removed from the organics. The organics were returned to the reactor followed by a rinse of n-butanol (30 mL). A distillation apparatus was attached and the batch was distilled until 35 mL had been collected. The batch was filtered to remove precipitated salts and returned to a clean reactor with a n-butanol rinse (10 mL). The batch was distilled to a total volume of 20 mL. The reactor was cooled to 20° C. while adding n-butanol (20 mL) and heptane (80 mL). Seed crystals of E-4 were added, and the batch was heated to 50° C. before being cooled to 25° C. over 10 minutes. The suspension was filtered with suction. The filter cake was washed twice with a 1:5 mixture of n-butanol:heptane (25 mL) and dried with suction for an hour to provide a brick-red solid containing a 2:1 molar mixture of E-4 and pinacol (9.848 g, 70%). The pinacol can be removed by dissolving the product in n-butanol and continuously distilling n-butanol until pinacol is azeotropically removed.

b) Large Batch

A 500 mL reactor with overhead stirring and nitrogen purge was charged with C-3 (50.32 g), 4-(4,4,5,5-tetramethyl-1,3,2-dioxaborolan-2-yl)-1H-pyrazole (60.14 g), dibasic sodium phosphate dihydrate (170.76 g) and n-butanol (250 mL) was charged to the reactor and the reactor headspace was purged while stirring for 5 minutes. Tetrakis(triphenylphosphine)palladium(0) (2.62 g) was charged to the reactor. The reactor jacket was set to 100° C. while agitating. The reaction appeared complete (HPLC/UV, 210 nm) after 13 hours. Water (250 mL) was charged by pump over 1 hour. The batch was agitated until all salts had dissolved, then cooled to 20° C. Agitation was halted and the phases were allowed to separate. The aqueous layer was discharged and discarded. A distillation apparatus was attached to the reactor and the batch was distilled under reduced pressure with a jacket temperature of 100° C. until the total reaction volume reached about 200 mL. The batch was cooled to 40° C. before addition of heptane (800 mL) over 1 hour. The jacket was set to 100° C. and the batch was warmed at this temperature for 4 hours before cooling to 20° C. over 4 hours. The resultant suspension was filtered and dried with suction for 1 hour to provide E-4 (52.0 g, 85% w/w, 77% yield) containing 3.3 wt % pinacol.

The batch was dissolved in 500 mL methanol, filtered, and returned to a clean 500 mL reactor. The batch was distilled to 200 mL total volume. Tetrahydrofuran (800 mL) was added and the batch was distilled to a total volume of 200 mL. Heptane (100 mL) was added. The suspension was filtered and the filter cake was washed with 1:1 THF/Heptane (50 mL). The filter cake was dried with suction for 1 hour to provide E-4 a tan powder (41.4 g, 88% w/w, 82% recovery) with <0.1% w/w pinacol. Acetonitrile (100 mL) was charged to a portion of the resultant low-pinacol E-4 (21.4 g), The batch was warmed to 40° C. while stirring, before cooling to 23° C. over 1 hour. The suspension was filtered and dried with suction for 2 hours to provide purified E-4 (19.04 g, 94% w/w, 96% recovery).

$^1$H-NMR (400 MHz, 5% Acetic Acid-$d_4$ in Methanol-$d_4$): δ 8.31 (s, 1H), 8.07 (s, 2H), 4.70 (t, J=5.2 Hz, 1H), 3.40 (s, 6H), 2.98 (d, J=5.2 Hz, 2H).

$^{13}$C-NMR (101 MHz, 5% Acetic Acid-$d_4$ in Methanol-$d_4$): δ 165.52, 156.08, 155.64, 136.00, 119.25, 111.03, 105.62, 54.84, 33.17.

c) Alternative Reaction Conditions to Form E-4:

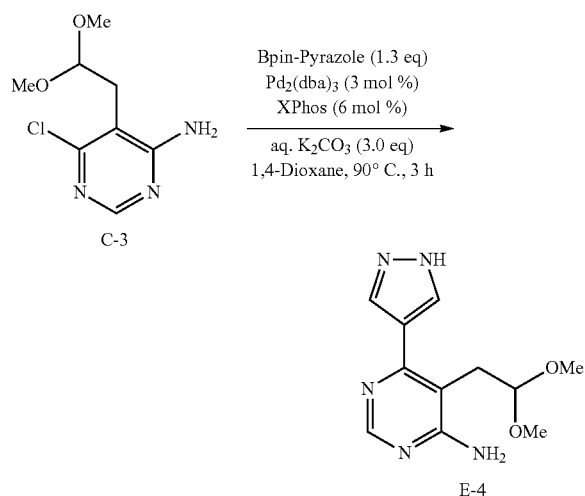

To a mixture of C-3 (0.5 g, 2.3 mmol) and BPin-Pyrazole (0.58 g, 2.99 mmol, 1.3 eq) in dioxane (5 ml) was added 2 ml of aq. K$_2$CO$_3$ (0.952 g, 6.89 mmol, 3.0 eq) at room temperature. The solution was degassed by passing a stream of nitrogen through the solution for 15 minutes before being treated with Pd$_2$(dba)$_3$ (32 mg, 0.0344 mmol, 0.03 eq) and XPhos (35 mg, 0.069 mmol, 0.06 eq). The resulting reaction mixture was then heated at 90° C. for 3 hour. The reaction mixture was brought to room temperature then diluted with ethyl acetate (30 ml) and water (15 ml). The two layers were separated, and the aqueous layer was further extracted with ethyl acetate (10 ml). The combined organic extract was washed with water (2×5 ml), brine (10 ml), dried over anhydrous Na$_2$SO$_4$, filtered and concentrated under reduced pressure. The crude residue was purified by using ISCO to give E-4 as a white solid (0.47 g, 82% yield).

Step 4: Preparation of (Z)-3-(4-(6-Amino-5-(2,2-dimethoxyethyl)pyrimidin-4-yl)-1H-pyrazol-1-yl)-3-cyclopentylacrylonitrile (E-5)

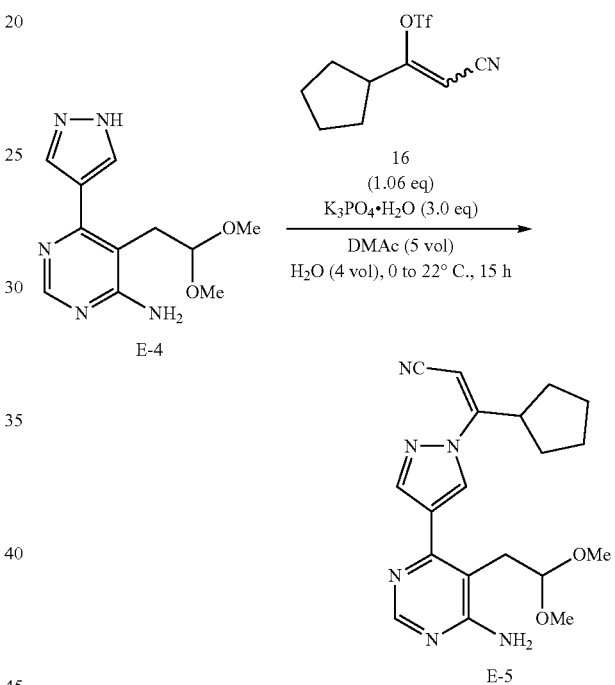

To a stirred solution of compound E-4 (3 g, 11.4 mmol, 95% pure) and enol triflate 16 (5.37 g, 12.1 mmol, 1.06 eq, 60.8 wt % in toluene) in dimethylacetamide (DMAc, 15 mL) was added pre-dissolved K$_3$PO$_4$·H$_2$O (7.89 g, 3.0 eq) in 12 ml of water via a syringe over ~5 minutes at 0° C. The resulting bi-phasic mixture was then brought to room temperature (~22° C.) and agitated for 15 h. As the reaction progress, the reaction mixture became heterogeneous bi-phasic (product was slowly precipitated out from the reaction mixture). To this mixture was added DI water (30 mL, 10 vol), further precipitates formed. The slurry was agitated at ambient temperature for 1 hr, filtered off the solids, followed by washing wet cake with pre-mixed solution of DMAc (5 vol) and water (14 vol) (1×15 mL). The resulting beige-color wet cake was suction dried for 2 hours to give product E-5 (3.6 g, 86% yield).

Alternatively, the reaction mixture was quenched with 0.4 volumes phosphoric acid (85 wt %) to pH about 8. Five volumes DMAc was added, and the mixture was warmed to 55° C. for 30 minutes. The basic aqueous layer was separated at ~55° C., and then charged 11 volumes water over 30 min at 55° C. At the end of water addition, large amount of solids precipitated. The slurry was cooled to 22° C. over 35 min and then the solids filtered. The filter cake was washed with 5 volumes of 2:3 DMAc/water. The solid E-5 was then displacement washed with 5 volumes of water and the solid dried under vacuum suction.

$^1$H-NMR (DMSO-d6, 400 MHz): δ 8.65 (s, 1H), 8.28 (s, 1H), 8.16 (s, 1H), 6.73 (s, NH$_2$, 2H), 5.72 (s, 1H), 4.63 (t, J=4.0 Hz, 1H), 3.41 (q, J=8.0 Hz, 1H), 3.27 (s, 6H), 2.94 (d, J=4.0 Hz, 2H), 1.99-1.89 (m, 2H), 1.77-1.47 (m, 6H).

a) Alternative Reaction Conditions to Form E-5:

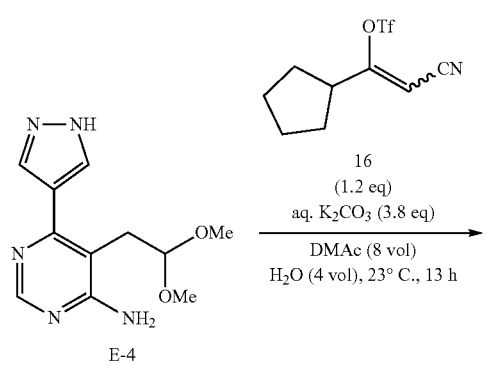

Step 5: Preparation of (R)-3-(4-(6-Amino-5-(2,2-dimethoxyethyl)pyrimidin-4-yl)-1H-pyrazol-1-yl)-3-cyclopentylpropanenitrile (E-6)

a) Hydrogenation without Additive at 10 Bar

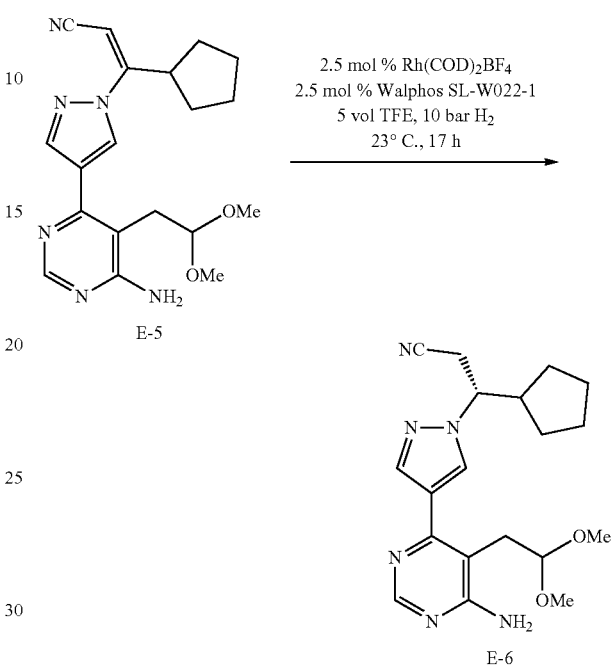

To a glass vial for a 7-vial reactor was added Rh catalyst, (5.52 mg, 0.025 equiv) Walphos ligand (9.42 mg, 0.025 equiv), and alkene E-5 (200 mg, 0.516 mmol). The solids were dissolved in trifluoroethanol (TFE, 1.0 mL, 5 volumes) and the vial placed in the reactor. The reactor was sealed, connected to a hydrogen tank, and the system purged 3× with H$_2$ and then pressurized to 10 bar. The reaction was stirred with magnetic stirring at RT for 17 h. After 17 hours, the stirring was turned off and the reactor was vented. Reaction progress checked by HPLC and the reaction determined to have gone to 95% completion. The TFE was then evaporated from the vial under a stream of nitrogen and the crude product analyzed by Chiral HPLC (IA column, 1 mL/min flow, 50:25:25 hexane:MeOH:EtOH with 0.1% diethylamine) showing a product selectivity of 99.4:0.6 er.

$^1$H NMR (400 MHz, Chloroform-d): δ 8.45 (s, 1H), 8.07 (s, 1H), 8.01 (s, 1H), 5.56 (s, NH$_2$), 4.67 (t, J=4.8 Hz, 1H), 4.21 (ddd, J=10.1, 8.6, 4.0 Hz, 1H), 3.44 (s, 6H), 3.08 (dd, J=17.0, 8.6 Hz, 1H), 3.01 (d, J=4.8 Hz, 2H), 2.92 (dd, J=17.0, 4.0 Hz, 1H), 2.55 (m, 1H), 1.95 (m, 1H), 1.79-1.51 (overlap, 5H), 1.36-1.15 (overlap, 2H).

Such methods can be Alternative reaction solvents were tested, and the results shown in Table 1 below:

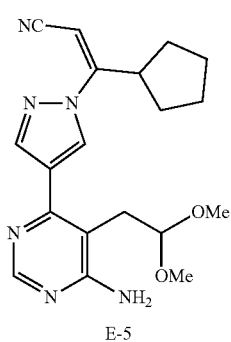

To a stirred solution of compound E-4 (0.64 g, 2.64 mmol) and enol triflate 16 (0.9 g, 3.16 mmol, 1.2 eq, 92% pure) in DMAc (5 ml) was added 2.5 ml of aq. K$_2$CO$_3$ (1.39 g, 50.3 mmol, 3.8 eq, dissolved in DI water) at 0° C. The resulting mixture was brought to room temperature and stirred for 13 h and slowly most of the product precipitated out from the solution. Then 10 ml of DI water was added to resulting brown colored reaction mixture dropwise over 5 min. Then filtered off the solids and washed with DMAc: H$_2$O (1:1) to give the product E-5 as a pale brown solid (0.44 g, 88% yield, 96% pure).

TABLE 1

| Solvent | % AUC | er R:S |
|---|---|---|
| MeOH (methanol) | 43.8% | 95.8:4.2 |
| EtOH (ethanol) | 34.4% | 90.6:9.4 |
| THF (tetrahydrofuran) | 33.6% | 83.4:16.6 |

TABLE 1-continued

| Solvent | % AUC | er R:S |
|---|---|---|
| TFT (trifluorotoluene) | 34.1% | 92.6:7.4 |
| AcOH (acetic acid) | 89.2% | 99.5:0.5 |
| HFIP (hexafluoro-isopropanol) | 93.3% | 99.3:0.7 |

Alternative catalyst and ligand amounts were tested in TFE, and the results shown in Table 2 below:

TABLE 2

| Solvent | Mol % Catalyst | % AUC | er R:S |
|---|---|---|---|
| TFE | 2.5 | 95.2% | 99.4:0.6 |
| TFE | 1.0 | 97.2% | 99.4:0.6 |
| TFE | 0.5 | 81.5% | 99.4:0.6 |
| TFE | 0.1 | 3.3% | — |

In subsequent experiments, it was found that 0.25 mol % catalyst resulted in conversion of greater than 95% at an enantiomeric ratio of greater than 99:1.

Alternative reaction conditions were tested at 50 bar Hz, and the results shown in Table 3 below:

TABLE 3

| Solvent | Mol % Catalyst | Additive | % AUC | er R:S |
|---|---|---|---|---|
| DCM | 5.0 | None | 94.2% | 99.3:0.7 |
| DCM | 2.5 | None | 80% | 98.6:1.4 |
| DCM | 2.5 | 1.0 eq HBF$_4$ | 88% | 99.4:0.6 |
| DCM | 2.5 | 0.5 eq HBF$_4$ | 91.4% | 99.4:0.6 |
| TFE | 2.5 | 0.5 eq HBF$_4$ | 85.5% | 99.5:0.5 |
| TFE | 2.5 | none | 95.8% | 99.4:0.6 |

Alternative Route to Alkenes E-6 or E-6':

In certain embodiments, alkene E-5 or deuterated alkene E-5' can be isomerized to alkene E-7 or deuterated alkene E-7', which can then be hydrogenated asymmetrically to provide enantiomerically enriched E-6 or E-6'.

a) Isomerization of E-5'

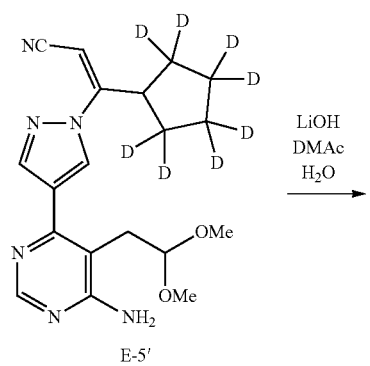

LiOH
DMAc
H$_2$O

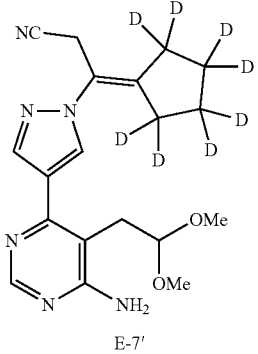

Alkene E-5' (20 g, 53.1 mmol) was dissolved in 100 mL of DMAc. A solution of lithium hydroxide (5000 mg, 80 mL) was added, and the resulting suspension was stirred at room temperature overnight. The reaction mixture was then filtered and the solid cake was washed with water and dried under vacuum to result in E-7' (19.0 g, 95.2% yield, 100% purity). $^1$H-NMR (400 MHz, DMSO-d$_6$): δ 8.29 (d, J=0.7 Hz, 1H), 8.25 (s, 1H), 8.00 (d, J=0.7 Hz, 1H), 6.64 (s, 2H), 4.63 (t, J=5.5 Hz, 1H), 3.89 (s, 2H), 3.26 (s, 6H), 2.98-2.90 (d, J=5.5 Hz, 2H).

b) Asymmetric Hydrogenation of E-7' with Chiral Ligand Walphos SL-W002-2

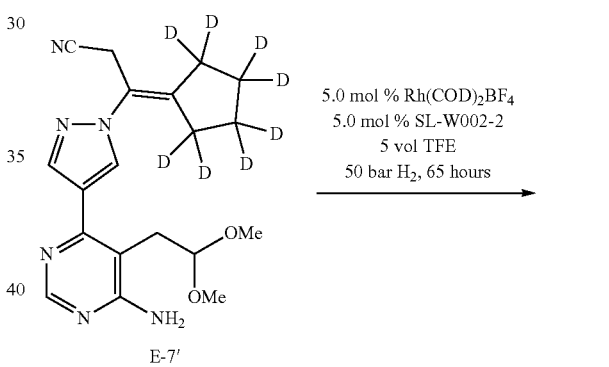

5.0 mol % Rh(COD)$_2$BF$_4$
5.0 mol % SL-W002-2
5 vol TFE
50 bar H$_2$, 65 hours

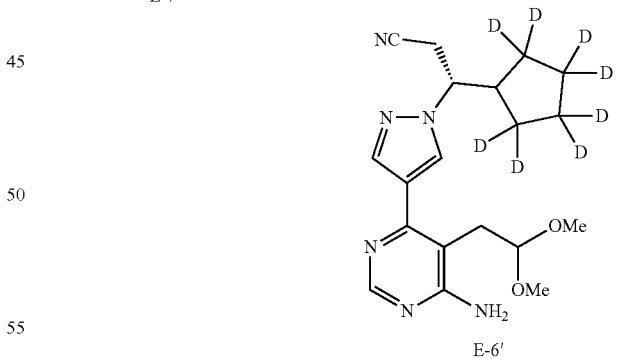

Rh catalyst (53.5 mg, 0.132 mmol, 0.05 equiv), chiral ligand Walphos SL-W002-2 (CAS #1854067-25-6) (87.4 mg, 0.133 mmol, 0.05 equiv), and alkene E-7' substrate (1.0 g, 2.66 mmol, 1.0 equiv) in 5 mL trifluoroethanol was stirred in a pressure reactor under 50 bar of hydrogen at room temperature. After 65 hours, product E-6' was formed in 21% yield as measured by HPLC. Chiral HPLC analysis (Chiralpak IE-3 column, elution with 50% hexane with 0.1% diethylamine and 50% 1:1 ethanol/methanol with 0.1% diethylamine) showed a chiral selectivity of about 83:17 er.

c) Asymmetric Hydrogenation of E-7' with Chiral Ligand SL-J002-1

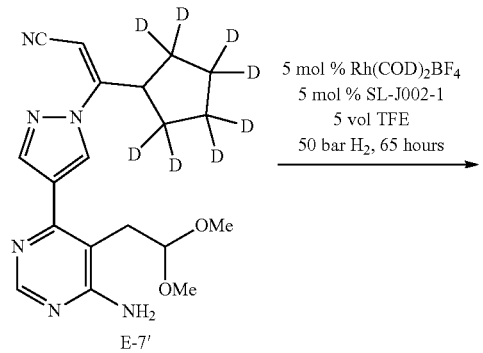

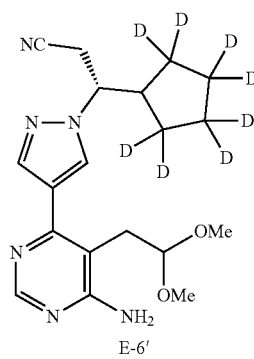

Rh catalyst (53.3 mg, 0.131 mmol, 0.05 equiv), chiral ligand Josiphos SL-J002-1 (CAS #155830-69-6) (34.4 mg, 0.063 mmol, 0.024 equiv), and alkene E-7' substrate (1.0 g, 2.66 mmol, 1.0 equiv) in 5 mL trifluoroethanol in a pressure reactor under 50 bar of hydrogen at room temperature. After 65 hours, product E-6' was formed in 79% yield as measured by HPLC. Chiral HPLC analysis (Chiralpak IE-3 column, elution with 50% hexane with 0.1% diethylamine and 50% 1:1 ethanol/methanol with 0.1% diethylamine) showed a chiral selectivity of about 89:11 er.

Salt Formation of E-6:

E-6 is an oil. For ease of purification and handling, E-6 may also be isolated as a solid acid salt. E-6 acid salts may be substituted for E-6 free base in subsequent reactions.

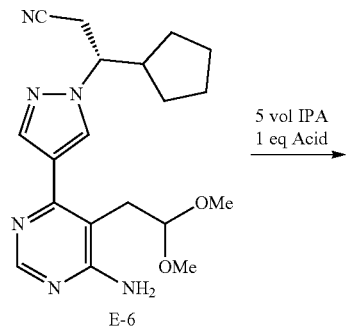

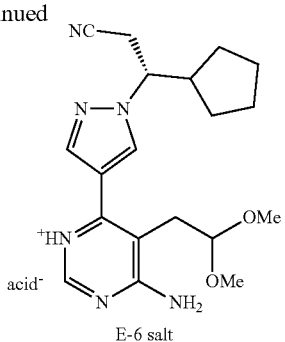

Acids:

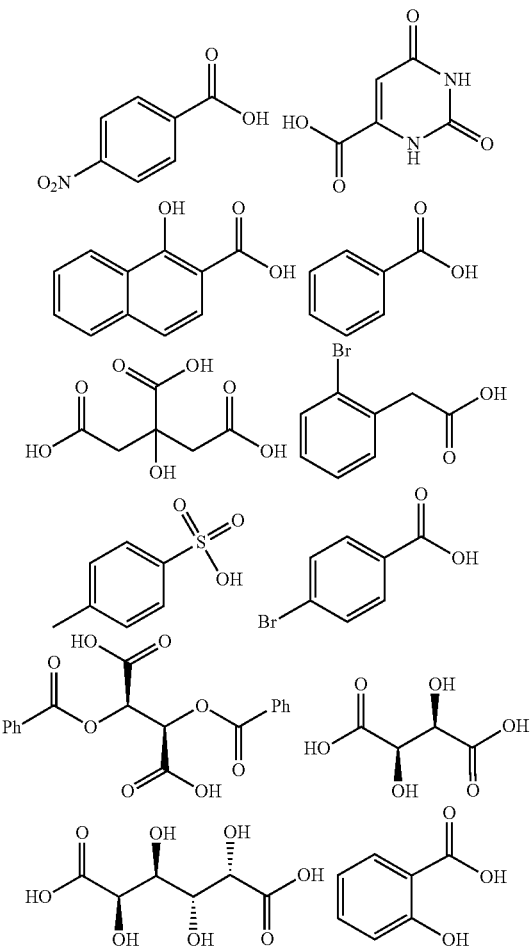

For 4-nitrobenzoic, orotic, 1-hydroxy-2-naphthoic, benzoic, citric, 2-bromophenyl acetic, and toluenesulfonic acids:

To an HPLC vial was added 50 mg (0.126 mmol) E-6. The solid was dissolved in 5 vol (0.25 mL) isopropanol. To the solution of E-6 was added 1 equivalent (0.126 mmol) acid and 5 vol (0.25 mL) of 4:1 IPA/water. The mixture stirred at room temperature for 18 hours. After 18 hours, all visible suspensions were transferred to filter centrifuge tubes and spun for 1 min at 14,000 RPM. Both the solid and mother liquors were sampled for HPLC analysis, and the solid sampled for NMR analysis and microscope images.

For 4-bromobenzoic, (+)-tartaric, mucic, and salicylic acids:

To an HPLC vial was added 50 mg (0.126 mmol) E-6. The solid was dissolved in 5 vol (0.25 mL) isopropanol. In a separate vial was added 1 equivalent (0.126 mmol) acid. To the acid was added 5 vol (0.25 mL) of 4:1 IPA/water. If the solid acid dissolved, then the acid solution was added to the E-6 solution and the mixture stirred at room temperature. If the solid acid did not dissolve, then the E-6 solution was added to the acid suspension, the mixture heated to solubility, and then the reaction cooled to RT and stirred. Vials were left to stir for 24 hours at room temperature.

After 24 hours, all visible suspensions were sampled for microscope images and then slurries were transferred to filter centrifuge tubes and spun for 1 min at 14,000 RPM. Both the solid and mother liquors were sampled for HPLC analysis, and the solid sampled for NMR analysis.

Based on NMR and HPLC analysis, E-6 formed crystalline solids with the following acids: orotic acid, 4-nitrobenzoic acid, 1-hydroxy-2-naphthoic acid, salicylic acid, and 4-bromobenzoic acid.

Salt Formation of E-6':

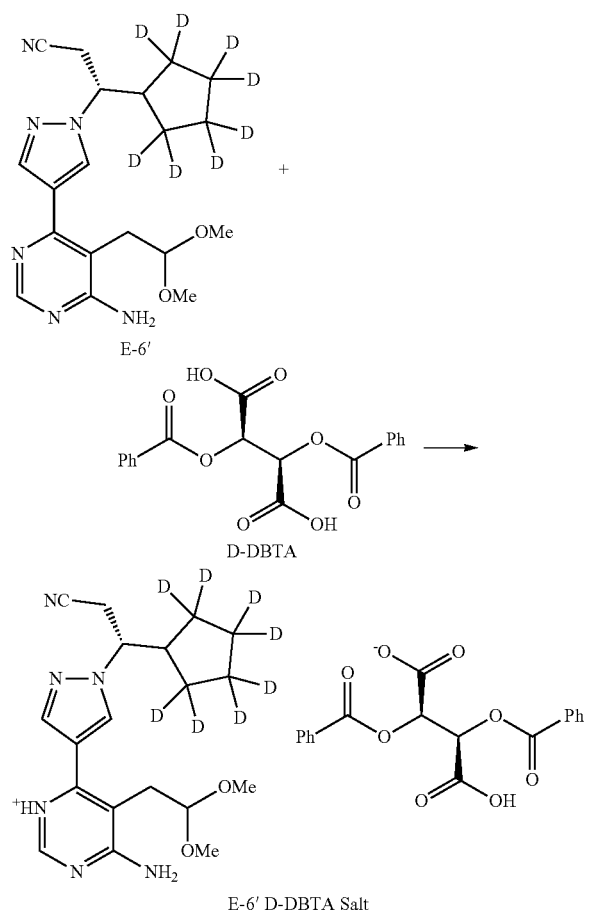

Salts of compound E-6' may be formed with any of the acids listed above for salt formation of E-6. In one embodiment, the D-dibenzoyl tartaric acid salt of E-6' is formed with excellent recovery and an improvement in the enantiomeric ratio (er). A solution of E-6' (15 mL, 167 mg/mL in trifluoroethanol, directly from reduction of E-5', 2.50 g Net) was stirred at 25° C. under nitrogen. D-dibenzoyl tartaric acid (2.50 g, 1.05 eq) was dissolved in acetonitrile (15 mL, 6 vol), and 20% of the D-dibenzoyl tartaric acid solution (3 mL) was charged to the E-6' solution. The reaction mixture was seeded with E-6' D-DTBA salt (5-6 mg, 0.002 weight equiv). The suspension was held for 20 minutes while agitating. The remaining D-dibenzoyl tartaric acid solution was charged to the E-6' solution over 1 hour. The precipitate was filtered, washed with acetonitrile (10 mL, 4 vol), and dried to provide an off-white powder (4.739 g, 98.6% w/w assay, 99.69:0.31 er, 96.1% corrected yield).

$^1$H-NMR (400 MHz, DMSO-d$_6$): δ 8.30 (d, J=8.6 Hz, 2H), 8.10-7.98 (m, 4H), 7.94 (s, 1H), 7.79-7.67 (m, 2H), 7.59 (t, J=7.7 Hz, 4H), 6.88 (br s, 2H), 5.86 (s, 2H), 4.61 (t, J=5.5 Hz, 1H), 4.48 (td, J=9.5, 4.3 Hz, 1H), 3.25 (s, 6H), 3.23-3.08 (m, 2H), 2.95 (d, J=5.5 Hz, 2H), 2.33 (d, J=9.8 Hz, 1H).

Step 6: Preparation of Ruxolitinib (Free Base)

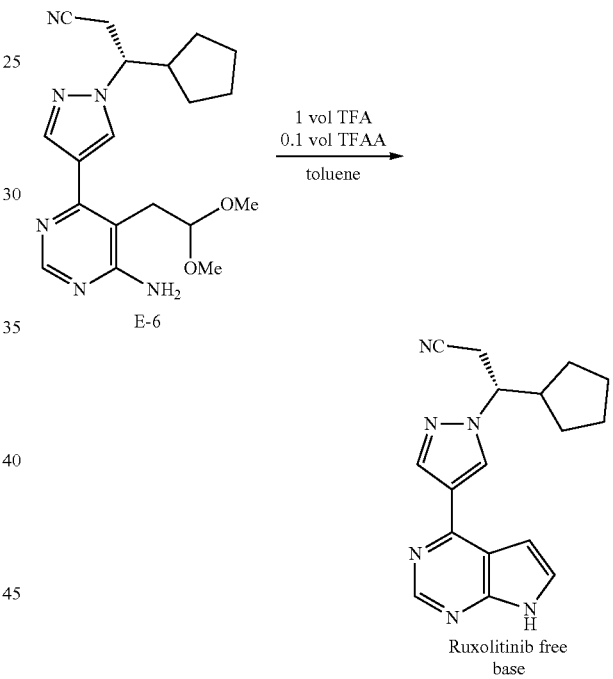

To a solution of the amino acetal E-6 (230 mg, 0.621 mmol) in toluene (2.3 mL, 10 volumes) was added trifluoroacetic acid (0.23 mL, 1 volume) and trifluoroacetic anhydride (0.023 mL, 0.1 volume). The plate was set to 100° C., and reaction allowed to stir. Reaction was monitored by HPLC. After 30 minutes, a sample was taken which showed >90% conversion to product. The reaction was allowed to stir for an additional 30 min before the heat turned off. Once the reaction had reached 30° C., triethyl amine (0.46 mL, 2 volumes) was added to neutralize the reaction. The mixture was then diluted with EtOAc and washed 2× with water. The organic phase was concentrated and the crude product was purified by flash chromatography (elution with 20-100% EtOAc in heptane) to yield the product as a white foam (61% yield). $^1$H NMR (400 MHz, DMSO-d$_6$) δ 12.10 (s, NH), 8.79 (s, 1H), 8.68 (s, 1H), 8.37 (s, 1H), 7.59 (dd, J=3.6, 2.4 Hz, 1H), 6.98 (dd, J=3.6, 1.7 Hz, 1H), 4.54 (ddd, J=9.7, 9.7, 4.2 Hz, 1H), 3.27 (dd, J=17.2, 9.6 Hz, 1H), 3.18 (dd, J=17.1, 4.2 Hz, 1H), 2.42 (m, 1H), 1.81 (m, 1H), 1.67-1.13 (overlap, 7H).

Step 6 (Alternative): Preparation of Ruxolitinib (HCl Salt)

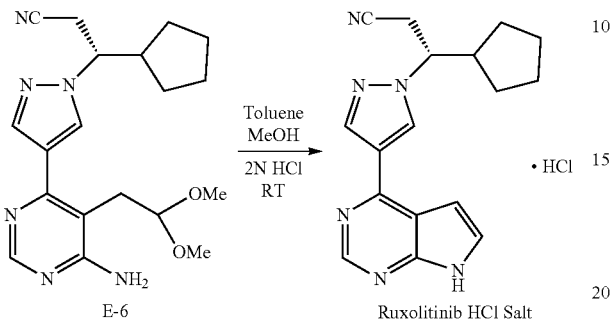

To a 50-mL RBF containing brown foamy solid E-6 (612 mg, 1.65 mmol) was added 6.0 mL toluene (9.8 volumes). The mixture was magnetically stirred to get a yellowish solution; then was added 6.0 mL 2 N HCl (9.8 volumes, 7.27 equivalents), dropwise via a syringe at ambient temperature. The resulting bi-phasic mixture was stirred at room temperature for 2 hrs. Some oily droplets were observed. To the mixture was added more HCl (0.5 mL, 6 N HCl) and MeOH (2 mL), to help solubility. The mixture was stirred at room temperature overnight. An aliquot was sampled from the lower aqueous layer, showing a conversion=99.2%, with a very clean purity profile: the desired product (ruxolitinib HCl salt) AUC=97.9 A %.

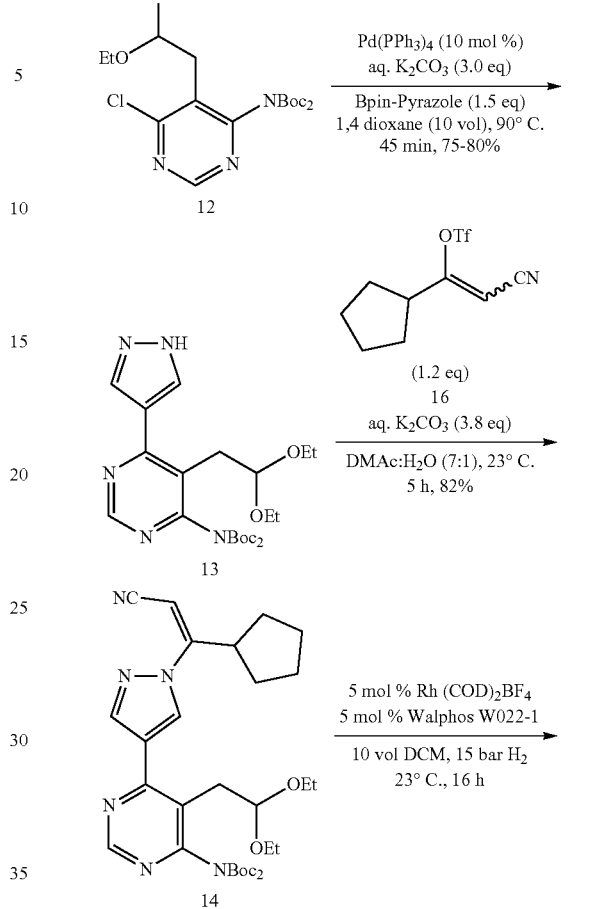

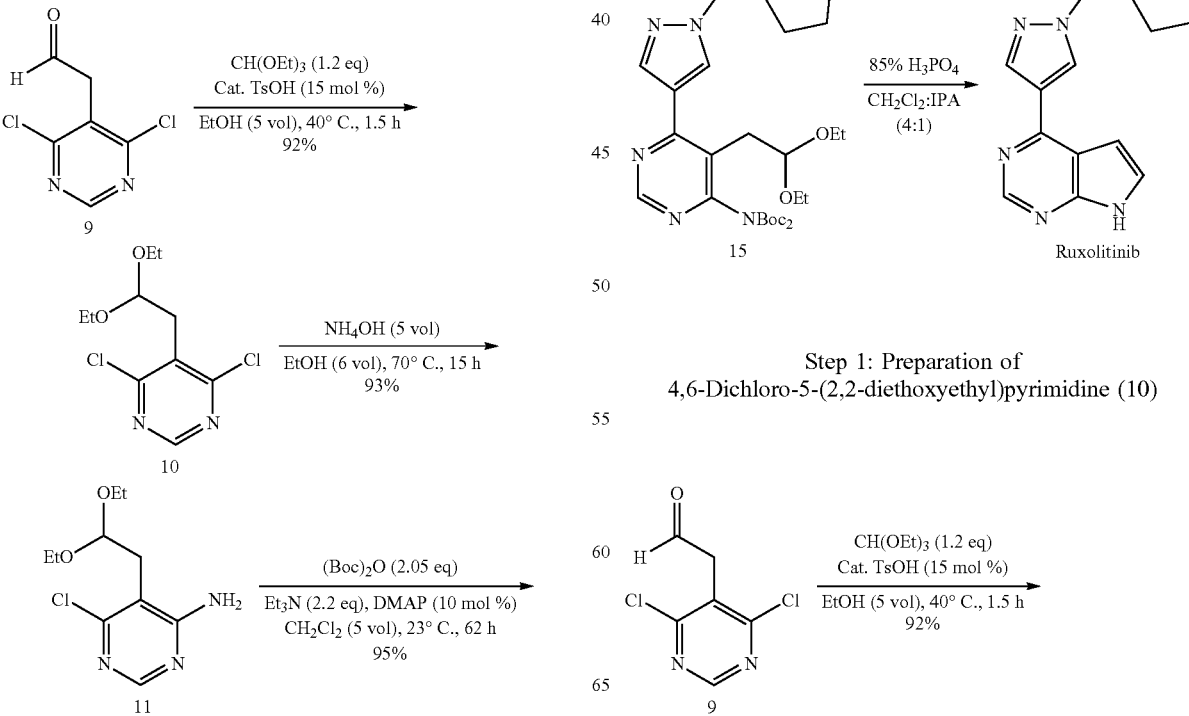

Step 1: Preparation of 4,6-Dichloro-5-(2,2-diethoxyethyl)pyrimidine (10)

-continued

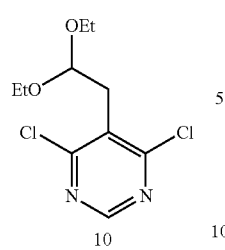

A mixture of compound 9 (B-1 in scheme 1 above) (1.5 g, 7.51 mmol), triethyl orthoformate (1.34 g, 9.02 mol, 1.2 eq), and TsOH (0.194 g, 1.13 mmol, 0.15 eq) in EtOH (15 ml) was stirred at 40° C. for 1.5 h. The reaction mixture was cooled to room temperature, aqueous Na$_2$CO$_3$ was added to adjust pH to 8. The solvent was removed under reduced pressure and the residue extracted with EtOAc (2×50 ml). The combined organic extract was washed with water (20 ml), brine (15 ml) and dried over anhydrous Na$_2$SO$_4$, filtered and concentrated under reduced pressure to give 10 (2.0 g, 92% yield) as colorless oil.

Step 2: Preparation of 6-Chloro-5-(2,2-diethoxyethyl)pyrimidin-4-amine (11)

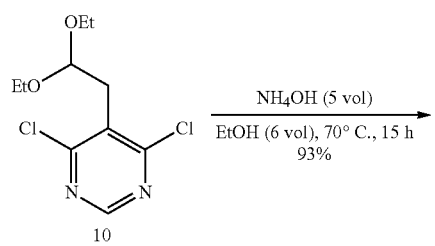

A mixture of compound 10 (2.0 g, 7.51 mmol) and NH$_4$OH (10 ml) in EtOH (12 ml) was stirred at 70° C. for 20 h. The reaction mixture was then cooled to room temperature and solvent was removed under reduced pressure. The residue was extracted with EtOAc (2×50 ml). The combined organic extract was washed with water (20 ml), brine (15 ml) and dried over anhydrous Na$_2$SO$_4$, filtered and concentrated under reduced pressure to give 11 (1.72 g, 93%) as yellow colored oil.

Step 3: Preparation of tert-Butyl (tert-butoxycarbonyl)(6-chloro-5-(2,2-diethoxyethyl)pyrimidin-4-yl)carbamate (12)

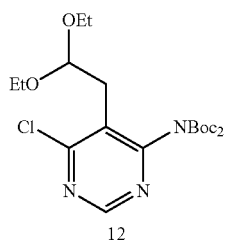

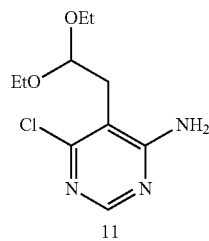

To a stirred solution of compound 11 (1.6 g, 6.51 mmol) in CH$_2$Cl$_2$ (18 ml) was added Et$_3$N (2 ml, 14.3 mmol, 2.2 eq), (Boc)$_2$O (2.91 g, 13.3 mmol, 2.05 eq), and DMAP (80 mg, 0.651 mmol, 0.1 eq) sequentially at 0° C. The resulting mixture was brought to room temperature and stirred for 62 h. The reaction mixture was then treated with water and extracted with ethyl acetate (2×50 mL). The combined organic extract was washed with water (15 ml) brine (15 mL), dried over Na$_2$SO$_4$, filtered and concentrated under reduced pressure to give 12 as a yellow solid (2.78 g, 95% yield).

Step 4: Preparation of tert-Butyl (tert-butoxycarbonyl)(5-(2,2-diethoxyethyl)-6-(1H-pyrazol-4-yl)pyrimidin-4-yl)carbamate (13)

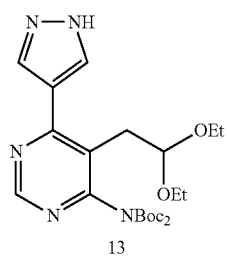

To a mixture of 12 (1 g, 2.24 mmol) and BPin-Pyrazole (0.57 g, 2.92 mmol, 1.3 eq) in dioxane (10 ml) was added 3 ml of aq. K$_2$CO$_3$ (0.937 g, 6.73 mmol, 3.0 eq) at room temperature. The solution was degassed by passing a stream of nitrogen through the solution for 15 minutes before being treated with Pd(PPh₃)₄ (52 mg, 0.044 mmol, 0.02 eq) and the resulting reaction mixture was heated at 90° C. for 1 hour. The reaction mixture was brought to room temperature then diluted with ethyl acetate (30 ml) and water (15 ml). The two layers were separated, and the aqueous layer was further extracted with ethyl acetate (20 ml). The combined organic extract was washed with water (2×10 ml), brine (15 ml), dried over anhydrous Na₂SO₄, filtered and concentrated under reduced pressure to give 13 as a gummy oil (0.85 g, 80% yield).

Step 5: Preparation of tert-Butyl (Z)-(tert-butoxycarbonyl)(6-(1-(2-cyano-1-cyclopentylvinyl)-1H-pyrazol-4-yl)-5-(2,2-diethoxyethyl)pyrimidin-4-yl) carbamate (14)

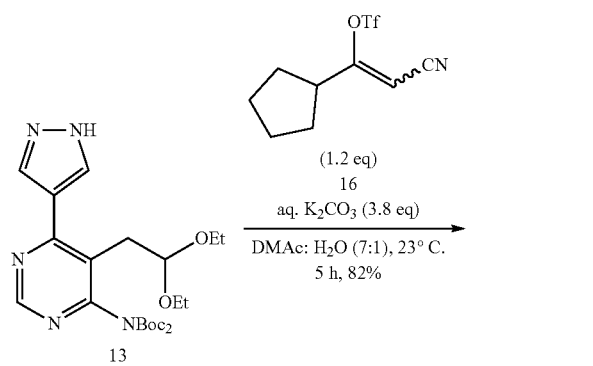

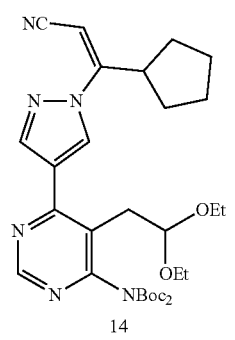

To a stirred solution of compound 13 (0.964 g, 2.02 mmol) and 16 (0.652 g, 2.42 mmol, 1.2 eq) in DMAc (18 ml) was added 3.5 ml of aq. K₂CO₃ (1.06 g, 7.67 mmol, 3.8 eq) at 0° C. The resulting mixture was brought to room temperature and stirred for 5 h. The reaction mixture was then treated with water and extracted with MTBE (2×50 mL). The combined organic extract was washed with water (20 ml) and brine (20 mL), dried over Na₂SO₄, filtered and concentrated under reduced pressure to give 14 as a yellow oil (0.98 g, 82% yield).

Step 6: Preparation of tert-Butyl (R)-(tert-butoxycarbonyl)(6-(1-(2-cyano-1-cyclopentylethyl)-1H-pyrazol-4-yl)-5-(2,2-diethoxyethyl)pyrimidin-4-yl) carbamate (15)

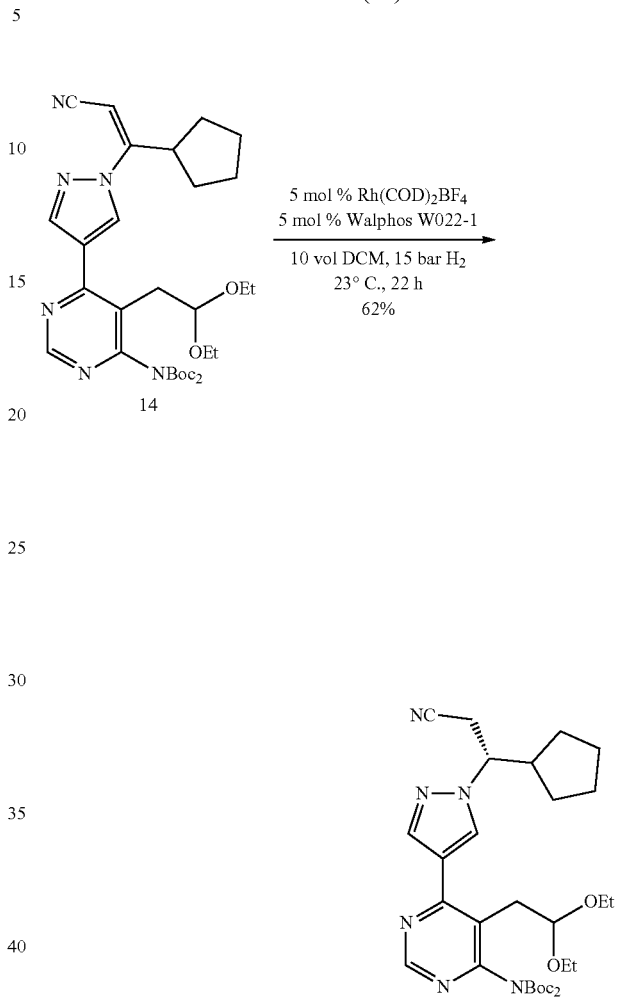

To a stirred glass vial inside a pressure reactor was added 14 (80 mg, 0.134 mmol), Rh(COD)₂BF₄ (2.75 mg, 0.0068 mmol, 5 mol %), and Walphos SL-W022-1 (4.73 mg, 0.0068 mmol, 5 mol %) and dichloromethane (0.80 mL, 10 volumes). The pressure reactor was sealed and the system was purged 3 times then pressurized to 15 bar with hydrogen gas. The reaction was then stirred at room temperature for 22 hours. After venting the reactor the crude reaction mixture was dissolved in a small amount of dichloromethane and purified by ISCO automated chromatography (elution with 0->50% EtOAc in heptane). Fractions containing the product were pooled, concentrated, and dried under vacuum to yield 15 (50 mg, 62.3% yield). ¹H NMR (400 MHz, DMSO-d₆) δ 8.97 (s, 1H), 8.58 (s, 1H), 8.18 (s, 1H), 4.64 (t, J=5.6 Hz, 1H), 4.53 (ddd, J=9.4, 9.4, 4.5 Hz, 1H), 3.56 (m, 2H), 3.41-3.26 (overlap, 2H), 3.21 (dd, J=17.2, 9.2 Hz, 1H), 3.15 (dd, J=17.1, 4.5 Hz, 1H), 2.97 (dd, J=5.8, 1.7 Hz, 2H), 2.38 (m, 1H), 1.79 (m, 1H), 1.67-1.14 (overlap, 7H), 1.41 (s, 18H), 1.01 (td, J=7.0, 4.0 Hz, 6H).

Additional catalyst systems were also tested for the hydrogenation step, with the results shown below:

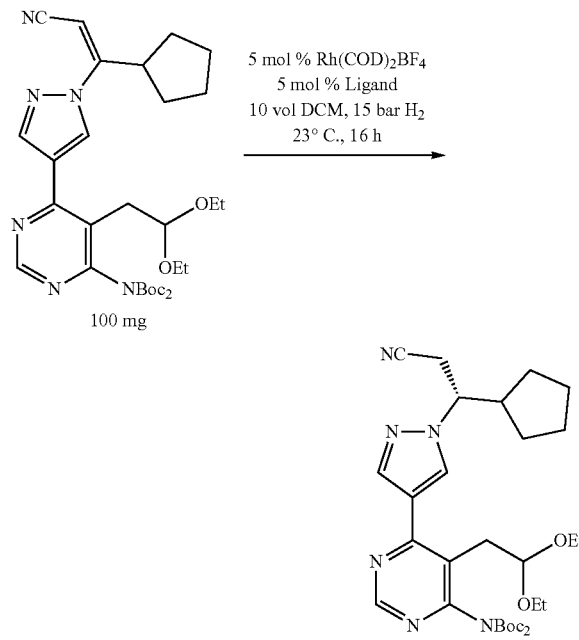

| Ligand Name | % Conversion | Enantiomeric Excess |
|---|---|---|
| Walphos W022-1 | 100 | 97:3 er |
| Walphos W003-1 | 99 | 94.5:5.5 er |
| Walphos W001-1 | 0 | |
| W002-1 | 3 | |
| W005-1 | 3 | |
| W006-1 | 1 | |
| W008-1 | 10 | |
| W009-1 | 3 | |
| Josiphos J001-1 | 0 | |
| J002-1 | 6 | |
| J003-1 | 3 | |
| J006-1 | 1 | |
| J007-1 | 3 | |
| J009-1 | 4 | |
| J011-1 | 0 | |

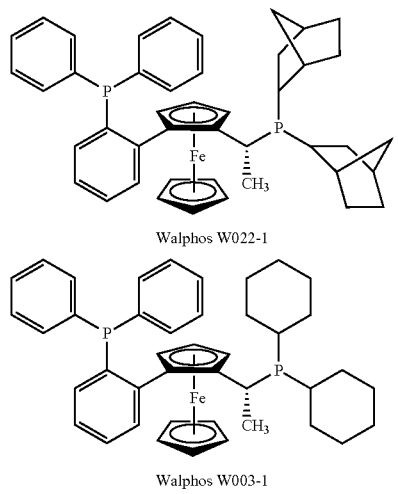

All ligands are available from Solvias AG (Kaiseraugst, Switzerland) and/or Strem Chemicals (Newburyport, MA, USA).

Step 7: Preparation of (R)-3-(4-(7H-Pyrrolo[2,3-d]pyrimidin-4-yl)-1H-pyrazol-1-yl)-3-cyclopentylpropanenitrile (Ruxolitinib)

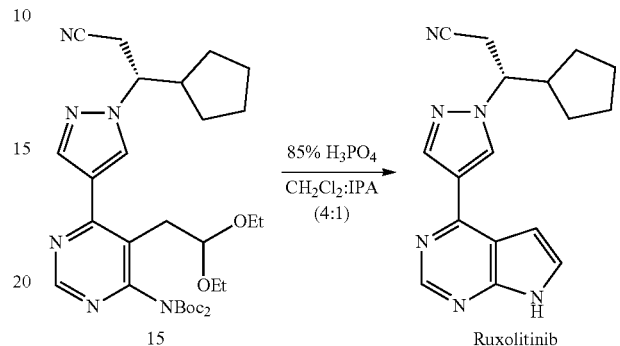

To a stirred round bottom flask containing 15 (20 mg, 0.033 mmol), dichloromethane (0.40 mL, 20 volumes), and isopropanol (0.10 mL, 5 volumes) was added 85% phosphoric acid (20 μL). The reaction was stirred at room temperature for 1 hour before additional 85% phosphoric acid (30 μL) was added. After 1 hour stirring at room temperature, additional 85% phosphoric acid (50 μL) was added. The reaction was allowed to stir overnight at room temperature. After stirring overnight, reaction progress was monitored by LCMS. The reaction was determined to have proceeded to 77% conversion by UV. The crude cyclization mixture was quenched with water with saturated aqueous potassium carbonate. The quenched reaction was then extracted with DCM, dried over sodium sulfate, and the solvent was evaporated. The crude product was evaluated with chiral HPLC. Chiral HPLC (AD-H column, 1 mL/min flow, 50:50 MeOH:EtOH with 0.1% diethylamine) showed an enantiometric ratio of 97:3, ruxolitinib to ruxolitinib-X (undesired enantiomer).

Scheme 6a: Preparation of Ruxolitinib Phosphate Through the Methyl Acetal

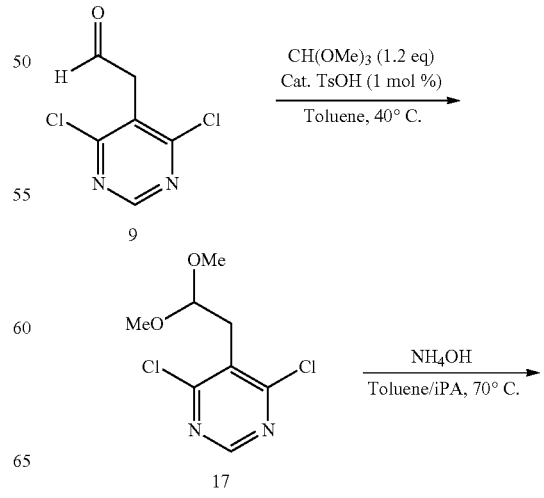

-continued
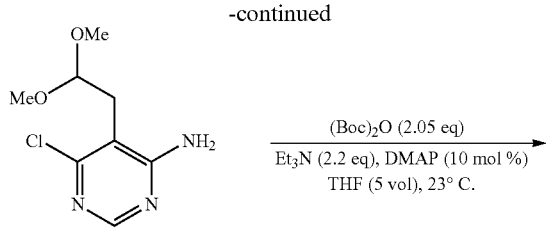
18
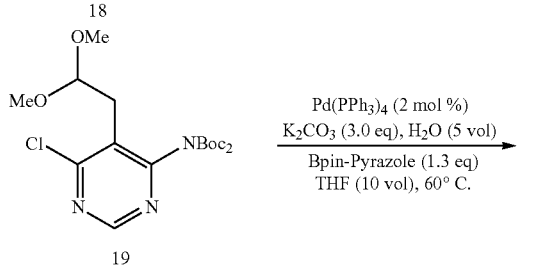
19
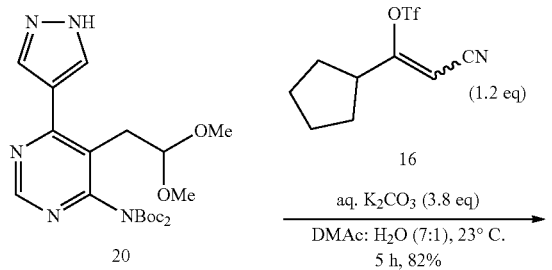
20
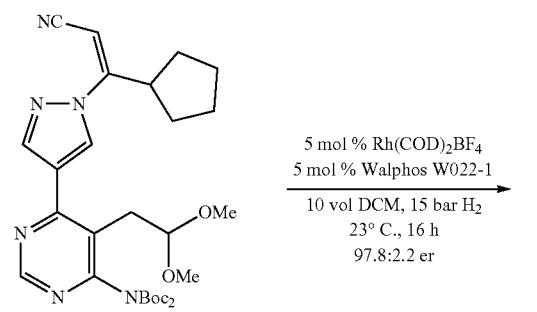
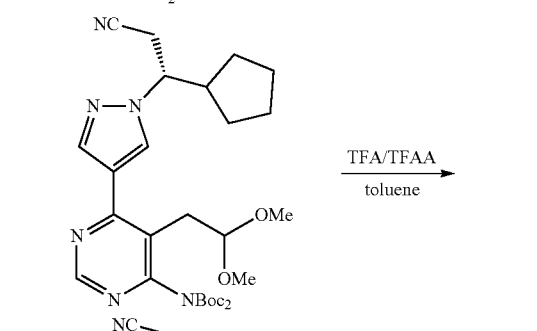
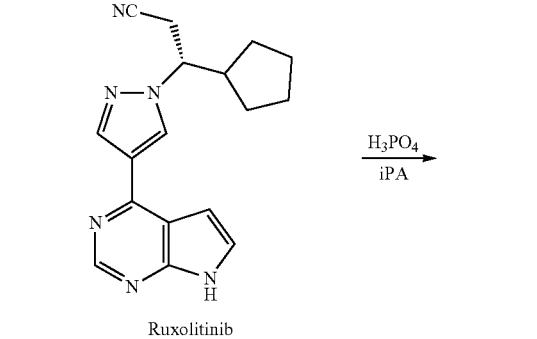
Ruxolitinib
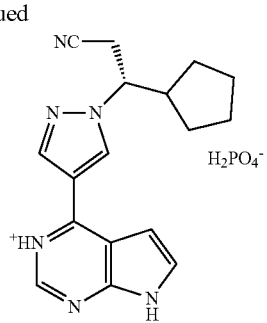
Ruxolitinib Phosphate
Scheme 6b: Preparation of Ruxolitinib Phosphate Through the Methyl Acetal
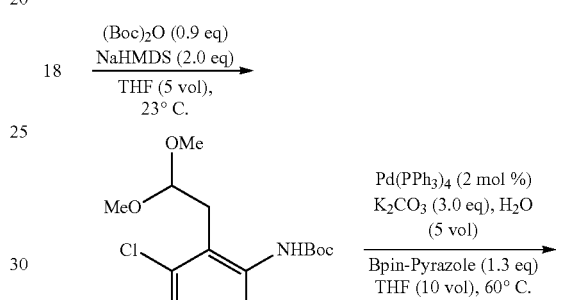
21
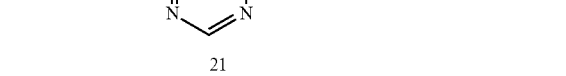
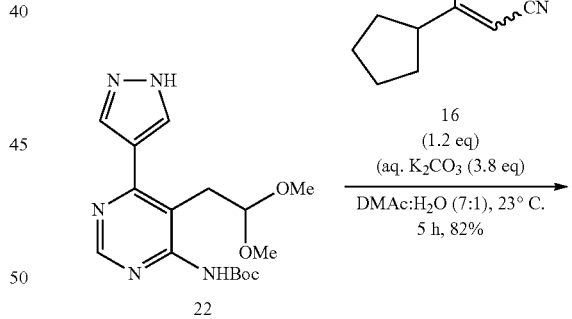
22
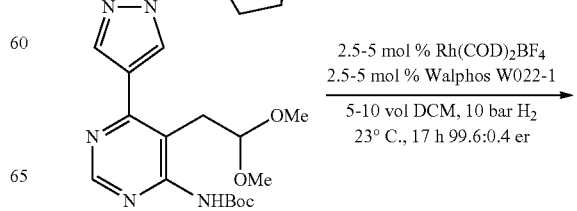

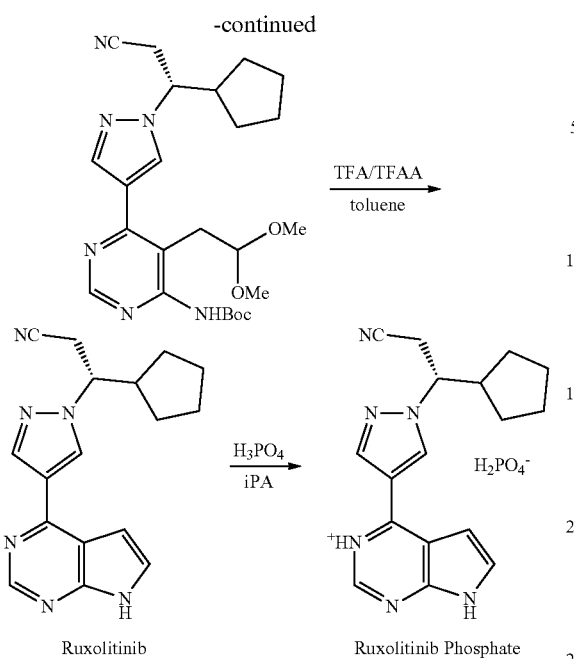

Ruxolitinib

Ruxolitinib Phosphate

Step 1A: Preparation of 4,6-Dichloro-5-(2,2-dimethoxyethyl)pyrimidine (17)

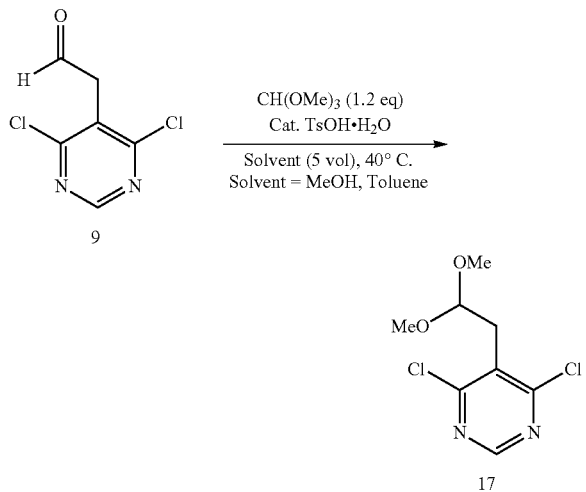

a) MeOH, TsOH (10 mol %):

Such methods can be A mixture of compound 9 (10 g, 52.4 mmol), trimethyl orthoformate (6.67 g, 62.8 mmol, 1.2 eq), and TsOH·H$_2$O (0.902 g, 5.24 mmol, 0.10 eq) in MeOH (50 ml) was stirred at 40° C. for 1.5 h. The reaction mixture was cooled to room temperature, aqueous Na$_2$CO$_3$ (20 mL) was added to adjust pH to 8 and extracted with EtOAc (2×50 ml). The combined organic extract was washed with water (20 ml), brine (15 ml) and dried over anhydrous Na$_2$SO$_4$, filtered and concentrated under reduced pressure to give 17 (11.9 g, 96% yield) as brown solid.

b) Toluene, TsOH (1 mol %):

To a suspension of compound 9 (635 g, 88% assay, 2.93 mol) in toluene (2988 g) was charged trimethyl orthoformate (371 g, 3.50 mol, 1.2 eq). The batch was cooled to 20° C. and solid TsOH·H$_2$O (5.76 g, 0.03 mol, 0.01 eq) was charged. Batch temperature was maintained by lowering the jacket temperature to 16° C. for 10 minutes during a minor exotherm, before adjustment to 20° C. After stirring the suspension for 2 hours at 20° C., the jacket temperature was raised to 40° C. for 11.5 hours before returning the jacket to 20° C. HPLC indicated consumption of starting material. Assay of the brown solution provided a concentration of approximately 136 mg/mL 17 (total volume approximately 4.40 L, 597-631 g product, 86% yield).

The batch was filtered through a coarse glass frit before use in the next step.

Step 2A: Preparation of 6-Chloro-5-(2,2-dimethoxyethyl)pyrimidin-4-amine (18)

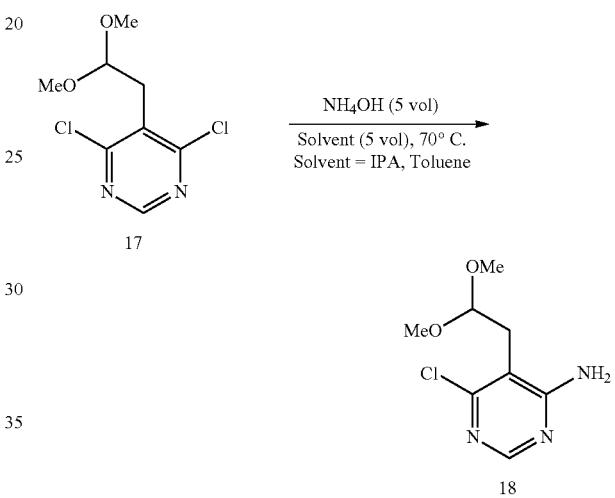

a) Procedure 1: iPA:

A mixture of compound 17 (6.0 g, 25.3 mmol) and NH$_4$OH (30 ml) in IPA (30 ml) was stirred at 70° C. for 8 h. The reaction mixture was then cooled to room temperature and solvent was removed under reduced pressure. The residue was extracted with EtOAc (2×60 ml). The combined organic extract was washed with water (20 ml), brine (15 ml) and dried over anhydrous Na$_2$SO$_4$, filtered and concentrated under reduced pressure to give 18 (5.3 g, 96%) as pale brown solid.

b) Toluene/iPA:

To a toluene solution of 17 (4.40 L, approximately 136 mg/mL) in a 10 L jacketed glass reactor (Jacket temperature 20° C., stir rate 130 RPM, condenser temperature: -5° C.) was charged ammonium hydroxide solution (235 g). The mixture presented an exotherm that raised batch temperature 3° C. The mixture was stirred for 4 hours before agitation was paused to allow removal of the aqueous layer (dark brown, lower layer, 376 g). The reactor jacket was set to 40° C. Ammonium hydroxide solution (298 g) was charged and the batch was held for 2 days. Additional ammonium hydroxide (200 g) and isopropanol (4 L) were charged, and the reactor jacket was set to 70° C. Additional ammonium hydroxide solution (421 g) was periodically added over the next 24 hours, and the reaction was deemed complete after agitation at 70° C. for 6 days. The batch was cooled to 20° C. and water (1.0 L) wash charged to the batch. Agitation was stopped and the aqueous cut was removed. The batch was discharged into a drum and treated with activated charcoal (78 g). After standing for three hours, the batch was filtered into a clean reactor. A distillation apparatus was attached and the batch was distilled to volume of 2.5 L. Toluene was charged (876 g). After additional distillation (1023 g distilled) the reactor jacket was cooled to 10° C. over 4 hours. Heptane (100 g) was charged and the batch was agitated for 4 hours. The batch was filtered with suction onto three disposable polypropylene fritted funnels to obtain a tan solid. The reactor was washed with 280 g toluene. Each filter cake was washed with 100 mL toluene. Each filter cake was dried with suction to a transferrable solid before combination into a drying tray. The solids were dried under vacuum with a nitrogen stream to yield a tan solid (343.2 g, 94.6 wt %, 55% yield).

Step 3A: Preparation of tert-Butyl (tert-butoxycarbonyl)(6-chloro-5-(2,2-dimethoxyethyl)pyrimidin-4-yl)carbamate (19)

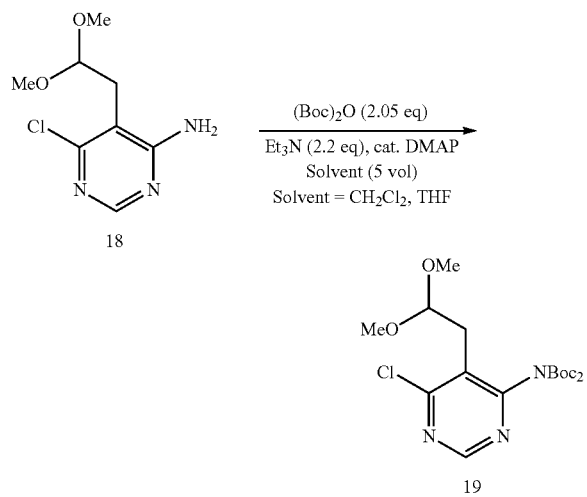

a) $CH_2Cl_2$, DMAP (10 mol %):

To a stirred solution of compound 18 (4.65 g, 21.4 mmol) in $CH_2Cl_2$ (25 ml) was added $Et_3N$ (6.55 ml, 47.3 mmol, 2.2 eq), $(Boc)_2O$ (9.56 g, 43.8 mmol, 2.05 eq), and 4-dimethylaminopyridine (DMAP) (261 mg, 2.14 mmol, 0.1 eq) sequentially at 0° C. The resulting mixture was brought to room temperature and stirred for 8 h. The reaction mixture was then treated with water and extracted with ethyl acetate (2×60 mL). The combined organic extract was washed with water (15 ml) brine (15 mL), dried over $Na_2SO_4$, filtered and concentrated under reduced pressure to give 19 as a pale yellow solid (8.1 g, 95% yield).

b) THF:

To a stirred solution of compound 18 (11.12 g, 51.1 mmol) and $(Boc)_2O$ (22.9 g, 105 mmol, 2.05 eq) was added THF (50 ml). $Et_3N$ (15 ml, 47.3 mmol, 2.1 eq) and DMAP (625 mg, 5.1 mmol, 0.1 eq) were charged. A small exotherm was noted (2° C.). The batch was warmed to 40° C. for 20 minutes, then cooled to 20° C. HPLC indicated reaction was >97% complete. N-methylpiperazine (0.56 mL, 5.1 mmol, 0.1 eq) was charged and the batch was stirred for 30 minutes. Monobasic potassium phosphate solution (1 M, 100 mL, 100 mmol, 2 eq) and THF (40 mL) was charged. After a brief stir, the aqueous cut was removed. Monobasic potassium phosphate solution (1 M, 50 mL, 50 mmol, 1 eq) and THF (20 mL) was charged. Water (20 mL) was charged as a final rinse to remove residual salts. The product solution (130 mL) was used in portions in the next step.

Step 4A: Preparation of tert-Butyl (tert-butoxycarbonyl)(5-(2,2-dimethoxyethyl)-6-(1H-pyrazol-4-yl)pyrimidin-4-yl)carbamate (20)

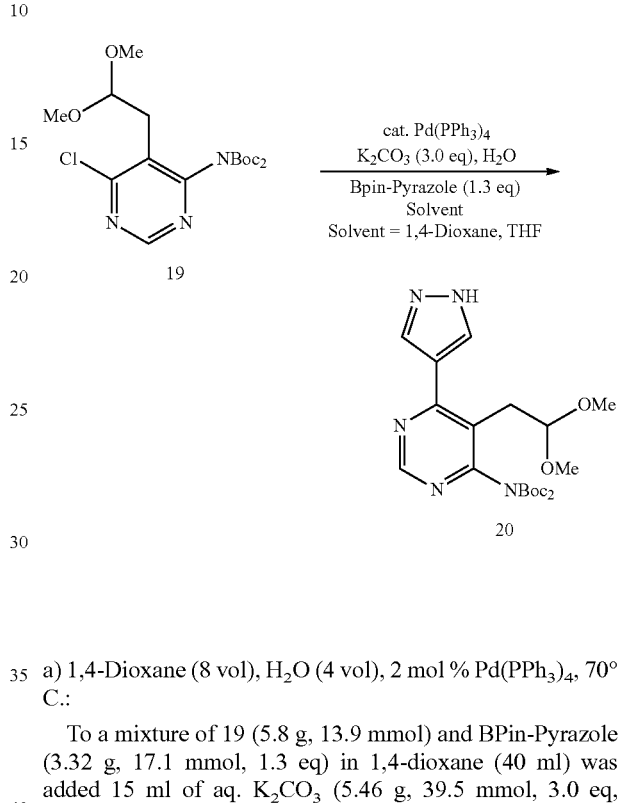

a) 1,4-Dioxane (8 vol), $H_2O$ (4 vol), 2 mol % $Pd(PPh_3)_4$, 70° C.:

To a mixture of 19 (5.8 g, 13.9 mmol) and BPin-Pyrazole (3.32 g, 17.1 mmol, 1.3 eq) in 1,4-dioxane (40 ml) was added 15 ml of aq. $K_2CO_3$ (5.46 g, 39.5 mmol, 3.0 eq, dissolved in DI water) at room temperature. The solution was degassed by passing a stream of nitrogen through the solution for 15 minutes before being treated with $Pd(PPh_3)_4$ (304 mg, 0.263 mmol, 0.02 eq) and the resulting reaction mixture was heated at 70° C. for 2 hour. The reaction mixture was brought to room temperature then filtered off the yellow colored solids and filtrate was diluted with ethyl acetate (50 ml) and water (15 ml). The two layers were separated, and the aqueous layer was further extracted with ethyl acetate (40 ml). The combined organic extract was washed with water (2×15 ml), brine (15 ml), dried over anhydrous $Na_2SO_4$, filtered and concentrated under reduced pressure to give 20 as a gummy oil (crude weight, ~6 g) which was used in the next conjugate addition reaction without any further purification.

b) THF (10 vol), $H_2O$ (4 vol), 2 mol % $Pd(PPh_3)_4$, 60° C.:

To a mixture of 19 (0.25 g, 0.598 mmol) and BPin-Pyrazole (0.151 g, 0.778 mmol, 1.3 eq) in THF (2.5 ml) was added 1 ml of aq. $K_2CO_3$ (0.248 g, 1.79 mmol, 3.0 eq, dissolved in DI water) at room temperature. The solution was degassed by passing a stream of nitrogen through the solution for 15 minutes before being treated with $Pd(PPh_3)_4$ (14 mg, 0.0119 mmol, 0.02 eq) and the resulting reaction mixture was heated at 60° C. for 12 h. After 12 h, the reaction profile was starting material (18%) and product 20 (82%).

Step 5A: Preparation of tert-Butyl (Z)-(tert-butoxycarbonyl)(6-(1-(2-cyano-1-cyclopentylvinyl)-1H-pyrazol-4-yl)-5-(2,2-dimethoxyethyl)pyrimidin-4-yl)carbamate

Step 6A: Preparation of tert-Butyl (R)-(tert-butoxycarbonyl)(6-(1-(2-cyano-1-cyclopentylethyl)-1H-pyrazol-4-yl)-5-(2,2-dimethoxyethyl)pyrimidin-4-yl)carbamate

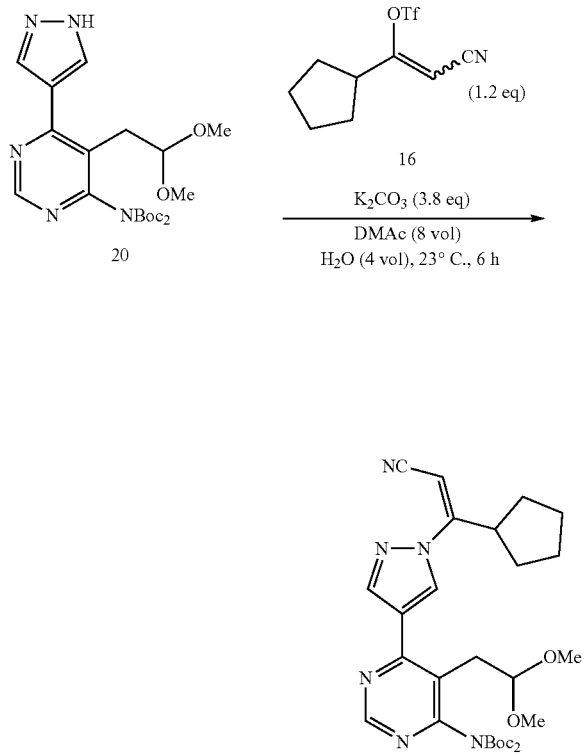

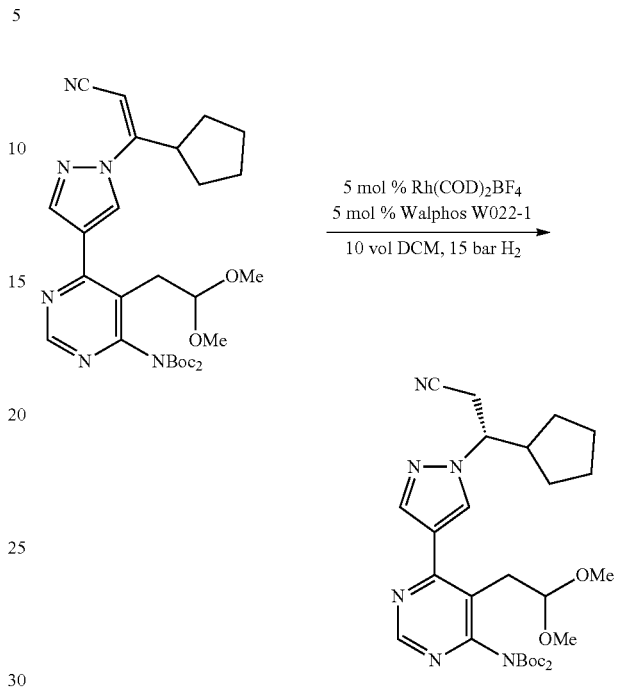

To a stirred glass vial inside a pressure reactor was added alkene (1.0 g, 1.76 mmol), Rh(COD)$_2$BF$_4$ (35.7 mg, 0.0878 mmol, 5 mol %), and Walphos SL-W022-1 (61.1 mg, 0.0879 mmol, 5 mol %) and dichloromethane (10.0 mL, 10 volumes). The pressure reactor was sealed and the system was purged 3 times then pressurized to 15 bar with hydrogen gas. The reaction was then stirred at room temperature for 16 hours. After venting the reactor the crude reaction mixture was dissolved in a small amount of dichloromethane and purified by ISCO automated chromatography (elution with 0->50% EtOAc in heptane). Fractions containing the product were pooled, concentrated, and dried under vacuum to yield the product (600 mg, 59.8% yield). $^1$H NMR (400 MHz, DMSO-d$_6$) δ 8.96 (s, 1H), 8.57 (d, J=0.7 Hz, 1H), 8.16 (s, 1H), 4.56-4.49 (overlap, 2H), 3.22 (dd, J=17.3, 9.2 Hz, 1H), 3.20 (s, 3H), 3.19 (s, 3H), 3.16 (dd, J=17.5, 4.9 Hz, 1H), 3.00 (d, J=5.6 Hz, 2H), 2.38 (m, 1H), 1.80 (m, 1H), 1.64-1.14 (overlap, 7H), 1.41 (s, 18H).

To a stirred solution of compound 20 (5.95 g, 13.2 mmol) and Enol triflate (4.28 g, 15.9 mmol, 1.2 eq, 92% pure) in DMAc (48 ml) was added 25 ml of aq. K$_2$CO$_3$ (6.95 g, 50.3 mmol, 3.8 eq, dissolved in DI water) at 0° C. The resulting mixture was brought to room temperature and stirred for 6 h. Then after 50 ml of DI water was added to resulting brown colored reaction mixture slowly over one hour using syringe pump. The product was precipitated out from the reaction mixture. Then filtered off the solids and washed with DMAc:H$_2$O (1:4) to give the product as pale brown solid (6.4 g, 90% pure, 85% yield over two steps). Product was recrystallized from IPA.

Notes:

1). Add water until you don't see product precipitation, approximately 10-12 vol. of water needed.

2). Standard compound (>99% pure) is a white crystalline solid.

3). For recrystallization, added 3 vol. of IPA, product sparingly soluble then heated 50° C. At 50° C., product was completely soluble, then allowed to room temperature.

Step 7A: Preparation of (R)-3-(4-(7H-Pyrrolo[2,3-d]pyrimidin-4-yl)-1H-pyrazol-1-yl)-3-cyclopentyl-propanenitrile (Ruxolitinib Free Base)

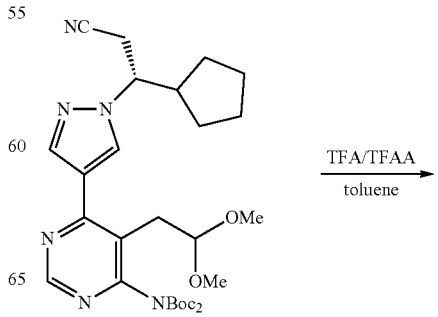

-continued

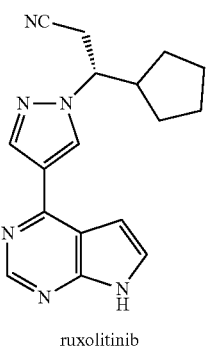
ruxolitinib

To an HPLC vial containing the amino acetal (80 mg, 0.140 mmol) was added toluene (0.80 mL, 10 volumes) to dissolve the material. To the flask was then added trifluoroacetic acid (0.08 mL, 1 volume) and the plate was set to 100° C. and reaction allowed to stir. Reaction was monitored by HPLC. After 15 minutes, a sample was taken which showed >90% conversion to product. The reaction was allowed to cool to 40° C. and then to the vial was added trifluoroacetic anhydride (0.08 mL, 1 volume). After 15 minutes, the reaction had gone to completion. Water (0.80 mL, 10 volumes) was added to quench the reaction. The mixture was neutralized with $Na_2CO_3$ and extracted with EtOAc. The crude product was dried over sodium sulfate and concentrated to yield the product as a white foam (27 mg, 62.9% yield). Chiral HPLC (AD-H column, 1 mL/min flow, 50:50 MeOH:EtOH with 0.1% diethylamine) showed an enantiometric ratio of 97.8:2.2, ruxolitinib to the undesired enantiomer.

Step 1B: Preparation of tert-Butyl (6-chloro-5-(2,2-dimethoxyethyl)pyrimidin-4-yl)carbamate (21)

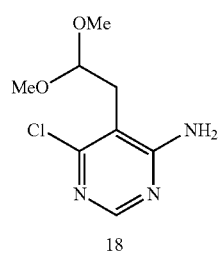

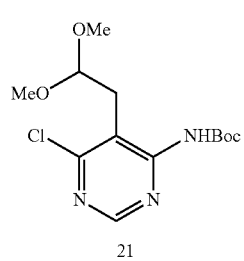

To a stirred solution of compound 18 (215 mg, 0.988 mmol) in THF (2 ml) was added 2 M NaHMDS (1 ml, 1.976 mmol, 2.0 eq, 2 M in THF) at 0° C. After 30 min stirring at 0° C., a solution of $(Boc)_2O$ (194 mg, 0.889 mmol, 0.9 eq) in THF (1.5 ml) was added at 0° C. The resulting mixture was brought to room temperature and stirred for 8 h, from LC, reaction was 90% completed. The reaction mixture was then treated with water (2 ml) and extracted with ethyl acetate (2×20 mL). The combined organic extract was washed with water (10 ml) brine (10 mL), dried over $Na_2SO_4$, filtered and concentrated under reduced pressure. The crude residue was purified by flash chromatography (0 to 30% EtOAc in Heptane) to give mono-Boc product (21) as a white solid (370 mg, 87% yield).

Step 2B: Preparation of tert-butyl (5-(2,2-dimethoxyethyl)-6-(1H-pyrazol-4-yl)pyrimidin-4-yl)carbamate (22)

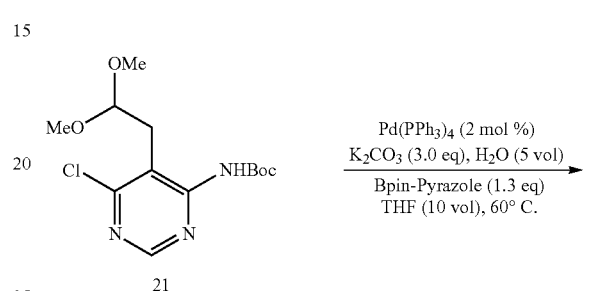

Step 3B: Preparation of tert-butyl (Z)-(6-(1-(2-cyano-1-cyclopentylvinyl)-1H-pyrazol-4-yl)-5-(2,2-dimethoxyethyl)pyrimidin-4-yl)carbamate

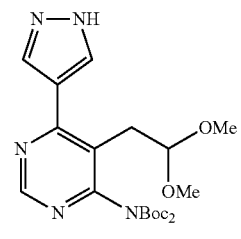

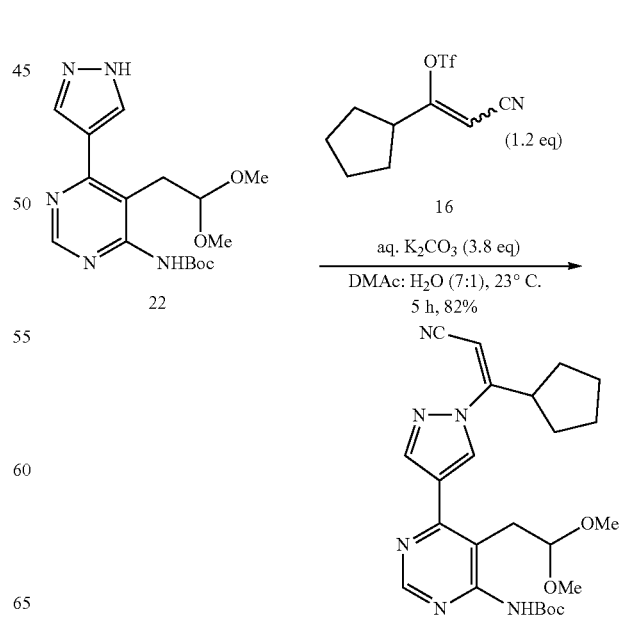

115

Step 4B: Preparation of tert-butyl (R)-(6-(1-(2-cyano-1-cyclopentylethyl)-1H-pyrazol-4-yl)-5-(2,2-dimethoxyethyl)pyrimidin-4-yl)carbamate

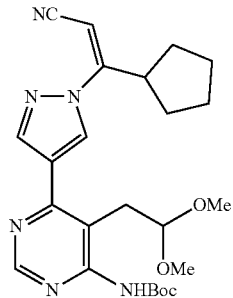

5 mol % Rh(COD)₂BF₄
5 mol % Walphos W022-1

10 vol DCM, 10 bar H₂
23° C., 17 h
99.6:0.4 er

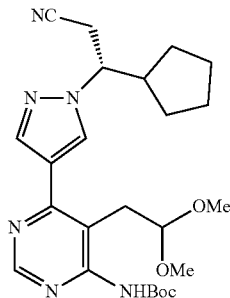

To a stirred glass vial inside a pressure reactor was added alkene (0.50 g, 1.01 mmol), Rh(COD)₂BF₄ (20.5 mg, 0.0505 mmol, 5 mol %), and Walphos SL-W022-1 (35.1 mg, 0.0505 mmol, 5 mol %) and dichloromethane (5.0 mL, 10 volumes). The pressure reactor was sealed and the system was purged 3 times then pressurized to 10 bar with hydrogen gas. The reaction was then stirred at room temperature for 17 hours. After venting the reactor the crude reaction mixture was dissolved in a small amount of dichloromethane and purified by ISCO automated chromatography (elution with 0->50% EtOAc in heptane). Fractions containing the product were pooled, concentrated, and dried under vacuum to yield the product (531 mg, 52.4% yield). ¹H NMR (400 MHz, DMSO-d₆) δ 9.43 (s, NH), 8.73 (s, 1H), 8.44 (s, 1H), 8.01 (s, 1H), 4.58 (t, J=5.2 Hz, 1H), 4.52 (ddd, J=9.5, 9.5, 4.5 Hz, 1H), 3.25-3.16 (overlap, 2H), 3.23 (s, 6H), 3.12 (d, J=5.3 Hz, 2H), 2.37 (m, 1H), 1.80 (m, 1H), 1.63-1.13 (overlap, 7H), 1.48 (s, 9H).

Alternative protecting groups were also tested, as shown in Table 4 below:

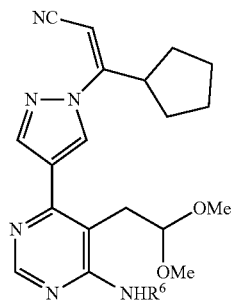

2.5 mol % Rh(COD)₂BF₄
2.5 mol % Walphos SL-W022-1
5 vol solvent, 10 bar H₂
23° C.

116

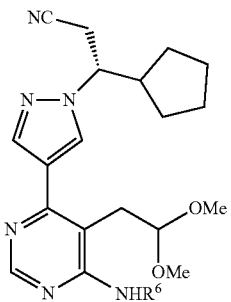

TABLE 4

| Solvent | R⁶ | % AUC |
|---|---|---|
| DCM | Trifluoroacetyl (F₃-Ac) | 23% |
| DCM | Trityl (Tr) | 10% |
| DCM | Triflate (Tf) | 97.6% |
| TFE | Triflate (Tf) | 86.5% |

Additional catalyst systems were also tested for the hydrogenation step, with the results shown below:

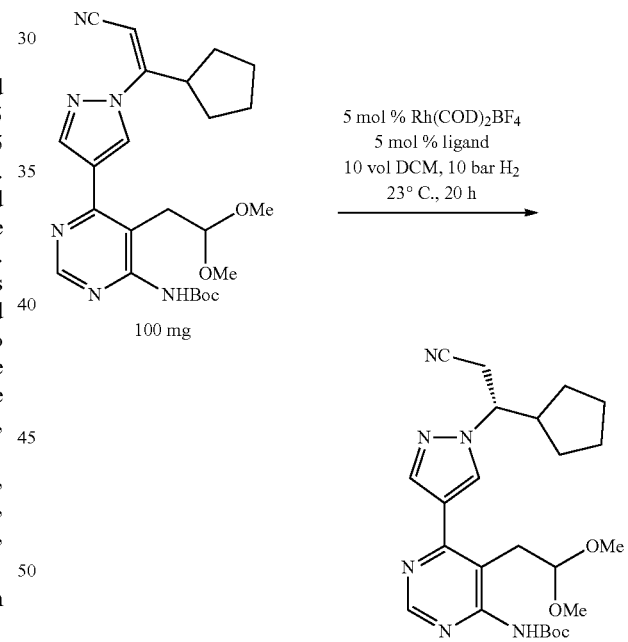

5 mol % Rh(COD)₂BF₄
5 mol % ligand
10 vol DCM, 10 bar H₂
23° C., 20 h

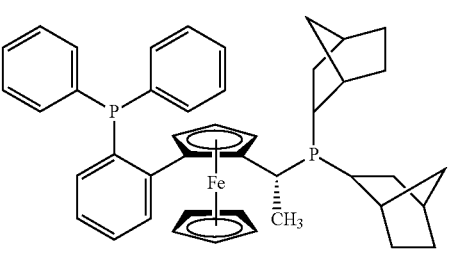

Walphos W022-1, 100% conversion, 99.6:0.4 er

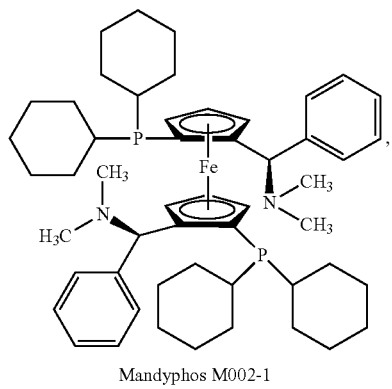

Mandyphos M002-1

100% conversion, 91:9 er

| Ligand Name | % Conversion | Enantiomeric Excess |
|---|---|---|
| Walphos W022-1 | 100 | 99.6:0.4 er |
| Mandyphos M002-1 | 100 | 91:9 er |
| Walphos W012-1 | 2 | |
| W029-1 | 1 | |
| W030-1 | 1 | |
| Taniaphos T002-1 | 6 | |

All ligands are available from Solvias AG (Kaiseraugst, Switzerland) and/or Strem Chemicals (Newburyport, MA, USA).

Step 5B: Preparation of (R)-3-(4-(7H-Pyrrolo[2,3-d]pyrimidin-4-yl)-1H-pyrazol-1-yl)-3-cyclopentylpropanenitrile (ruxolitinib)

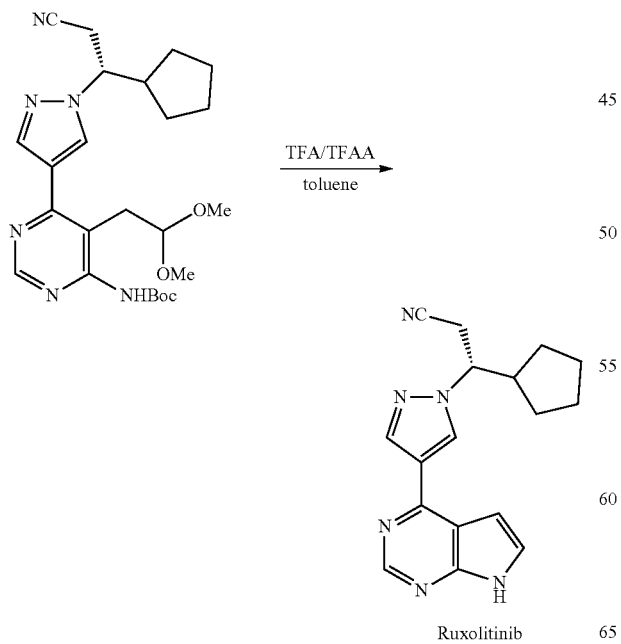

Ruxolitinib

To an HPLC vial containing the amino acetal (50 mg, 0.108 mmol) was added toluene (0.508 mL, 10 volumes) to dissolve the material. To the flask was then added trifluoroacetic acid (0.0508 mL, 1 volume) and the plate was set to 100° C. and reaction allowed to stir. Reaction was monitored by HPLC. After 15 minutes, a sample was taken which showed >90% conversion to product. The reaction was allowed to cool to 40° C. and then to the vial was added trifluoroacetic anhydride (0.0508 mL, 1 volume). After 15 minutes, the reaction had gone to completion. Triethyl amine (0.0508 mL, 1 volume) was added to neutralize the reaction. The mixture was then diluted with EtOAc and the organic phase washed twice with 10 volumes water. The crude product was dried over sodium sulfate and concentrated to yield the product as a white foam. Chiral HPLC (AD-H column, 1 mL/min flow, 50:50 MeOH:EtOH with 0.1% diethylamine) showed an enantiometic ratio of 99.6:0.4, ruxolitinib to the undesired enantiomer. $^1$H NMR (400 MHz, Methanol-$d_4$) δ 8.69 (s, 1H), 8.66 (d, J=0.8 Hz, 1H), 8.39 (s, 1H), 7.55 (d, J=3.7 Hz, 1H), 6.99 (d, J=3.7 Hz, 1H), 4.50 (ddd, J=9.8, 9.8, 4.0 Hz, 1H), 3.23 (dd, J=17.1, 9.6 Hz, 1H), 3.12 (dd, J=17.2, 4.1 Hz, 1H), 2.55 (m, 1H), 1.95 (m, J=12.0, 7.6, 4.1 Hz, 1H), 1.82-1.17 (overlap, 7H).

Without further description, it is believed that one of ordinary skill in the art can, using the preceding description and the illustrative examples, make and utilize the compounds of the present invention and practice the claimed methods. It should be understood that the foregoing discussion and examples merely present a detailed description of certain preferred embodiments. It will be apparent to those of ordinary skill in the art that various modifications and equivalents can be made without departing from the spirit and scope of the invention.

What is claimed is:

1. A process for preparing a compound of Formula I:

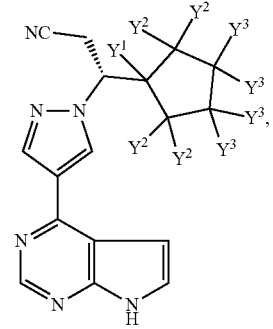

Formula I or a salt thereof,
the process comprising reacting a compound of Formula II':

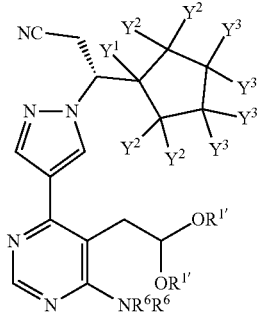

Formula II' or a salt thereof, in the presence of an acid such that a compound of Formula I is formed;
wherein in Formula I and Formula II',
Y¹ is hydrogen or deuterium;
each Y² is the same and is hydrogen or deuterium;
each Y³ is the same and is hydrogen or deuterium;
and in Formula II',
each R¹' is $C_1$-$C_{10}$ alkyl, or $C_2$-$C_{10}$ alkenyl, or the two R¹'s, taken together with the oxygen atoms to which they are attached, form a 5-7-membered heterocyclic ring which may optionally be substituted; and
each R⁶ is independently selected from H and a protecting group.

2. The process of claim 1, wherein the acid is selected from trifluoroacetic acid (TFA), phosphoric acid, hydrochloric acid, or a combination thereof.

3. A process for preparing a compound of Formula II':

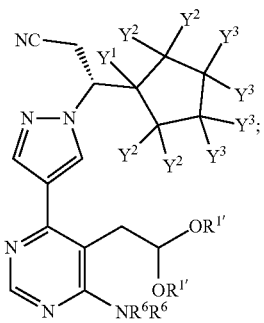

Formula II' or a salt thereof;
the process comprising reacting a compound of Formula III':

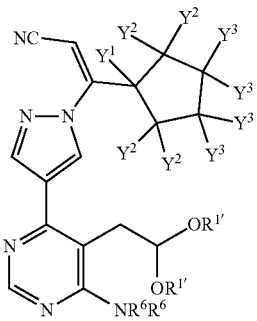

Formula III' or a salt thereof;
with hydrogen gas in the presence of a hydrogenation catalyst;
wherein:
Y¹ is hydrogen or deuterium;
each Y² is the same and is hydrogen or deuterium;
each Y³ is the same and is hydrogen or deuterium;
each R¹' is $C_1$-$C_{10}$ alkyl, or $C_2$-$C_{10}$ alkenyl, or the two R¹'s, taken together with the oxygen atoms to which they are attached, form a 5-7-membered heterocyclic ring which may optionally be substituted; and
each R⁶ is independently selected from H and a protecting group.

4. The process of claim 3, wherein the hydrogenation catalyst comprises rhodium and a chiral phosphine ligand (L) according to Formula IV:

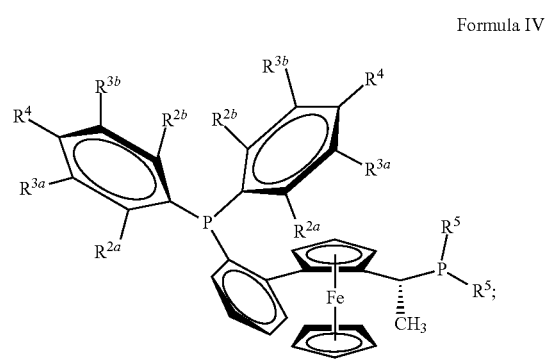

Formula IV wherein each of $R^{2a}$, $R^{2b}$, $R^{3a}$, $R^{3b}$, and $R^4$ is independently selected from hydrogen, methyl, methoxy, and trifluoromethyl; and $R^5$ is secondary alkyl, tertiary alkyl, or cycloalkyl.

5. The process of claim 4, wherein each of $R^{2a}$, $R^{2b}$, $R^{3a}$, $R^{3b}$, and $R^4$ is hydrogen, and $R^5$ is norbornyl or cyclohexyl.

6. The process according to claim 4, wherein the hydrogenation catalyst is present in an amount of 1 mol % or less, and wherein the compound of Formula II' has an enantiomeric excess of the (R)-enantiomer of at least 95%.

7. The process according to claim 3, wherein the step of reacting is performed in a solvent, and the solvent is selected from dichloromethane (DCM), trifluorotoluene (TFT), tetrahydrofuran (THF), 2-methyltetrahydrofuran (2-methyl-THF), methanol (MeOH), ethanol (EtOH), trifluoroethanol (TFE), isopropanol (iPrOH), hexafluoroisopropanol (HFIP), ethyl acetate (EtOAc), isopropyl acetate (iPrOAc), acetic acid (AcOH), and mixtures thereof.

8. The process according to claim 7, wherein the solvent is trifluoroethanol (TFE).

9. The process according to claim 6, wherein the compound of Formula II' has an enantiomeric excess of the (R)-enantiomer of at least 98%.

10. The process according to claim 3, further comprising the step of treating the compound of Formula II' with an acid to form a salt of the compound of Formula II', wherein the acid is selected from D-dibenzoyl tartaric acid, orotic acid, 4-nitrobenzoic acid, 1-hydroxy-2-naphthoic acid, salicylic acid, and 4-bromobenzoic acid.

11. A process for preparing a compound of Formula III':

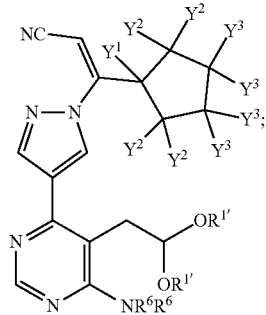

Formula III' or a salt thereof;

the process comprising reacting a compound of Formula VIII':

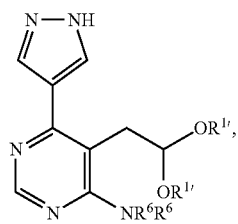

Formula VIII or a salt thereof;
with a compound of Formula VII:

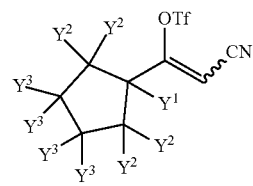

Formula VII or a salt thereof;
in the presence of a base, such that a compound of Formula III', or a salt thereof, is formed;
wherein:
$Y^1$ is hydrogen or deuterium;
each $Y^2$ is the same and is hydrogen or deuterium;
each $Y^3$ is the same and is hydrogen or deuterium;
each $R^{1'}$ is $C_1$-$C_{10}$ alkyl, or $C_2$-$C_{10}$ alkenyl, or the two $R^1$'s, taken together with the oxygen atoms to which they are attached, form a 5-7-membered heterocyclic ring which may optionally be substituted; and
each $R^6$ is independently selected from H and a protecting group.

12. The process of claim 11, wherein the base is selected from tripotassium phosphate, hydrated tripotassium phosphate and potassium carbonate.

13. The process according to claim 1, wherein the protecting group is selected from t-butoxycarbonyl, triflyl, trifluoroacetyl, and trityl.

14. The process according to claim 1, wherein both $R^6$ are H.

15. The process according to claim 1, wherein both $R^1$ are methyl, and wherein $Y^1$ is hydrogen and each of $Y^2$ and $Y^3$ is deuterium.

16. The process according to claim 1, wherein each of $Y^1$, $Y^2$, and $Y^3$ is hydrogen.

17. The process according to claim 1, wherein the deuterium incorporation at each position designated as deuterium is at least 90%.

18. The process according to claim 1, wherein the deuterium incorporation at each position designated as deuterium is at least 95%.

19. The process according to claim 1, wherein the deuterium incorporation at each position designated as deuterium is at least 97%.

* * * * *